(12) United States Patent
Thompson et al.

(10) Patent No.: US 11,576,933 B2
(45) Date of Patent: Feb. 14, 2023

(54) COMPOSITIONS AND METHODS FOR AN IMPROVED ANTITUMOR IMMUNE RESPONSE

(71) Applicant: EFFECTOR THERAPEUTICS, INC., San Diego, CA (US)

(72) Inventors: Peggy A. Thompson, San Diego, CA (US); Kevin R. Webster, San Diego, CA (US)

(73) Assignee: eFFECTOR Therapeutics Inc., San Diego, CA (US)

( * ) Notice: Subject to any disclaimer, the term of this patent is extended or adjusted under 35 U.S.C. 154(b) by 452 days.

(21) Appl. No.: 16/616,087

(22) PCT Filed: May 24, 2018

(86) PCT No.: PCT/US2018/034474
§ 371 (c)(1),
(2) Date: Nov. 22, 2019

(87) PCT Pub. No.: WO2018/218072
PCT Pub. Date: Nov. 29, 2018

(65) Prior Publication Data
US 2020/0147135 A1   May 14, 2020

Related U.S. Application Data

(60) Provisional application No. 62/510,643, filed on May 24, 2017.

(51) Int. Cl.
| | | |
|---|---|---|
| *A61K 35/17* | (2015.01) | |
| *A61P 35/00* | (2006.01) | |
| *A61K 31/343* | (2006.01) | |
| *A61K 31/4355* | (2006.01) | |
| *A61K 45/06* | (2006.01) | |
| *C07D 471/12* | (2006.01) | |

(52) U.S. Cl.
CPC ............ *A61K 35/17* (2013.01); *A61K 31/343* (2013.01); *A61K 31/4355* (2013.01); *A61K 45/06* (2013.01); *A61P 35/00* (2018.01); *C07D 471/12* (2013.01)

(58) Field of Classification Search
CPC ....................................................... A61K 35/17
See application file for complete search history.

(56) References Cited

U.S. PATENT DOCUMENTS

2015/0224132 A1   8/2015   Appleman et al.

FOREIGN PATENT DOCUMENTS

| WO | 2013/016658 A1 | 1/2013 |
| WO | 2017/091585 A1 | 6/2017 |

OTHER PUBLICATIONS

Pinedo et al. (2000) McMahon et al. (2000).*
Tao et al. J'nal of Med Chem. vol. 55, No. 20, (2012).*
Wang et al. (2016) Am J Transl Res, pp. 1047-1054.*
Zhou etal (2014) Molecular Cancer, Bio Med Central, vol. 13, (1).*
"International Preliminary Report on Patentability received for PCT International Application No. PCT/US18/34474", dated Nov. 26, 2019, 11 pages.
"International Search Report and Written Opinion received for PCT Patent International Application No. PCT/US18/34474", dated Aug. 16, 2018, 14 pages.
Liu et al. (Oct. 1, 2012) "Synthetic Silvestrol Analogues as Potent and Selective Protein Synthesis Inhibitors", Journal of medicinal chemistry, 55(20):8859-8878.
Liu et al. (Oct. 9, 2012) "Tgf-β Blockade Improves the Distribution and Efficacy of Therapeutics in Breast Carcinoma by Normalizing the Tumor Stroma", Proceedings of the National Academy of Sciences, 109 (41):16618-16623.
Luan et al. (2014) "Targeting the Prohibitin Scaffold-craf Kinase Interaction in Ras-erk-driven Pancreatic Ductal Adenocarcinoma", Molecular Cancer, Article 38, 13:11 pages.
Terabe et al. (Mar. 2017) "Blockade of only Tgf-β 1 and 2 is Sufficient to Enhance the Efficacy of Vaccine and Pd-1 Checkpoint Blockade Immunotherapy,", Oncoimmunology, 6(5):13 pages.
Wang et al. (2016) "Chinese Herb Derived-Rocaglamide A is a Potent Inhibitor of Pancreatic Cancer Cells", American Journal of Translational Research, 8(2):1047-1054.
Bellomo, et al., "Transforming growth factor β as regulator of cancer stemness and metastasis," British Journal of Cancer 115:761-769 (2016).

* cited by examiner

*Primary Examiner* — Paul V Ward
(74) *Attorney, Agent, or Firm* — Mintz Levin Cohn Ferris Glovsky and Popeo, P.C.

(57) ABSTRACT

The present disclosure provides compositions and methods for improving an antitumor response against non-inflamed solid tumors. Methods of this disclosure include use of an eIF4A inhibitor to promote infiltration of antitumor lymphocytes into a non inflamed solid tumor. Methods of treating cancer associated with a non-inflamed solid tumor are also provided.

16 Claims, 5 Drawing Sheets

COMPOSITIONS AND METHODS FOR AN IMPROVED ANTITUMOR IMMUNE RESPONSE

BACKGROUND

Histologically, tumors can be broadly categorized as inflamed or non-inflamed. Inflamed tumors are characterized by the presence of tumor-infiltrating lymphocytes (TIL), including a high density of $CD8^+$ effector T cells. In contrast, non-inflamed tumors are immunologically ignorant and are poorly infiltrated by lymphocytes. In many cases, lymphocytes accumulate in the stroma and are excluded from the tumor islets. To evade immune surveillance and lymphocyte infiltration, tumors are believed to create an immunosuppressive microenvironment by recruiting myeloid-derived suppressor cells and by secreting factors such as TGFβ, which plays a dual role of inducing the expression of extracellular matrix genes and suppressing expression of signaling molecules important for T-cell infiltration. The resulting reactive stroma and dense extracellular matrix create a barrier to infiltration, producing an excluded infiltrate phenotype with peritumoral or stromal T-cell localization. Tumors that exhibit gene expression signatures of reactive stroma or TGFβ signaling are often associated with lower expression of immune markers and poor outcomes across a number of cancer types.

Currently, there remains a need for improved approaches to treating non-inflamed tumors in a variety of cancers. Presently disclosed embodiments address this need and provide other related advantages.

DETAILED DESCRIPTION

Figure 1:
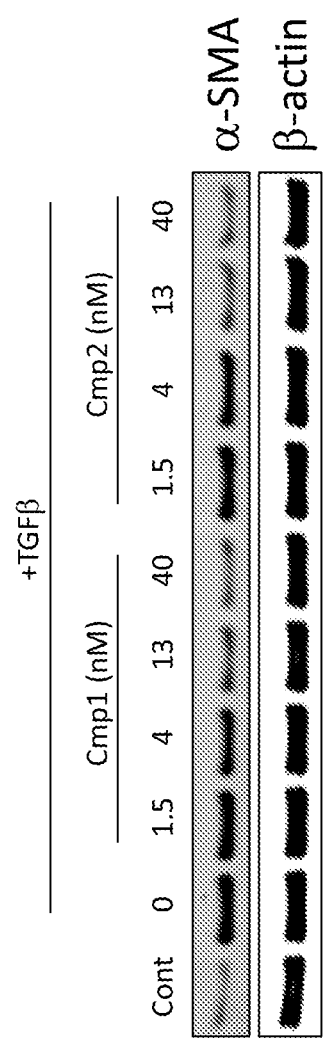
FIG. 1 shows the effect of eIF4A inhibitors Cmp1 (Rac-4-((5aR,6S,7S,8R,8aS)-7-((diethylamino)methyl)-8,8a-dihydroxy-1,3-dimethoxy-6-phenyl-6,7,8,8a-tetrahydro-5aH-cyclopenta[4,5]furo[3,2-c]pyridin-5a-yl)benzonitrile; also referred to herein as Cpd. No. 232F)) and Cmp2 (4-((5aR,6S,7S,8R,8aS)-3-chloro-7-((dimethylamino)methyl)-8,8a-dihydroxy-1-methoxy-6-phenyl-6,7,8,8a-tetrahydro-5aH-cyclopenta[4,5]furo[3,2-c]pyridin-5a-yl)benzonitrile; also referred to herein as Cpd. No. 140F)) on smooth muscle actin (α-SMA) expression levels in fibroblasts treated with TGFβ. The ratio of α-SMA to β-actin (control) was measured by western blot analysis after 24 hours of treating fibroblasts with various concentrations of the eIF4A inhibitors and 10 ng/mL TGFβ.

The present disclosure provides compositions and methods for the treatment of non-inflamed solid tumors and related cancers using inhibitors of eIF4A. In particular, the present disclosure provides inhibitors of eIF4A to promote infiltration of antitumor lymphocytes in the microenvironment of solid tumors, such as non-inflamed solid tumors. By way of background and not wishing to be bound by theory, inhibition of eIF4A can downregulate translation of TGFβ and collagen, which can alter or weaken the extracellular matrix (ECM) in and around a solid tumor in such a way that would allow infiltration of T cells, which would not have been possible with an intact or unaltered ECM.

In certain embodiments, methods of this disclosure comprise combination therapies comprising administering an eIF4A inhibitor in conjunction with one or more additional agents. For example, in some embodiments, an eIF4A inhibitor is used with an inhibitor of an immune suppression component or an agonist of a stimulatory immune checkpoint molecule, as described herein, to enhance an antitumor response by the immune system and to, ultimately, treat a tumor or associated cancer. In some embodiments, methods of this disclosure include administering to a subject an eIF4A inhibitor with an antitumor lymphocyte (e.g., antigen-specific T cells obtained from the subject, T cells modified to contain a chimeric antigen receptor (CAR), or both). In certain embodiments, methods are provided that further comprise administering a secondary therapy comprising one or more of: an antibody or antigen-binding fragment specific for a cancer antigen expressed by the solid tumor being targeted; a chemotherapeutic agent; surgery; radiation therapy treatment; a cytokine; an RNA interference therapy, or any combination thereof.

Prior to setting forth this disclosure in more detail, it may be helpful to an understanding thereof to provide definitions of certain terms to be used herein. Additional definitions are set forth throughout this disclosure.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the term "about" or "consisting essentially of" means±20% of the indicated range, value, or structure, unless otherwise indicated. It should be understood that the terms "a" and "an" as used herein refer to "one or more" of the enumerated components. The use of the alternative (e.g., "or") should be understood to mean either one, both, or any combination thereof of the alternatives. As used herein, the terms "include," "have" and "comprise" are used synonymously, which terms and variants thereof are intended to be construed as non-limiting. The term "consisting essentially of" is not equivalent to "comprising" and refers to the specified materials or steps that do not materially affect the basic characteristics of a claimed invention.

"Optional" or "optionally" means that the subsequently described element, component, event, or circumstance may or may not occur, and that the description includes instances in which the element, component, event, or circumstance occurs and instances in which they do not.

As used herein, "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refer to compounds that have the same basic chemical structure as a naturally occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refer to chemical compounds that have a structure that is different from the general chemical structure of an amino acid, but that functions in a manner similar to a naturally occurring amino acid.

As used herein, "protein" or "polypeptide" refers to a polymer of amino acid residues. Proteins apply to naturally occurring amino acid polymers, as well as to amino acid polymers in which one or more amino acid residue is an artificial chemical mimetic of a corresponding naturally occurring amino acid and non-naturally occurring amino acid polymers. It is well understood that functional proteins or polypeptides can be altered without significantly effects on functionality. For example, conservative substitutions may be made to a protein or polypeptide while preserving activity thereof. A "conservative substitution" refers to amino acid substitutions that do not significantly affect or alter binding characteristics of a particular protein. Generally, conservative substitutions are ones in which a substituted amino acid residue is replaced with an amino acid residue having a similar side chain. Conservative substitutions include a substitution found in one of the following groups: Group 1: Alanine (Ala or A), Glycine (Gly or G), Serine (Ser or S), Threonine (Thr or T); Group 2: Aspartic acid (Asp or D), Glutamic acid (Glu or Z); Group 3: Asparagine (Asn or N), Glutamine (Gln or Q); Group 4: Arginine (Arg or R), Lysine (Lys or K), Histidine (His or H); Group 5: Isoleucine (Ile or I), Leucine (Leu or L), Methionine (Met or M), Valine (Val or V); and Group 6: Phenylalanine (Phe or F), Tyrosine (Tyr or Y), Tryptophan (Trp or W). Additionally or alternatively, amino acids can be grouped into conservative substitution groups by similar function, chemical structure, or composition (e.g., acidic, basic, aliphatic, aromatic, or sulfur-containing). For example, an aliphatic grouping may include, for purposes of substitution, Gly, Ala, Val, Leu, and Ile. Other conservative substitutions groups include: sulfur-containing: Met and Cysteine (Cys or C); acidic: Asp, Glu, Asn, and Gln; small aliphatic, nonpolar or slightly polar residues: Ala, Ser, Thr, Pro, and Gly; polar, negatively charged residues and their amides: Asp, Asn, Glu, and Gln; polar, positively charged residues: His, Arg, and Lys; large aliphatic, nonpolar residues: Met, Leu, Ile, Val, and Cys; and large aromatic residues: Phe, Tyr, and Trp. Additional information can be found in Creighton (1984) Proteins, W.H. Freeman and Company.

"Nucleic acid molecule" or "polynucleotide" refers to a polymeric compound including covalently linked nucleotides, which can be made up of natural subunits (e.g., purine or pyrimidine bases) or non-natural subunits (e.g., morpholine ring). Purine bases include adenine, guanine, hypoxanthine, and xanthine, and pyrimidine bases include uracil, thymine, and cytosine. Nucleic acid molecules include polyribonucleic acid (RNA), polydeoxyribonucleic acid (DNA), which includes cDNA, genomic DNA, and synthetic DNA, either of which may be single or double stranded. If single stranded, the nucleic acid molecule may be the coding strand or non-coding (anti-sense strand). A nucleic acid molecule encoding an amino acid sequence includes all nucleotide sequences that encode the same amino acid sequence. Some versions of the nucleotide sequences may also include intron(s) to the extent that the intron(s) would be removed through co- or post-transcriptional mechanisms. In other words, different nucleotide sequences may encode the same amino acid sequence as the result of the redundancy or degeneracy of the genetic code, or by splicing.

As used herein, the term "translation" refers to a step in gene expression during which messenger RNA (mRNA) is used to produce a specific amino acid chain or polypeptide. During eukaryotic translation, mRNAs are bound by ribosomes to form a translational complex outside of the nucleus, generally in the cytoplasm or across the membrane of the endoplasmic reticulum. Transfer RNAs (tRNAs) carry individual amino acids into the ribosome/mRNA complex. tRNAs typically include an anticodon structure that, if complementary to the mRNA codon present in the ribosome active site at that time, allows for temporary binding to the mRNA. Following binding to the mRNA, the tRNA exits the ribosome/mRNA complex, leaving the amino acid in the ribosome "P" site to form a peptide bond with the amino acid carried by the next tRNA. A series of amino acid deliveries by tRNAs forms a polypeptide chain corresponding to (i.e., encoded by) the genetic information in the mRNA nucleotide sequence. When a stop codon is reached, the ribosome complex releases the polypeptide chain and the mRNA. The polypeptide then undergoes changes in structure (e.g., folding) and other characteristics (e.g., post-translational modifications) to form an active protein that can perform biological functions. Three general phases of translation, outlined above, are known as "initiation" (the ribosome/mRNA complex is assembled and the first tRNA is attached at the start codon of the mRNA), "elongation" (successive amino acids are added to form a polypeptide chain), and "termination" (a stop codon is reached and the polypeptide and mRNA are released).

"Amino" refers to the —NH2 substituent.

"Aminocarbonyl" refers to the —C(O)NH2 substituent.

"Carboxyl" refers to the —CO2H substituent.

"Carbonyl" refers to a —C(O)—, —(CO)— or —C(=O)— group. All notations are used interchangeably within the specification.

"Cyano" refers to the —C≡N substituent.

"Cyanoalkylene" refers to the -(alkylene)C≡N substituent.

"Acetyl" refers to the —C(O)CH3 substituent.

"Hydroxy" or "hydroxyl" refers to the OH substituent.

"Hydroxyalkylene" refers to the -(alkylene)OH substituent.

"Oxo" refers to a =O substituent.

"Thio" or "thiol" refer to a —SH substituent.

"Alkyl" refers to a saturated, straight or branched hydrocarbon chain radical consisting solely of carbon and hydrogen atoms, having from one to twelve carbon atoms (C1-C12 alkyl), from one to eight carbon atoms (C1-C8 alkyl) or from one to six carbon atoms (C1-C6 alkyl), and which is attached to the rest of the molecule by a single bond. Exemplary alkyl groups include methyl, ethyl, n propyl, 1 methylethyl (iso propyl), n butyl, n pentyl, 1,1 dimethylethyl (t butyl), 3 methylhexyl, 2 methylhexyl, and the like.

"Lower alkyl" has the same meaning as alkyl defined above but having from one to four carbon atoms (C1-C4 alkyl).

"Alkenyl" refers to an unsaturated alkyl group having at least one double bond and from two to twelve carbon atoms (C2-C12 alkenyl), from two to eight carbon atoms (C2-C8 alkenyl) or from two to six carbon atoms (C2-C6 alkenyl), and which is attached to the rest of the molecule by a single bond, e.g., ethenyl, propenyl, butenyl, pentenyl, hexenyl, and the like.

"Alkynyl" refers to an unsaturated alkyl group having at least one triple bond and from two to twelve carbon atoms (C2-C12 alkynyl), from two to ten carbon atoms (C2-C10 alkynyl) from two to eight carbon atoms (C2-C8 alkynyl) or from two to six carbon atoms (C2-C6 alkynyl), and which is attached to the rest of the molecule by a single bond, e.g., ethynyl, propynyl, butynyl, pentynyl, hexynyl, and the like.

"Alkylene" or "alkylene chain" refers to a straight or branched divalent hydrocarbon (alkyl) chain linking the rest of the molecule to a radical group, consisting solely of carbon and hydrogen, respectively. Alkylenes can have from one to twelve carbon atoms, e.g., methylene, ethylene, propylene, n butylene, and the like. The alkylene chain is attached to the rest of the molecule through a single or double bond. The points of attachment of the alkylene chain to the rest of the molecule can be through one carbon or any two carbons within the chain. "Optionally substituted alkylene" refers to alkylene or substituted alkylene.

"Alkenylene" refers to divalent alkene. Examples of alkenylene include without limitation, ethenylene (—CH═CH—) and all stereoisomeric and conformational isomeric forms thereof. "Substituted alkenylene" refers to divalent substituted alkene. "Optionally substituted alkenylene" refers to alkenylene or substituted alkenylene.

"Alkynylene" refers to divalent alkyne. Examples of alkynylene include without limitation, ethynylene, propynylene. "Substituted alkynylene" refers to divalent substituted alkyne.

"Alkoxy" refers to a radical of the formula ORa where Ra is an alkyl having the indicated number of carbon atoms as defined above. Examples of alkoxy groups include without limitation —O-methyl (methoxy), —O-ethyl (ethoxy), —O-propyl (propoxy), —O-isopropyl (iso propoxy) and the like.

"Alkylaminyl" refers to a radical of the formula —NHRa or —NRaRa where each Ra is, independently, an alkyl radical having the indicated number of carbon atoms as defined above.

"Cycloalkylaminyl" refers to a radical of the formula —NHRa or —NRaRa where Ra is a cycloalkyl radical as defined herein.

"Alkylcarbonylaminyl" refers to a radical of the formula —NHC(O)Ra or —NRaC(O)Ra, where Ra is an alkyl radical having the indicated number of carbon atoms as defined herein.

"Cycloalkylcarbonylaminyl" refers to a radical of the formula NHC(O)Ra or NRaC(O)Ra where Ra is a cycloalkyl radical as defined herein.

"Alkylaminocarbonyl" refers to a radical of the formula —C(O)NHRa or C(O)NRaRa, where each Ra is independently, an alkyl radical having the indicated number of carbon atoms as defined herein.

"Cyclolkylaminocarbonyl" refers to a radical of the formula —C(O)NHRa, where Ra is a cycloalkyl radical as defined herein.

"Aryl" refers to a hydrocarbon ring system radical comprising hydrogen, 6 to 18 carbon atoms and at least one aromatic ring. Exemplary aryls are hydrocarbon ring system radical comprising hydrogen and 6 to 9 carbon atoms and at least one aromatic ring; hydrocarbon ring system radical comprising hydrogen and 9 to 12 carbon atoms and at least one aromatic ring; hydrocarbon ring system radical comprising hydrogen and 12 to 15 carbon atoms and at least one aromatic ring; or hydrocarbon ring system radical comprising hydrogen and 15 to 18 carbon atoms and at least one aromatic ring. For purposes of this invention, the aryl radical may be a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s indacene, indane, indene, naphthalene, phenalene, phenanthrene, pleiadene, pyrene, and triphenylene. "Optionally substituted aryl" refers to a aryl group or a substituted aryl group.

"Arylene" denotes divalent aryl, and "substituted arylene" refers to divalent substituted aryl.

"Aralkyl" or "araalkylene" may be used interchangeably and refer to a radical of the formula Rb Rc where Rb is an alkylene chain as defined herein and Rc is one or more aryl radicals as defined herein, for example, benzyl, diphenylmethyl and the like.

"Cycloalkyl" refers to a stable non aromatic monocyclic or polycyclic hydrocarbon radical consisting solely of carbon and hydrogen atoms, which may include fused or bridged ring systems, having from three to fifteen carbon atoms, preferably having from three to ten carbon atoms, three to nine carbon atoms, three to eight carbon atoms, three to seven carbon atoms, three to six carbon atoms, three to five carbon atoms, a ring with four carbon atoms, or a ring with three carbon atoms. The cycloalkyl ring may be saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7 dimethyl bicyclo[2.2.1] heptanyl, and the like.

"Cycloalkylalkylene" or "cycloalkylalkyl" may be used interchangeably and refer to a radical of the formula RbRe where Rb is an alkylene chain as defined herein and Re is a cycloalkyl radical as defined herein. In certain embodiments, Rb is further substituted with a cycloalkyl group, such that the cycloalkylalkylene comprises two cycloalkyl moieties. Cyclopropylalkylene and cyclobutylalkylene are exemplary cycloalkylalkylene groups, comprising at least one cyclopropyl or at least one cyclobutyl group, respectively.

"Fused" refers to any ring structure described herein which is fused to an existing ring structure in the compounds of the invention. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo (bromine), chloro (chlorine), fluoro (fluorine), or iodo (iodine).

"Haloalkyl" refers to an alkyl radical having the indicated number of carbon atoms, as defined herein, wherein one or more hydrogen atoms of the alkyl group are substituted with a halogen (halo radicals), as defined above. The halogen atoms can be the same or different. Exemplary haloalkyls are trifluoromethyl, difluoromethyl, trichloromethyl, 2,2,2 trifluoroethyl, 1,2 difluoroethyl, 3 bromo 2 fluoropropyl, 1,2 dibromoethyl, and the like.

"Heterocyclyl", "heterocycle", or "heterocyclic ring" refers to a stable 3- to 18-membered saturated or unsaturated radical which consists of two to twelve carbon atoms and from one to six heteroatoms, for example, one to five heteroatoms, one to four heteroatoms, one to three heteroatoms, or one to two heteroatoms selected from the group consisting of nitrogen, oxygen and sulfur. Exemplary heterocycles include without limitation stable 3-15 membered saturated or unsaturated radicals, stable 3-12 membered saturated or unsaturated radicals, stable 3-9 membered saturated or unsaturated radicals, stable 8-membered saturated or unsaturated radicals, stable 7-membered saturated or unsaturated radicals, stable 6-membered saturated or unsaturated radicals, or stable 5-membered saturated or unsaturated radicals.

Unless stated otherwise specifically in the specification, the heterocyclyl radical may be a monocyclic, bicyclic, tricyclic or tetracyclic ring system, which may include fused, spiro or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of non-aromatic heterocyclyl radicals include, but are not limited to, azetidinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2 oxopiperazinyl, 2 oxopiperidinyl, 2 oxopyrrolidinyl, oxazolidinyl, piperidinyl, piperazinyl, 4 piperidonyl, pyrrolidinyl, pyrazolidinyl, quinuclidinyl, thiazolidinyl, tetrahydrofuryl, thietanyl, trithianyl, tetrahydropyranyl, thiomorpholinyl, thiamorpholinyl, 1 oxo thiomorpholinyl, and 1,1 dioxo thiomorpholinyl. Heterocyclyls include heteroaryls as defined herein, and examples of aromatic heterocyclyls are listed in the definition of heteroaryls below.

"Heterocyclylalkyl" or "heterocyclylalkylene" refers to a radical of the formula RbRf where Rb is an alkylene chain as defined herein and Rf is a heterocyclyl radical as defined above, and if the heterocyclyl is a nitrogen containing heterocyclyl, the heterocyclyl may be attached to the alkyl radical at the nitrogen atom.

"Heteroaryl" or "heteroarylene" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical may be a stable 5-12 membered ring, a stable 5-10 membered ring, a stable 5-9 membered ring, a stable 5-8 membered ring, a stable 5-7 membered ring, or a stable 6 membered ring that comprises at least 1 heteroatom, at least 2 heteroatoms, at least 3 heteroatoms, at least 4 heteroatoms, at least 5 heteroatoms or at least 6 heteroatoms. Heteroaryls may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. The heteroatom may be a member of an aromatic or non-aromatic ring, provided at least one ring in the heteroaryl is aromatic. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4 benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2 a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2 oxoazepinyl, oxazolyl, oxiranyl, 1-oxidopyridinyl, 1 oxidopyrimidinyl, 1-oxidopyrazinyl, 1-oxidopyridazinyl, 1 phenyl 1H pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl).

"Heteroarylalkyl" or "heteroarylalkylene" refers to a radical of the formula RbRg where Rb is an alkylene chain as defined above and Rg is a heteroaryl radical as defined above.

"Thioalkyl" refers to a radical of the formula —SRa where Ra is an alkyl radical as defined above containing one to twelve carbon atoms, at least 1-10 carbon atoms, at least 1-8 carbon atoms, at least 1-6 carbon atoms, or at least 1-4 carbon atoms.

"Heterocyclylaminyl" refers to a radical of the formula —NHRf where Rf is a heterocyclyl radical as defined above.

"Thione" refers to a =S group attached to a carbon atom of a saturated or unsaturated (C3-C8)cyclic or a (C1-C8) acyclic moiety.

"Sulfoxide" refers to a —S(O)— group in which the sulfur atom is covalently attached to two carbon atoms.

"Sulfone" refers to a —S(O)2- or —(SO2)- group in which a hexavalent sulfur is attached to each of the two oxygen atoms through double bonds and is further attached to two carbon atoms through single covalent bonds.

The term "oxime" refers to a —C(Ra)=N—ORa radical where Ra is hydrogen, lower alkyl, an alkylene or arylene group as defined above.

The compounds of the present disclosure can exist in various isomeric forms, as well as in one or more tautomeric forms, including both single tautomers and mixtures of tautomers. The term "isomer" is intended to encompass all isomeric forms of a compound of this invention, including tautomeric forms of the compound.

Some compounds described herein can have asymmetric centers and therefore exist in different enantiomeric and diastereomeric forms. A compound of this disclosure can be in the form of an optical isomer or a diastereomer. Accordingly, compounds and their uses as described herein in the form of their optical isomers, diastereoisomers and mixtures thereof, including a racemic mixture, are encompassed by the instant disclosure. Optical isomers of the compounds of the invention can be obtained by known techniques, such as asymmetric synthesis, chiral chromatography, or via chemical separation of stereoisomers through the employment of optically active resolving agents.

Unless otherwise indicated, "stereoisomer" means one stereoisomer of a compound that is substantially free of other stereoisomers of that compound. Thus, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, for example, greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound.

If there is a discrepancy between a depicted structure and a name given to that structure, then the depicted structure controls. Additionally, if the stereochemistry of a structure or a portion of a structure is not indicated with, for example, bold or dashed lines, the structure or portion of the structure is to be interpreted as encompassing all stereoisomers of it. In some cases, however, where more than one chiral center exists, the structures and names may be represented as single enantiomers to help describe the relative stereochemistry. Those skilled in the art of organic synthesis will know if the compounds are prepared as single enantiomers from the methods used to prepare them.

In this description a "pharmaceutically acceptable salt" is a pharmaceutically acceptable, organic or inorganic acid or base salt of a compound of the invention. Representative pharmaceutically acceptable salts include, e.g., alkali metal salts, alkali earth salts, ammonium salts, water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosaliculate, suramate, tannate, tartrate, teoclate, tosylate, triethiodide, and valerate salts. A pharmaceutically acceptable salt can have more than one charged atom in its structure. In this instance the pharmaceutically acceptable salt can have multiple counterions. Thus, a pharmaceutically acceptable salt can have one or more charged atoms and/or one or more counterions.

eIF4A Inhibitors

As used herein, "eIF4A," also known as "eukaryotic initiation factor-4A," refers to a member of the "DEAD box" family of ATP-dependent helicases that are characterized by seven highly conserved amino acid motifs implicated in RNA remodeling. eIF4A acts as an RNA-dependent ATPase and ATP-dependent RNA helicase to facilitate mRNA binding to the ribosome as part of the eIF4F (eukaryotic initiation factor 4F) complex that recognizes and initiates translation of most cellular mRNAs to synthesize specific proteins. A functional eIF4F complex consisting of eIF4A, eIF4E and eIF4G is involved in translation of mRNAs that contain highly structured 5'-UTRs or an IRES element. In particular, eIF4F recognizes the cap structure at the 5'-end of mRNA through eIF4E, unwinds the secondary structure of the 5'-UTR region through the helicase activity of eIF4A, and binds the 43 S complex through interactions between eIF4G and eIF3. See, e.g., Marintchev et al., *Cell*, 136: 447-460, 2009, and Parsyan et al., *Nat. Rev. Mol. Cell Biol.* 12:235-245, 2012. eIF4A selectively regulates the translation of a subset of mRNAs. This selectivity is believed to be a result of structural elements and sequence recognition motifs found within the 5'-UTR of the mRNA. There are three eIF4A family members: eIF4AI, eIF4AII, and eIF4AIII. In particular embodiments, eIF4A refers to human eIF4A. Overexpression of eIF4A has been associated with poor prognosis in various cancers, including lymphoma, lung cancer, colon cancer, liver cancer, ovarian cancer and breast cancer.

As described herein, tumors may be broadly categorized on the basis of inflammatory state. Inflamed tumors are characterized by the presence of lymphocytes that have departed the bloodstream and infiltrated the tumor, and in particular by a high density of $CD8^+$ effector T cells. In contrast, non-inflamed tumors are poorly infiltrated by lymphocytes and, in many cases, are characterized by aberrant expression or activity of TGFβ, a dense extracellular matrix (e.g., comprised of collagen and other matrix proteins), and an excluded infiltrate phenotype with peritumoral or stromal T-cell localization. The degree to which $CD8^+$ T cells and other lymphocytes infiltrate a tumor may be determined using a number of methods, including, for example, by histological analysis using staining for lymphocyte proteins such as CD3 or CD8, or by gene expression assays such as DNA microarray or RNA sequencing.

In certain aspects, the present disclosure relates to the use of eIF4A inhibitors to regulate (i.e., reduce) eIF4A-mediated translation of, for example, TGFβ and collagen in solid tumors, such as non-inflamed tumors. The term "inhibit" or "inhibitor" refers to an alteration, interference, reduction, down-regulation, blocking, suppression, abrogation or degradation, either directly or indirectly, in the expression, amount, or activity of a target or signaling pathway relative to (1) a control, endogenous or reference target or pathway, or (2) the absence of a target or pathway, wherein the alteration, interference, reduction, down-regulation, blocking, suppression, abrogation or degradation is statistically, biologically, or clinically significant. The term "inhibit" or "inhibitor" includes gene "knock out" and gene "knock down" methods, such as by chromosomal editing.

An "eIF4A inhibitor," as used herein, refers to an agent or compound that directly interacts with eIF4A, either alone or in a complex (e.g., a ternary complex of an eIF4A inhibitor, an eIF4A and a mRNA) and may block, inactivate, reduce or minimize eIF4A activity (e.g., helicase activity or translational effects), or reduce activity by promoting degradation of eIF4A, by about 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or more as compared to untreated eIF4A. In certain embodiments, an eIF4A inhibitor is a catalytic inhibitor that directly inhibits eIF4A helicase activity. An example of an eIF4A catalytic inhibitor is BPSL1549, a bacterial toxin from *Burkholderia pseudomallei* that deamidates Gln339 of eIF4A and converts it into a dominant-negative mutant (see, e.g., Cruz-Migoni et al., *Science* 334:821-824, 2011, which inhibitor is incorporated herein by reference in its entirety).

In some embodiments, an eIF4A inhibitor is an allosteric inhibitor. An allosteric eIF4A inhibitor binds to eIF4A at a site other than the active site, wherein its binding induces a conformational change in eIF4A so that a substrate can no longer bind eIF4A or eIF4A activity is reduced. In certain embodiments, an allosteric eIF4A inhibitor includes hippuristanol (see, e.g., Bordeleau et al., *Nat Chem. Biol.* 2: 213-220, 2006, which compound is incorporated herein by reference in its entirety) and derivatives or analogs thereof.

Hippuristanol, which binds the C-terminal domain of both free eIF4A (eIF4A$_f$) and eIF4A bound in an eIF4F complex (eIF4A$_c$), inhibits eIF4A helicase and ATPase activities.

In some embodiments, an eIF4A inhibitor is a chemical inducer of dimerization. An eIF4A chemical inducer of dimerization causes a non-sequence-specific interaction between eIF4A$_f$ and RNA and stimulates the ATP hydrolysis activity of eIF4A, resulting in sequestering of eIF4A$_f$ and depletion of eIF4A$_c$. Examples of eIF4A inhibitors that are chemical inducers of dimerization include pateamine A, and analogs, derivatives, or precursors thereof. Examples of pateamine A derivatives have been described in, for example, U.S. Pat. No. 7,230,021; PCT Publication WO 2016/161168 (α-amino derivatives that lack the C5-methyl group); and U.S. Pat. No. 7,737,134 (desmethyl, desamino-pateamine A derivatives), each derivative of which is incorporated by reference in its entirety.

In some embodiments, an eIF4A inhibitor is a site-directed eIF4A inhibitor. A "site-directed eIF4A inhibitor," as used herein, is an agent or compound that interacts with a specific nucleotide sequence of a mRNA molecule, such as a non-coding nucleotide sequence (e.g., located in the 5'-UTR of a target mRNA), and is capable of forming a stable ternary complex comprised of the site-directed eIF4A inhibitor, an eIF4A and a target mRNA. Exemplary site-directed eIF4A inhibitors include silvestrol, rocaglamide compounds, as well as analogs, derivatives, or precursors thereof. Representative silvestrol derivatives and analogs include CR-1-31-B, hydroxamate derivative of silvestrol (see, e.g., Rodrigo et al., *J. Med. Chem.* 55:558-562, 2012; which compounds are incorporated herein by reference in their entirety); episilvestrol (see, e.g., Hwang et al., *J. Org. Chem.* 69:3350-3358, 2004; which compound is incorporated herein by reference in its entirety); Compounds 74 and 76 see, e.g., (Liu et al., *J. Med. Chem.* 55:8859-8878, 2012, which compounds are incorporated herein by reference in their entirety), silvestrol dioxane, episilvesterol dioxane, Flavagline 61, (−)-4'-desmethoxyepi silvestrol, and 1-O-formylaglafoline (FA). Examples of rocaglates and precursors include aglapervirisin A and aglapervirisins B-J (see, e.g., An et al., *Scientific Reports*, Article No. 20045, 2016). Further examples of naturally silvestrol and rocaglamide derivatives and analogs are described in, for example, Pan et al., *Nat. Prod. Rep.* 31:924-939, 2014; Kim et al., *Anticancer Agents Med. Chem.* 6:319-45, 2006; and U.S. Patent Publication US 2014/0255432, compounds from each of which is incorporated herein by reference in its entirety.

Inhibition of eIF4A may be measured by, for example, decreased rates or amounts of protein translation. For example, in certain embodiments, administration of a therapeutically effective amount of an eIF4A inhibitor may reduce translation of TGFβ, collagen, or both, in a non-inflamed solid tumor by at least about 1.5-fold (e.g., at least about 1.5-fold, at least about 2-fold, at least about 2.5-fold, at least about 3-fold, at least about 3.5-fold, at least about 4-fold, at least about 4.5-fold, at least about 5-fold, at least about 6-fold, at least about 7-fold, at least about 8-fold, at least about 9-fold, at least about 10-fold or more) as compared to an untreated reference non-inflamed solid tumor.

Exemplary site-directed eIF4A inhibitors of this disclosure include compounds according to Formula I:

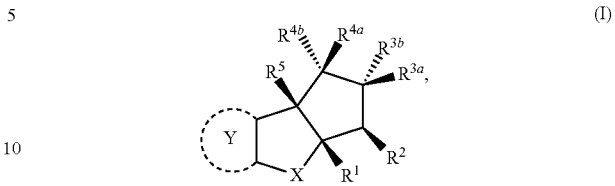

or stereoisomers, tautomers or pharmaceutically acceptable salts thereof,
wherein:
X is CR$^6$R$^7$, O, S, NH, N(C$_1$-C$_8$)alkyl, C(O), C=CR$^6$R$^7$, N(CO)R$^8$, S(O) or S(O)$_2$;
Y is a 5-membered heteroaryl or a 6-membered aryl or heteroaryl;
R$^1$ and R$^2$ independently are aryl, heterocyclyl, heteroaryl or cycloalkyl;
R$^{3a}$, R$^{3b}$, R$^{4a}$ and R$^{4b}$ independently are H, halogen, CN, C$_1$-C$_8$(alkyl), (C$_1$-C$_8$)haloalkyl, C$_2$-C$_8$(alkenyl), (C$_2$-C$_8$) alkynyl, OR$^9$, NHR$^9$, NR$^9$R$^9$, [(C$_1$-C$_8$)alkylene]OR$^9$, [(C$_1$-C$_8$)alkylene]NHR$^9$, [(C$_1$-C$_8$)alkylene]NR$^9$R$^9$, C(O)R$^8$, C(O)NHR$^9$, C(O)NR$^9$R$^9$, C(O)[(C$_1$-C$_8$)alkylene]NHR$^9$, C(O)[(C$_1$-C$_8$)alkylene]NR$^9$R$^9$, CO$_2$R$^9$, C(S)NHR$^9$, C(S)NR$^9$R$^9$, SR$^9$, S(O)R$^9$, SO$_2$R$^9$, SO$_2$NHR$^9$, SO$_2$NR$^9$R$^9$, NH(CO)R$^8$, NR$^9$(CO)R$^8$, NH(CO)NHR$^9$, NH(CO)NR$^9$R$^9$, NR$^9$(CO)NHR$^9$, NR$^9$(CO)NR$^9$R$^9$, P(O)(OH)(OR$^9$), P(O)(OR$^9$)(OR$^9$), aryl, heteroaryl, cycloalkyl or heterocyclyl;
R$^{3a}$ and R$^{3b}$, and R$^{4a}$ and R$^{4b}$ independently combine to form oxo or alkenyl, or a cycloalkyl or heterocyclyl ring; or
R$^{3a}$ and R$^{4a}$, R$^{3b}$ and R$^{4b}$ or R$^{4a}$ and R$^5$ together with the carbon atom to which they are attached form a cycloalkyl or heterocyclyl ring; or
R$^2$ and R$^{3a}$ together with the carbon atom to which they are attached form a bicyclic ring system;
R$^5$ is H, halogen, OH, CN, N$_3$, SR$^9$, (C$_1$-C$_8$)alkyl, (C$_1$-C$_8$)haloalkyl, O(C$_1$-C$_8$)alkyl, O(C$_1$-C$_8$)haloalkyl, (C$_2$-C$_8$) alkynyl, NHC(O)(C$_1$-C$_8$)alkyl or heteroaryl;
R$^6$ and R$^7$ independently are H, CN, halogen, OR$^9$, SR$^9$, (C$_1$-C$_8$)alkyl, NH(R$^9$) or NR$^9$R$^9$;
R$^8$ is H, (C$_1$-C$_8$)alkyl, (C$_1$-C$_8$)haloalkyl, O(C$_1$-C$_8$)alkyl, O(C$_1$-C$_8$)haloalkyl, cycloalkyl, O(cycloalkyl), heterocyclyl, O(heterocyclyl), aryl, O(aryl), heteroaryl or O(heteroaryl);
R$^9$ is H, (C$_1$-C$_8$)alkyl, (C$_1$-C$_8$)haloalkyl, cycloalkyl, heterocyclyl, [(C$_1$-C$_8$)alkylene] heterocyclyl, aryl, [(C$_1$-C$_8$)alkylene] aryl or heteroaryl;
wherein the two R$^9$'s together with the nitrogen atom to which they are attached of NR$^9$R$^9$, [(C$_1$-C$_8$)alkylene] NR$^9$R$^9$, C(O)NR$^9$R$^9$, C(O)[(C$_1$-C$_8$)alkylene]NR$^9$R$^9$, C(S) NR$^9$R$^9$, SO$_2$NR$^9$R$^9$, NH(CO)NR$^9$R$^9$ or NR$^9$(CO)NR$^9$R$^9$, optionally form a heterocyclyl ring;
wherein any alkyl, alkenyl, cycloalkyl, heterocyclyl, heteroaryl or aryl is optionally substituted with 1, 2, or 3 groups selected from OH, CN, SH, SO$_2$NH$_2$, SO$_2$(C$_1$-C$_4$)alkyl, SO$_2$NH(C$_1$-C$_4$)alkyl, halogen, NH$_2$, NH(C$_1$-C$_4$)alkyl, N[(C$_1$-C$_4$)alkyl]$_2$, C(O)NH$_2$, COOH, COOMe, acetyl, (C$_1$-C$_8$)alkyl, O(C$_1$-C$_8$)alkyl, O(C$_1$-C$_8$)haloalkyl, (C$_2$-C$_8$)alkenyl, (C$_2$-C$_8$)alkynyl, haloalkyl, thioalkyl, cyanomethylene, alkylaminyl, NH$_2$—C(O)-alkylene, NH(Me)-C(O)-alkylene, CH$_2$—C(O)-lower alkyl, C(O)-lower alkyl, alkyl-carbonylaminyl, CH$_2$—[CH(OH)]$_m$—(CH$_2$)$_p$—OH, CH$_2$—[CH(OH)]$_m$—(CH$_2$)$_p$—NH$_2$ or CH$_2$-aryl-alkoxy; or
wherein any alkyl, cycloalkyl or heterocyclyl is optionally substituted with oxo;
"m" and "p" are 1, 2, 3, 4, 5 or 6; and
wherein when Y is a 6-membered aryl then X is not O.

In some embodiments, the 6-membered aryl or heteroaryl is

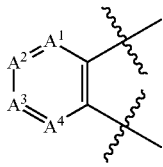

wherein
A¹ is N or CR¹;
A² is N or CR¹¹;
A³ is N or CR¹²;
A⁴ is N or CR¹³; and
R¹⁰, R¹¹, R¹² and R¹³ independently are H, halogen, $C_1$-$C_8$(alkyl), ($C_1$-$C_8$)haloalkyl, C(O)O($C_1$-$C_8$)alkyl, C(O)($C_1$-$C_8$)alkyl, $SO_2$($C_1$-$C_8$)alkyl, $C_2$-$C_8$(alkenyl), ($C_2$-$C_8$) alkynyl, $OR^9$, $NHR^9$, $NR^9R^9$, CN, [($C_1$-$C_8$)alkylene]$OR^9$, [($C_1$-$C_8$)alkylene]$NHR^9$, [($C_1$-$C_8$)alkylene]$NR^9R^9$, $C(O)R^8$, $C(O)NHR^9$, $C(O)NR^9R^9$, $C(O)[(C_1$-$C_8)$alkylene]$NHR^9$, $C(O)[(C_1$-$C_8)$alkylene]$NR^9R^9$, $CO_2R^9$, $C(S)NHR^9$, $C(S)NR^9R^9$, $SR^9$, $S(O)R^9$, $SO_2R^9$, $SO_2NHR^9$, $SO_2NR^9R^9$, $NH(CO)R^8$, $NR^9(CO)R^8$, $NH(CO)NHR^9$, $NH(CO)NR^9R^9$, $NR^9(CO)NHR^9$, $NR^9(CO)NR^9R^9$, $P(O)(OH)(OR^9)$, $P(O)(OR^9)(OR^9)$, aryl, heteroaryl, cycloalkyl or heterocyclyl.

In certain embodiments, the 5-membered heteroaryl is

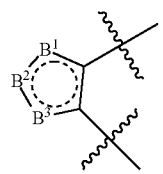

wherein any two of B¹, B² and B³ are $CR^{14}$ and N and the remaining B ring atom is $N(R^{15})$ or S, wherein $R^{14}$ is H, CN, halogen, $OR^9$, $SR^9$, ($C_1$-$C_8$)alkyl, $C(O)O(C_1$-$C_8)$alkyl, $C(O)(C_1$-$C_8)$alkyl, $SO_2(C_1$-$C_8)$alkyl, $SO_2NR^9R^9$, $C(O)NR^9R^9$, $NR^9R^9$ or $NR^9C(O)R^8$, and $R^{15}$ is H or ($C_1$-$C_8$)alkyl.

In particular embodiments, an eIF4A inhibitor compound of Formula I is selected from:

Rac-(5aR,6S,7R,8R,8aS)-8,8a-dihydroxy-3-methoxy-5a-(4-methoxyphenyl)-N,N-dimethyl-6-phenyl-5a,7,8,8a-tetrahydro-6H-cyclopenta[4,5]furo[3,2-b]pyridine-7-carboxamide (Cpd. No. 1F), (5aR,6S,7R,8R,8aS)-3-cyano-5a-(4-cyanophenyl)-8,8a-dihydroxy-N,N-dimethyl-6-phenyl-5a,7,8,8a-tetrahydro-6H-cyclopenta[4,5]furo[3,2-b]pyridine-7-carboxamide (Cpd. No. 2F), (5aR,6S,7R,8R,8aS)-3-chloro-5a-(4-cyanophenyl)-8,8a-dihydroxy-N,N-dimethyl-6-phenyl-5a,7,8,8a-tetrahydro-6H-cyclopenta[4,5]furo[3,2-b]pyridine-7-carboxamide (Cpd. No. 3F), (5aR,6S,7R,8R,8aS)-3-cyano-8,8a-dihydroxy-5a-(4-methoxyphenyl)-N,N-dimethyl-6-phenyl-5a,7,8,8a-tetrahydro-6H-cyclopenta[4,5]furo[3,2-b]pyridine-7-carboxamide (Cpd. No. 4F), (5aR,6S,7R,8R,8aS)-3-chloro-8,8a-dihydroxy-5a-(4-methoxyphenyl)-N,N-dimethyl-6-phenyl-5a,7,8,8a-tetrahydro-6H-cyclopenta[4,5]furo[3,2-b]pyridine-7-carboxamide (Cpd. No. 5F), (5aR,6S,7R,8R,8aS)-5a-(4-cyanophenyl)-8,8a-dihydroxy-3-methoxy-N,N-dimethyl-6-phenyl-5a,7,8,8a-tetrahydro-6H-cyclopenta[4,5]furo[3,2-b]pyridine-7-carboxamide (Cpd. No. 6F), (5aR,6S,7R,8R,8aS)-3-chloro-8,8a-dihydroxy-N,N-dimethyl-6-phenyl-5a-(p-tolyl)-5a,7,8,8a-tetrahydro-6H-cyclopenta[4,5]furo[3,2-b]pyridine-7-carboxamide (Cpd. No. 7F), (5aR,6S,7R,8R,8aS)-3-chloro-8,8a-dihydroxy-N,N-dimethyl-6-phenyl-5a-(4-(trifluoromethyl)phenyl)-5a,7,8,8a-tetrahydro-6H-cyclopenta[4,5]furo[3,2-b]pyridine-7-carboxamide (Cpd. No. 8F), (5aR,6S,7R,8R,8aS)-5a-(4-cyanophenyl)-8,8a-dihydroxy-N,N-dimethyl-6-phenyl-5a,7,8,8a-tetrahydro-6H-cyclopenta[4,5]furo[3,2-b]pyridine-7-carboxamide (Cpd. No. 9F), (5aR,6S,7R,8R,8aS)-3-chloro-5a-(4-fluorophenyl)-8,8a-dihydroxy-N,N-dimethyl-6-phenyl-5a,7,8,8a-tetrahydro-6H-cyclopenta[4,5]furo[3,2-b]pyridine-7-carboxamide (Cpd. No. 10F), (5aR,6S,7R,8R,8aS)-3-chloro-5a-(4-chlorophenyl)-8,8a-dihydroxy-N,N-dimethyl-6-phenyl-5a,7,8,8a-tetrahydro-6H-cyclopenta[4,5]furo[3,2-b]pyridine-7-carboxamide (Cpd. No. 11F), (5aR,6S,7R,8R,8aS)-3-chloro-8,8a-dihydroxy-N,N-dimethyl-5a-(4-(methylsulfonyl)phenyl)-6-phenyl-5a,7,8,8a-tetrahydro-6H-cyclopenta[4,5]furo[3,2-b]pyridine-7-carboxamide (Cpd. No. 12F), Rac-(1R,2R,3S,3aR,8bS)-6-cyano-3a-(4-cyanophenyl)-1,8b-dihydroxy-N,N-dimethyl-3-phenyl-2,3,3a,8b-tetrahydro-1H-benzo[b]cyclopenta[d]thiophene-2-carboxamide (Cpd. No. 13F), Rac-(5aR,6S,7R,8R,8aS)-3-cyano-5a-(4-cyanophenyl)-8,8a-dihydroxy-N,N-dimethyl-6-phenyl-5a,7,8,8a-tetrahydro-6H-cyclopenta[4,5]furo[3,2-c]pyridine-7-carboxamide (Cpd. No. 14F), Rac-(4bS,5R,6R,7S,7aR)-7a-(4-cyanophenyl)-4b,5-dihydroxy-2-methoxy-N,N-dimethyl-7-phenyl-4b,6,7,7a-tetrahydro-5H-cyclopenta[4,5]furo[2,3-b]pyridine-6-carboxamide (Cpd. No. 15F), (5aR,6S,7R,8R,8aS)-3-chloro-5a-(4-(difluoromethyl)phenyl)-8,8a-dihydroxy-N,N-dimethyl-6-phenyl-5a,7,8,8a-tetrahydro-6H-cyclopenta[4,5]furo[3,2-b]pyridine-7-carboxamide (Cpd. No. 16F), (5aR,6S,7R,8R,8aS)-3-chloro-8,8a-dihydroxy-N,N-dimethyl-6-phenyl-5a-(4-(trifluoromethoxy)phenyl)-5a,7,8,8a-tetrahydro-6H-cyclopenta[4,5]furo[3,2-b]pyridine-7-carboxamide (Cpd. No. 17F), (5aR,6S,7R,8R,8aS)-3-chloro-5a-(4-cyanophenyl)-8,8a-dihydroxy-6-phenyl-5a,7,8,8a-tetrahydro-6H-cyclopenta[4,5]furo[3,2-b]pyridine-7-carboxamide (Cpd. No. 18F), Rac-(5aR,6S,7R,8R,8aS)-5a-(4-cyanophenyl)-8,8a-dihydroxy-1-methoxy-N,N-dimethyl-6-phenyl-5a,7,8,8a-tetrahydro-6H-cyclopenta[4,5]furo[3,2-c]pyridine-7-carboxamide (Cpd. No. 19F), (5aR,6S,7R,8R,8aS)-3-chloro-5a-(4-cyanophenyl)-8,8a-dihydroxy-N-methyl-6-phenyl-5a,7,8,8a-tetrahydro-6H-cyclopenta[4,5]furo[3,2-b]pyridine-7-carboxamide (Cpd. No. 20F), Rac-methyl (4aR,5S,6R,7R,7aS)-4a-(4-cyanophenyl)-7,7a-dihydroxy-2-methyl-5-phenyl-2,4a,5,6,7,7a-hexahydrocyclopenta[4,5]furo[3,2-c]pyrazole-6-carboxylate (Cpd. No. 21F), Rac-(5aR,6S,7R,8S,8aS)-3-chloro-5a-(4-cyanophenyl)-8,8a-dihydroxy-N,N-dimethyl-6-phenyl-5a,7,8,8a-tetrahydro-6H-cyclopenta[4,5]furo[3,2-b]pyridine-7-sulfonamide (Cpd. No. 22F), (4aR,5S,6R,7R,7aS)-4a-(4-cyanophenyl)-7,7a-dihydroxy-N,N,2-trimethyl-5-phenyl-2,4a,5,6,7,7a-hexahydrocyclopenta[4,5]furo[3,2-c]pyrazole-6-carboxamide (Cpd. No. 23F), Rac-methyl (5aR,6R,6aS,7aS,7bR)-3-chloro-5a-(4-cyanophenyl)-7b-hydroxy-6-phenyl-5a,7,7a,7b-tetrahydrocyclopropa[4',5']cyclopenta[1',2':4,5]furo[3,2-b]pyridine-6a(6H)-carboxylate (Cpd. No. 24F), Rac-methyl (5aR,6R,6aS,7aS,7bR)-3-chloro-5a-(4-cyanophenyl)-7b-hydroxy-6-phenyl-5a,7,7a,7b-tetrahydrocyclopropa[4',5']cyclopenta[1',2':4,5]furo[3,2-b]pyridine-6a(6H)-carboxylate (Cpd. No. 25F), Rac-4-((5aR,6S,7R,8R,8aS)-3-chloro-8,8a-dihydroxy-7-(oxazol-2-yl)-6-phenyl-6,7,8,8a-tetrahydro-5aH-cyclopenta[4,5]furo[3,2-b]pyridin-5a-yl)benzonitrile (Cpd. No. 26F), Rac-(5aR,6S,7R,8R,8aS)-5a-(4-bromophenyl)-3-chloro-8,8a-dihydroxy-6-phenyl-5a,7,8,8a-tetrahydro-6H-cyclopenta[4,5]furo[3,2-b]pyridine-7-carbothioamide (Cpd. No. 27F), Rac-(5aR,6S,7R,8R,8aS)-5a-(4-bromophenyl)-3-chloro-8,8a-dihydroxy-6-phenyl-5a,7,8,8a-tetrahydro-6H-cyclopenta[4,5]furo[3,2-b]pyridine-7-carbothioamide (Cpd. No. 28F), Rac-(5aR,6S,7R,8R,8aS)-5a-(4-cyanophenyl)-3,8,8a-trihydroxy-N,N-dimethyl-6-phenyl-2-(trifluoromethyl)-5a,7,8,8a-tetrahydro-6H-cyclopenta[4,5]furo[3,2-b]pyridine-7-carboxamide (Cpd. No. 29F), Rac-4-((5aR,6S,7S,8R,8aS)-7-(aminomethyl)-3-chloro-8,8a-dihydroxy-6-phenyl-6,7,8,8a-tetrahydro-5aH-cyclopenta[4,5]furo[3,2-b]pyridin-5a-yl)benzonitrile (Cpd. No. 30F), Rac-(5aR,6R,6aS,7aS,7bR)-3-chloro-5a-(4-cyanophenyl)-7b-hydroxy-N,N-dimethyl-6-phenyl-5a,7,7a,7b-tetrahydrocyclopropa[4',5']cyclopenta[1',2':4,5]furo[3,2-b]pyridine-6a(6H)-carboxamide (Cpd. No. 31F), Rac-(5aR,6S,7R,8aR)-3-chloro-5a-(4-cyanophenyl)-8a-hydroxy-N,N-dimethyl-8-oxo-6-phenyl-5a,7,8,8a-tetrahydro-6H-cyclopenta[4,5]furo[3,2-b]pyridine-7-carboxamide (Cpd. No. 32F), Rac-(5aR,6S,7R,8R,8aS)-3-chloro-5a-(4-cyanophenyl)-8,8a-dihydroxy-N,N,8-trimethyl-6-phenyl-5a,7,8,8a-tetrahydro-6H-cyclopenta[4,5]furo[3,2-b]pyridine-7-carboxamide (Cpd. No. 33Fa) and Rac-(5aR,6S,7R,8S,8aS)-3-chloro-5a-(4-cyanophenyl)-8,8a-dihydroxy-N,N,8-trimethyl-6-phenyl-5a,7,8,8a-tetrahydro-6H-cyclopenta[4,5]furo[3,2-b]pyridine-7-carboxamide (Cpd. No. 33Fb), Rac-(5aR,6S,8aR)-5a-(4-bromophenyl)-3-chloro-8-methylene-6-phenyl-5a,6,7,8-tetrahydro-8aH-cyclopenta[4,5]furo[3,2-b]pyridin-8a-ol (Cpd. No. 34F), Rac-(5aR,6R,8aS)-5a-(4-bromophenyl)-3-chloro-8a-hydroxy-8-methoxy-N,N-dimethyl-6-phenyl-5a,8a-dihydro-6H-cyclopenta[4,5]furo[3,2-b]pyridine-7-carboxamide (Cpd. No. 35F), Rac-(4aR,5S,6R,7R,7aS)-3-chloro-4a-(4-cyanophenyl)-7,7a-dihydroxy-N,N,2-trimethyl-5-phenyl-2,4a,5,6,7,7a-hexahydrocyclopenta[4,5]furo[3,2-c]pyrazole-6-carboxamide (Cpd. No. 36F), Rac-(4aR,5S,6R,7R,7aS)-4a-(4-bromophenyl)-3-chloro-7,7a-dihydroxy-N,N2-trimethyl-5-phenyl-2,4a,5,6,7,7a-hexahydrocyclopenta[4,5]furo[3,2-c]pyrazole-6-carboxamide (Cpd. No. 37F), Rac-(5aR,6S,8R,8aS)-5a-(4-bromophenyl)-3-chloro-6-phenyl-6,7-dihydrospiro[cyclopenta[4,5]furo[3,2-b]pyridine-8,2'-oxetan]-8a(5aH)-ol (Cpd. No. 38F), Rac-4-((5aR,6S,7S,8R,8aS)-3-chloro-8,8a-dihydroxy-7-((methylamino)methyl)-6-phenyl-6,7,8,8a-tetrahydro-5aH-cyclopenta[4,5]furo[3,2-b]pyridin-5a-yl)benzonitrile (Cpd. No. 39F), Rac-4-((5aR,6S,7R,8R,8aS)-3-chloro-7-((dimethylamino)methyl)-8,8a-dihydroxy-6-phenyl-6,7,8,8a-tetrahydro-5aH-cyclopenta[4,5]furo[3,2-b]pyridin-5a-yl)benzonitrile (Cpd. No. 40Fa), rac-4-((5aR,6S,7S,8R,8aS)-3-chloro-7-((dimethylamino)methyl)-8,8a-dihydroxy-6-phenyl-6,7,8,8a-tetrahydro-5 aH-cyclopenta[4,5]furo[3,2-b]pyridin-5a-yl)benzonitrile (Cpd. No. 40Fb), and rac-4-((5aR,6S,7S,8S,8aS)-3-chloro-7-((dimethylamino)methyl)-8,8a-dihydroxy-6-phenyl-6,7,8,8a-tetrahydro-5aH-cyclopenta[4,5]furo[3,2-b]pyridin-5a-yl)benzonitrile (Cpd. No. 40Fc)

Rac-4-((5aR,6S,7R,8R,8aS)-3-chloro-8,8a-dihydroxy-6-phenyl-7-(pyrrolidin-1-ylmethyl)-6,7,8,8a-tetrahydro-5 aH-cyclopenta[4,5]furo[3,2-b]pyridin-5a-yl)benzonitrile (Cpd. No. 41Fa), rac-4-((5aR,6S,7S,8R,8aS)-3-chloro-8,8a-dihydroxy-6-phenyl-7-(pyrrolidin-1-ylmethyl)-6,7,8,8a-tetrahydro-5 aH-cyclopenta[4,5]furo[3,2-b]pyridin-5a-yl)benzonitrile (Cpd. No. 41Fb), and rac-4-((5aR,6S,7S,8S,8aS)-3-chloro-8,8a-dihydroxy-6-phenyl-7-(pyrrolidin-1-ylmethyl)-6,7,8,8a-tetrahydro-5 aH-cyclopenta[4,5]furo[3,2-b]pyridin-5a-yl)benzonitrile (Cpd. No. 41Fc), Rac-(1R,2R,3S,3aR,8bS)-8b-azido-1-hydroxy-6-methoxy-3a-(4-methoxyphenyl)-N,N-dimethyl-3-phenyl-2,3-dihydro-1H-cyclopenta[b]benzofuran-2-carboxamide (Cpd. No. 42F), Rac-methyl (5aR,6S,7R,8R,8aS)-5a-(4-bromophenyl)-3-chloro-8a-fluoro-8-hydroxy-6-phenyl-5a,7,8,8a-tetrahydro-6H-cyclopenta[4,5]furo[3,2-b]pyridine-7-carboxylate (Cpd. No. 43F), Rac-(1R,2R,3S,3aR,8bS)-8b-amino-1-hydroxy-6-methoxy-3a-(4-methoxyphenyl)-N,N-dimethyl-3-phenyl-2,3,3a,8b-tetrahydro-1H-cyclopenta[b]benzofuran-2-carboxamide (Cpd. No. 44F), Rac-(1R,2R,3S,3aR,8bS)-8b-acetamido-1-hydroxy-6-methoxy-3a-(4-methoxyphenyl)-N,N-dimethyl-3-phenyl-2,3,3a,8b-tetrahydro-1H-cyclopenta[b]benzofuran-2-carboxamide (Cpd. No. 45F), Rac-dimethyl 2-[[(5aR,6S,7R,8aR)-5a-(4-bromophenyl)-3-chloro-8a-hydroxy-8-oxo-6-phenyl-6,7-dihydrocyclopenta[4,5]furo[1,2-b]pyridin-7-yl]methyl]propanedioate (Cpd. No. 46F), Rac-(5aR,6S,8S,8aR)-5a-(4-bromophenyl)-3-chloro-8a-hydroxy-6-phenyl-5a,7,8,8a-tetrahydro-6H-cyclopenta[4,5]furo[3,2-b]pyridine-8-carbonitrile (Cpd. No. 47F), Rac-(5aR,6S,8aR)-5a-(4-bromophenyl)-3-chloro-8-ethynyl-6-phenyl-5a,6,7,8-tetrahydro-8aH-cyclopenta[4,5]furo[3,2-b]pyridin-8a-ol (Cpd. No. 48F), Rac-methyl (5aR,6S,7R,8R,8aR)-5a-(4-bromophenyl)-3-chloro-8-cyano-8a-hydroxy-6-phenyl-5a,7,8,8a-tetrahydro-6H-cyclopenta[4,5]furo[3,2-b]pyridine-7-carboxylate (Cpd. No. 49F), Rac-methyl (5aR,6S,7R,8R,8aR)-3-chloro-8-cyano-5a-(4-cyanophenyl)-8a-hydroxy-6-phenyl-5a,7,8,8a-tetrahydro-6H-cyclopenta[4,5]furo[3,2-b]pyridine-7-carboxylate (Cpd. No. 50F), Rac-(5aR,6S,7R,8R,8aR)-3-chloro-8-cyano-5a-(4-cyanophenyl)-8a-hydroxy-N,N-dimethyl-6-phenyl-5a,7,8,8a-tetrahydro-6H-cyclopenta[4,5]furo[3,2-b]pyridine-7-carboxamide (Cpd. No. 51F), Rac-(5aR,6S,7R,8R,8aR)-3-chloro-8-cyano-5a-(4-cyanophenyl)-8a-hydroxy-6-phenyl-5a,7,8,8a-tetrahydro-6H-cyclopenta[4,5]furo[3,2-b]pyridine-7-carboxamide (Cpd. No. 52F), Rac-(3aR,3bS,8aR,9R,9aR)-8a-(4-bromophenyl)-6-chloro-3b-hydroxy-9-phenyl-1,3a,3b,8a,9,9a-hexahydro-2H-oxazolo[4'',5'':4',5']cyclopenta[1',2':4,5]furo[3,2-b]pyridin-2-one (Cpd. No. 53F), Rac-4-((3aR,3bS,8aR,9R,9aR)-6-chloro-3b-hydroxy-2-oxo-9-phenyl-1,2,3a,3b,9,9a-hexahydro-8aH-oxazolo[4'',5'':4',5']cyclopenta[1',2':4,5]furo[3,2-b]pyridin-8a-yl)benzonitrile (Cpd. No. 54F), Rac-(5aR,6S,7S,8R,8aS)-5a-(4-bromophenyl)-3-chloro-7-(hydroxymethyl)-6-phenyl-5a,6,7,8-tetrahydro-8aH-cyclopenta[4,5]furo[3,2-b]pyridine-8,8a-diol (Cpd. No. 55F), Rac-4-((5aR,6S,7S,8R,8aS)-3-chloro-8,8a-dihydroxy-7-(hydroxymethyl)-6-phenyl-6,7,8,8a-tetrahydro-5aH-cyclopenta[4,5]furo[3,2-b]pyridin-5a-yl)benzonitrile (Cpd. No. 56F), Rac-(5aR,6S,7R,8R,8aS)-5a-(4-bromophenyl)-3-chloro-7-methyl-6-phenyl-5a,6,7,8-tetrahydro-8aH-cyclopenta[4,5]furo[3,2-b]pyridine-8,8a-diol (Cpd. No. 57F), Rac-methyl (5aR,6S,8S,8aS)-5a-(4-bromophenyl)-3-chloro-7-fluoro-8,8a-dihydroxy-6-phenyl-5a,7,8,8a-tetrahydro-6H-cyclopenta[4,5]furo[3,2-b]pyridine-7-carboxylate (Cpd. No. 58F), Rac-methyl (5aR,6S,8S,8aS)-3-chloro-5a-(4-cyanophenyl)-7-fluoro-8,8a-dihydroxy-6-phenyl-5a,7,8,8a-tetrahydro-6H-cyclopenta[4,5]furo[3,2-b]pyridine-7-carboxylate (Cpd. No. 59F), Rac-(2aS,3S,3aR,8bS,8cR)-3a-(4-bromophenyl)-6-chloro-3-phenyl-2a,3,3a,8c-tetrahydrooxeto[3'',2'':4',5']cyclopenta[1',2':4,5]furo[3,2-b]pyridin-8b(2H)-ol (Cpd. No. 60F), Rac-(2aS,3S,3aR,8bS,8cR)-3a-(4-bromophenyl)-6-chloro-3-phenyl-2a,3,3a,8c-tetrahydrooxeto[3'',2'':4',5']cyclopenta[1',2':4,5]furo[3,2-b]pyridin-8b(2H)-ol (Cpd. No. 61F), Rac-(5aR,6S,7S,8R,8aS)-5a-(4-bromophenyl)-3-chloro-7-(methoxymethyl)-6-phenyl-5a,6,7,8-tetrahydro-8aH-cyclopenta[4,5]furo[3,2-b]pyridine-8,8a-diol (Cpd. No. 62F), Rac-(1aS,3S,3aR,8bS)-3a-(4-bromophenyl)-6-chloro-3-phenyl-1a,2,3,3a-tetrahydro-oxireno[2'',3'':1',5']cyclopenta[1',2':4,5]furo[3,2-b]pyridine (Cpd. No. 63F), (4bS,5R,6R,7S,7aR)-7a-(4-Cyanophenyl)-4b,5-dihydroxy-4-methoxy-N,N-dimethyl-7-phenyl-4b,6,7,7a-tetrahydro-5H-cyclopenta[4,5]furo[2,3-c]pyridine-6-carboxamide (Cpd. No. 64F), Rac-4-((4bS,5R,6S,7S,7aR)-6-(aminomethyl)-4b,5-dihydroxy-4-methoxy-7-phenyl-5,6,7,7a-tetrahydro-4bH-cyclopenta[4,5]furo[2,3-c]pyridin-7a-yl)benzonitrile (Cpd. No. 65F), 4-((4bS,5R,6S,7S,7aR)-6-((Dimethylamino)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 66F), 4-((4bS,5R,6S,7S,7aR)-4b,5-Dihydroxy-4-methoxy-7-phenyl-6-(piperazin-1-ylmethyl)-4b,5,6,7-tetrahydro-7aH-cyclopenta[4,5]furo[2,3-c]pyridin-7a-yl)benzonitrile (Cpd. No. 67F), Rac-4-((4bS,5R,6S,7S,7aR)-4b,5-dihydroxy-4-methoxy-6-((4-methylpiperazin-1-yl)methyl)-7-phenyl-4b,5,6,7-tetrahydro-7aH-cyclopenta[4,5]furo[2,3-c]pyridin-7a-yl)benzonitrile (Cpd. No. 68F), Rac-4-((4bS,5R,6S,7S,7aR)-4b,5-dihydroxy-4-methoxy-6-((methylamino)methyl)-7-phenyl-4b,5,6,7-tetrahydro-7aH-cyclopenta[4,5]furo[2,3-c]pyridin-7a-yl)benzonitrile (Cpd. No. 69F), Rac-4-((4bS,5R,6S,7S,7aR)-6-((ethylamino)methyl)-4b,5-dihydroxy-4-methoxy-7-phenyl-4b,5,6,7-tetrahydro-7aH-cyclopenta[4,5]furo[2,3-c]pyridin-7a-yl)cyclohexa-1,3-diene-1-carbonitrile (Cpd. No. 70F), Rac-4-((4bS,5R,6S,7S,7aR)-6-(azetidin-1-ylmethyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 71F), Rac-4-((4bS,5R,6S,7S,7aR)-4b,5-dihydroxy-4-methoxy-7-phenyl-6-(pyrrolidin-1-ylmethyl)-4b,5,6,7-tetrahydro-7aH-cyclopenta[4,5]furo[2,3-c]pyridin-7a-yl)benzonitrile (Cpd. No. 72F), 4-((4bS,5R,6S,7S,7aR)-6-((Diethylamino)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 73F), Rac-4-((4bS,5R,6S,7S,7aR)-6-((ethyl(methyl)amino)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 74F), Rac-4-((4bS,5R,6S,7S,7aR)-4b,5-dihydroxy-6-(((2-hydroxyethyl)(methyl)amino)methyl)-4-methoxy-7-phenyl-4b,5,6,7-tetrahydro-7aH-cyclopenta[4,5]furo[2,3-c]pyridin-7a-yl)benzonitrile (Cpd. No. 7SF), Rac-4-((4bS,5R,6S,7S,7aR)-6-((benzyl(methyl)amino)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 76F), Rac-4-((4bS,5R,6S,7S,7aR)-6-((benzylamino)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 77F), Rac-4-((5R,6S,7S,7aR)-4b,5-dihydroxy-4-methoxy-7-phenyl-6-(((pyridin-3-ylmethyl)amino)methyl)-4b,5,6,7-tetrahydro-7aH-cyclopenta[4,5]furo[2,3-c]pyridin-7a-yl)benzonitrile (Cpd. No. 78F), Rac-4-((4bS,5R,6S,7S,7aR)-4b,5-dihydroxy-6-(((2-hydroxyethyl)amino)methyl)-4-methoxy-7-phenyl-5,6,7,7a-tetrahydro-4bH-cyclopenta[4,5]furo[2,3-c]pyridin-7a-yl)benzonitrile (Cpd. No. 79F), Rac-(4aR,5S,6R,7R,7aS)-4a-(4-cyanophenyl)-7,7a-dihydroxy-2-isopropyl-N,N-dimethyl-5-phenyl-2,4a,5,6,7,7a-hexahydrocyclopenta[4,5]furo[3,2-c]pyrazole-6-carboxamide (Cpd. No. 80F), 4-((3aR,4R,4aR,9bS,9cR)-9b-Hydroxy-9-methoxy-2-oxo-4-phenyl-2,3,3a,4,9b,9c-hexahydro-4aH-oxazolo[4'',5'':4',5']cyclopenta[1',2':4,5]furo[2,3-c]pyridin-4a-yl)benzonitrile (Cpd. No. 81F), Rac-(4aR,5S,6R,7R,7aS)-3-cyano-4a-(4-cyanophenyl)-7,7a-dihydroxy-N,N,2-trimethyl-5-phenyl-2,4a,5,6,7,7a-hexahydrocyclopenta[4,5]furo[3,2-c]pyrazole-6-carboxamide (Cpd. No. 82F), 4-((5aR,6S,7R,8S,8aS)-3-Chloro-8,8a-dihydroxy-6-phenyl-7-(pyrrolidin-1-ylsulfonyl)-6,7,8,8a-tetrahydro-5aH-cyclopenta[4,5]furo[3,2-b]pyridin-5a-yl)benzonitrile (Cpd. No. 83F), Rac-(5aR,6S,7R,8S,8aS)-5a-(4-bromophenyl)-3-chloro-7-(methyl sulfonyl)-6-phenyl-5a,6,7,8-tetrahydro-8aH-cyclopenta[4,5]furo[3,2-b]pyridine-8,8a-diol (Cpd. No. 84F), Rac-4-((5aR,6S,7R,8S,8aS)-3-chloro-8,8a-dihydroxy-7-(methyl sulfonyl)-6-phenyl-6,7,8,8a-tetrahydro-5 aH-cyclopenta[4,5]furo[3,2-b]pyridin-5a-yl)benzonitrile (Cpd. No. 85F), (5aR,6S,7R,8S,8aS)-5a-(4-Cyanophenyl)-8,8a-dihydroxy-7-(methyl sulfonyl)-6-phenyl-5a,7,8,8a-tetrahydro-6H-cyclopenta[4,5]furo[3,2-b]pyridine-3-carbonitrile (Cpd. No. 86F), Rac-((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)(morpholino)methanone (Cpd. No. 87F), Rac-(4bS,5R,6R,7S,7aR)-7a-(4-bromophenyl)-4b,5-dihydroxy-4-methoxy-N-methyl-7-phenyl-N-(2,2,2-trifluoroethyl)-4b,6,7,7a-tetrahydro-5H-cyclopenta[4,5]furo[2,3-c]pyridine-6-carboxamide (Cpd. No. 88F), Rac-(4bS,5R,6R,7S,7aR)-7a-(4-bromophenyl)-N-cyclopropyl-4b,5-dihydroxy-4-methoxy-7-phenyl-4b,6,7,7a-tetrahydro-5H-cyclopenta[4,5]furo[2,3-c]pyridine-6-carboxamide (Cpd. No. 89F), Rac-(4bS,5R,6R,7S,7aR)-7a-(4-bromophenyl)-4b,5-dihydroxy-4-methoxy-7-phenyl-N-(2,2,2-trifluoroethyl)-4b,6,7,7a-tetrahydro-5H-cyclopenta[4,5]furo[2,3-c]pyridine-6-carboxamide (Cpd. No. 90F), Rac-(5aR,6S,8S,8aS)-5a-(4-bromophenyl)-3-chloro-7,7-difluoro-6-phenyl-5a,6,7,8-tetrahydro-8aH-cyclopenta[4,5]furo[3,2-b]pyridine-8,8a-diol (Cpd. No. 91F), Rac-(5aR,6R,8R,8aS)-5a-(4-bromophenyl)-3-chloro-6-phenyl-5a,6-dihydrospiro[cyclopenta[4,5]furo[3,2-b]pyridine-7,1'-cyclopropane]-8,8a(8N)-diol (Cpd. No. 92F), Rac-(5aR,6S,7R,8S,8aS)-7-(benzylsulfonyl)-5a-(4-bromophenyl)-3-chloro-6-phenyl-5a,6,7,8-tetrahydro-8aH-cyclopenta[4,5]furo[3,2-b]pyridine-8,8a-diol (Cpd. No. 93F), Rac-4-((5aR,6S,7R,8S,8aS)-7-(benzyl sulfonyl)-3-chloro-8,8a-dihydroxy-6-phenyl-6,7,8,8a-tetrahydro-5aH-cyclopenta[4,5]furo[3,2-b]pyridin-5a-yl)benzonitrile (Cpd. No. 94F), (4bS,5R,6R,7S,7aR)-7a-(4-Cyanophenyl)-4b,5-dihydroxy-N,N-dimethyl-7-phenyl-4b,6,7,7a-tetrahydro-5H-cyclopenta[4,5]furo[2,3-c]pyridine-6-carboxamide (Cpd. No. 95F), Rac-(4bS,5R,6R,7S,7aR)-4-cyano-7a-(4-cyanophenyl)-4b,5-dihydroxy-N,N-dimethyl-7-phenyl-4b,6,7,7a-tetrahydro-5H-cyclopenta[4,5]furo[2,3-c]pyridine-6-carboxamide (Cpd. No. 96F), Rac-(4bS,5R,6R,7S,7aR)-7a-(4-bromophenyl)-4-chloro-4b,5-dihydroxy-N,N-dimethyl-7-phenyl-4b,6,7,7a-tetrahydro-5H-cyclopenta[4,5]furo[2,3-c]pyridine-6-carboxamide (Cpd. No. 97F), (4bS,5R,6R,7S,7aR)-4-Chloro-7a-(4-cyanophenyl)-4b,5-dihydroxy-N,N-dimethyl-7-phenyl-4b,6,7,7a-tetrahydro-5H-cyclopenta[4,5]furo[2,3-c]pyridine-6-carboxamide (Cpd. No. 98F), Rac-(4aR,5S,6R,7R,7aS)-4a-(4-cyanophenyl)-7,7a-dihydroxy-2-(4-methoxybenzyl)-N,N-dimethyl-5-phenyl-2,4a,5,6,7,7a-hexahydrocyclopenta[4,5]furo[3,2-c]pyrazole-6-carboxamide (Cpd. No. 99F), Rac-(4aR,5S,6R,7R,7aS)-4a-(4-cyanophenyl)-7,7a-dihydroxy-N,N-dimethyl-5-phenyl-2,4a,5,6,7,7a-hexahydrocyclopenta[4,5]furo[3,2-c]pyrazole-6-carboxamide (Cpd. No. 100F), Rac-(4bS,5S,6R,7S,7aR)-7a-(4-bromophenyl)-4-methoxy-6-(methyl sulfonyl)-7-phenyl-5,6,7,7a-tetrahydro-4bH-cyclopenta[4,5]furo[2,3-c]pyridine-4b,5-diol (Cpd. No. 101F), 4-((4bS,5S,6R,7S,7aR)-4b,5-dihydroxy-4-methoxy-6-(methylsulfonyl)-7-phenyl-4b,5,6,7-tetrahydro-7aH-cyclopenta[4,5]furo[2,3-c]pyridin-7a-yl)benzonitrile (Cpd. No. 102F), 4-((4bS,5R,6S,7S,7aR)-6-((dimethylamino)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 103F), (5aR,6S,7R,8R,8aS)-3-chloro-5a-(4-cyanophenyl)-8,8a-dihydroxy-N,N-dimethyl-6-phenyl-5a,7,8,8a-tetrahydro-6H-cyclopenta[4,5]furo[3,2-b]pyridine-7-carboxamide (Cpd. No. 104F), (5aR,6S,7S,8R,8aS)-5a-(4-cyanophenyl)-7-((dimethylamino)methyl)-8,8a-dihydroxy-6-phenyl-5a,7,8,8a-tetrahydro-6H-cyclopenta[4,5]furo[3,2-b]pyridine-3-carbonitrile (Cpd. No. 105F), (4bS,5R,6S,7S,7aR)-7a-(4-(difluoromethyl)phenyl)-6-((dimethylamino)methyl)-4-methoxy-7-phenyl-5,6,7,7a-tetrahydro-4bH-cyclopenta[4,5]furo[2,3-c]pyridine-4b,5-diol (Cpd. No. 106F), (4bS,5R,6S,7S,7aR)-6-((dimethylamino)methyl)-4-methoxy-7-phenyl-7a-(4-(trifluoromethyl)phenyl)-5,6,7,7a-tetrahydro-4bH-cyclopenta[4,5]furo[2,3-c]pyridine-4b,5-diol (Cpd. No. 107F), (5aR,6S,7R,8R,8aS)-3-chloro-5a-(4-(difluoromethyl)phenyl)-7-((dimethylamino)methyl)-6-phenyl-5a,6,7,8-tetrahydro-8aH-cyclopenta[4,5]furo[3,2-b]pyridine-8,8a-diol (Cpd. No. 108F), (5aR,6S,7S,8R,8aS)-3-chloro-7-((dimethylamino)methyl)-6-phenyl-5a-(4-(trifluoromethyl)phenyl)-5a,6,7,8-tetrahydro-8aH-cyclopenta[4,5]furo[3,2-b]pyridine-8,8a-diol (Cpd. No. 109F), 4-((4bS,5R,6S,7S,7aR)-4b,5-dihydroxy-4-methoxy-6-(morpholinomethyl)-7-phenyl-4b,5,6,7-tetrahydro-7aH-cyclopenta[4,5]furo[2,3-c]pyridin-7a-yl)benzonitrile (Cpd. No. 110F), Rac-(4bS,5R,6R,7S,7aR)-7a-(4-bromophenyl)-N-(2,2-difluoroethyl)-4b,5-dihydroxy-4-methoxy-N-methyl-7-phenyl-4b,6,7,7a-tetrahydro-5H-cyclopenta[4,5]furo[2,3-c]pyridine-6-carboxamide (Cpd. No. 111F), 4-((4bS,5R,6S,7S,7aR)-6-(((2,2-difluoroethyl)(methyl)amino)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 112F), 4-((4bS,5R,6S,7S,7aR)-6-((4,4-difluoropiperidin-1-yl)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 113F), Rac-((1R,5S)-8-azabicyclo[3.2.1]octan-8-yl)((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)methanone (Cpd. No. 114F), 4-((4bS,5R,6S,7S,7aR)-6-(((2,2-difluoroethyl)amino)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 115F), Rac-(4bS,5R,6R,7S,7aR)-7a-(4-bromophenyl)-N-(2,2-difluoroethyl)-4b,5-dihydroxy-4-methoxy-7-phenyl-4b,6,7,7a-tetrahydro-H-cyclopenta[4,5]furo[2,3-c]pyridine-6-carboxamide (Cpd. No. 116F), Rac-(4bS,5S,6R,7S,7aR)-7a-(4-bromophenyl)-4-methoxy-7-phenyl-6-((2,2,2-trifluoroethyl)sulfonyl)-5,6,7,7a-tetrahydro-4bH-cyclopenta[4,5]furo[2,3-c]pyridine-4b,5-diol (Cpd. No. 117F), Rac-4-((4bS,5S,6R,7S,7aR)-4b,5-dihydroxy-4-methoxy-7-phenyl-6-(phenylsulfonyl)-4b,5,6,7-tetrahydro-7aH-cyclopenta[4,5]furo[2,3-c]pyridin-7a-yl)benzonitrile (Cpd. No. 118F), Rac-4-((4bS,5S,6R,7S,7aR)-4b,5-dihydroxy-4-methoxy-7-phenyl-6-(pyridin-2-ylsulfonyl)-4b,5,6,7-tetrahydro-7aH-cyclopenta[4,5]furo[2,3-c]pyridin-7a-yl)benzonitrile (Cpd. No. 119F), 4-((4bR,5R,7S,7aR)-4b-hydroxy-5-(hydroxymethyl)-4-methoxy-7-phenyl-4b,5,6,7-tetrahydro-7aH-cyclopenta[4,5]furo[2,3-c]pyridin-7a-yl)benzonitrile (Cpd. No. 120F), Rac-((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)(3,3-difluoroazetidin-1-yl)methanone (Cpd. No. 121F), 4-((4bS,5R,6S,7S,7aR)-6-((3,3-difluoroazetidin-1-yl)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 122F), Rac-(5aR,6S,7R,8S,8aS)-3-chloro-5a-(4-cyanophenyl)-8,8a-dihydroxy-N-methyl-6-phenyl-5a,7,8,8a-tetrahydro-6H-cyclopenta[4,5]furo[3,2-b]pyridine-7-sulfonamide (Cpd. No. 123F), Rac-(5aR,6S,7R,8S,8aS)-5a-(4-bromophenyl)-3-chloro-8,8a-dihydroxy-N-methyl-6-phenyl-5a,7,8,8a-tetrahydro-6H-cyclopenta[4,5]furo[3,2-b]pyridine-7-sulfonamide (Cpd. No. 124F), Rac-(5aR,6S,7R,8S,8aS)-3-chloro-5a-(4-cyanophenyl)-8,8a-dihydroxy-N-methyl-6-phenyl-5a,7,8,8a-tetrahydro-6H-cyclopenta[4,5]furo[3,2-b]pyridine-7-sulfonamide (Cpd No. 125F), 4-((4bS,5S,6R,7S,7aR)-4b,5-dihydroxy-4-methoxy-6-(morpholinosulfonyl)-7-phenyl-4b,5,6,7-tetrahydro-7aH-cyclopenta[2,3-c]pyridin-7a-yl)benzonitrile (Cpd. No. 126F), Rac-(5aR,6S,8R,8aS)-5a-(4-bromophenyl)-3-chloro-6-phenyl-5a,6,7,8-tetrahydro-8aH-cyclopenta[4,5]furo[3,2-b]pyridine-8,8a-diol (Cpd. No. 127F), Rac-4-((5aR,6S,8R,8aS)-3-chloro-8,8a-dihydroxy-6-phenyl-6,7,8,8a-tetrahydro-5aH-cyclopenta[4,5]furo[3,2-b]pyridin-5a-yl)benzonitrile (Cpd. No. 128F), Rac-(5aR,6S,8aR)-5a-(4-bromophenyl)-3-chloro-8a-hydroxy-6-phenyl-5a,6,7,8a-tetrahydro-8H-cyclopenta[4,5]furo[3,2-b]pyridin-8-one (Cpd. No. 129F), Rac-(5aR,6S,8S,8aS)-5a-(4-bromophenyl)-3-chloro-6-phenyl-5a,6,7,8-tetrahydro-8aH-cyclopenta[4,5]furo[3,2-b]pyridine-8,8a-diol (Cpd. No. 130F), Rac-4-((5aR,6S,8S,8aS)-3-chloro-8,8a-dihydroxy-6-phenyl-6,7,8,8a-tetrahydro-5aH-cyclopenta[4,5]furo[3,2-b]pyridin-5a-yl)benzonitrile (Cpd. No. 131F), Rac-N'-((5aR,6S,8aS)-5a-(4-bromophenyl)-3-chloro-8a-hydroxy-6-phenyl-5a,6,7,8a-tetrahydro-8H-cyclopenta[4,5]furo[3,2-b]pyridin-8-ylidene)-4-methylbenzenesulfonohydrazide (Cpd. No. 132F), Rac-(5aR,6S,8aR)-5a-(4-bromophenyl)-3-chloro-6-phenyl-5a,6-dihydro-8aH-cyclopenta[4,5]furo[3,2-b]pyridin-8a-ol (Cpd. No. 133F), Rac-methyl (4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxylate (Cpd. No. 134F), Rac-((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)(4,4-difluoropiperidin-1-yl)methanone (Cpd. No. 135F), Rac-methyl (5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridine-7-carboxylate (Cpd. No. 136F), Rac-(5aR,6S,7R,8R,8aS)-5a-(4-bromophenyl)-3-chloro-8,8a-dihydroxy-1-methoxy-N,N-dimethyl-6-phenyl-5a,7,8,8a-tetrahydro-6H-cyclopenta[4,5]furo[3,2-c]pyridine-7-carboxamide (Cpd. No. 137F), Rac-(5aR,6S,7S,8R,8aS)-5a-(4-bromophenyl)-3-chloro-7-((dimethylamino)methyl)-1-methoxy-6-phenyl-5a,6,7,8-tetrahydro-8aH-cyclopenta[4,5]furo[3,2-c]pyridine-8,8a-diol (Cpd. No. 138F), (5aR,6S,7S,8R,8aS)-5a-(4-cyanophenyl)-7-((dimethylamino)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 139F), 4-((5aR,6S,7S,8R,8aS)-3-chloro-7-((dimethylamino)methyl)-8,8a-dihydroxy-1-methoxy-6-phenyl-6,7,8,8a-tetrahydro-5aH-cyclopenta[4,5]furo[3,2-c]pyridin-5a-yl)benzonitrile (Cpd. No. 140F), Rac-4-((5aR,6S,7S,8R,8aS)-7-((dimethylamino)methyl)-8,8a-dihydroxy-1-methoxy-6-phenyl-6,7,8,8a-tetrahydro-5aH-cyclopenta[4,5]furo[3,2-c]pyridin-5a-yl)benzonitrile (Cpd. No. 141F), Rac-(5aR,6S,7S,8R,8aS)-3-chloro-5a-(4-chlorophenyl)-7-((dimethylamino)methyl)-1-methoxy-6-phenyl-5a,6,7,8-tetrahydro-8aH-cyclopenta[4,5]furo[3,2-c]pyridine-8,8a-diol (Cpd. No. 142F), Rac-(5aR,6S,7S,8R,8aS)-3-chloro-5a-(4-(difluoromethyl)phenyl)-7-((dimethylamino)methyl)-1-methoxy-6-phenyl-5a,6,7,8-tetrahydro-8aH-cyclopenta[4,5]furo[3,2-c]pyridine-8,8a-diol (Cpd. No. 143F), Rac-(5aR,6S,7S,8R,8aS)-3-chloro-7-((dimethylamino)methyl)-1-methoxy-6-phenyl-5a-(4-(trifluoromethyl)phenyl)-5a,6,7,8-tetrahydro-8aH-cyclopenta[4,5]furo[3,2-c]pyridine-8,8a-diol (Cpd. No. 144F), (5aR,6S,7S,8R,8aS)-5a-(4-chlorophenyl)-7-((dimethylamino)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 145F), Rac-(5aR,6S,7S,8R,8aS)-5a-(4-(difluoromethyl)phenyl)-7-((dimethylamino)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 146F), (5aR,6S,7S,8R,8aS)-7-((dimethylamino)methyl)-8,8a-dihydroxy-1-methoxy-6-phenyl-5a-(4-(trifluoromethyl)phenyl)-5a,7,8,8a-tetrahydro-6H-cyclopenta[4,5]furo[3,2-c]pyridine-3-carbonitrile (Cpd. No. 147F), Rac-(5aR,6S,7S,8R,8aS)-5a-(4-(difluoromethyl)phenyl)-7-((dimethylamino)methyl)-1-methoxy-6-phenyl-5a,6,7,8-tetrahydro-8aH-cyclopenta[4,5]furo[3,2-c]pyridine-8,8a-diol (Cpd. No. 148F), Rac-(5aR,6S,7S,8R,8aS)-7-((dimethylamino)methyl)-1-methoxy-6-phenyl-5a-(4-(trifluoromethyl)phenyl)-5a,6,7,8-tetrahydro-8aH-cyclopenta[4,5]furo[3,2-c]pyridine-8,8a-diol (Cpd. No. 149F), Rac-4-((5aR,6S,7S,8R,8aS)-7-((dimethylamino)methyl)-8,8a-dihydroxy-1-methoxy-3-(methylamino)-6-phenyl-6,7,8,8a-tetrahydro-5aH-cyclopenta[4,5]furo[3,2-c]pyridin-5a-yl)benzonitrile (Cpd. No. 150F), (5aR,6S,7S,8R,8aS)-5a-(4-Cyanophenyl)-8,8a-dihydroxy-1-methoxy-7-(morpholinomethyl)-6-phenyl-5a,7,8,8a-tetrahydro-6H-cyclopenta[4,5]furo[3,2-c]pyridine-3-carbonitrile (Cpd. No. 151F), Rac-4-((5aR,6S,7S,8R,8aS)-3-chloro-8,8a-dihydroxy-1-methoxy-7-(morpholinomethyl)-6-phenyl-6,7,8,8a-tetrahydro-5 aH-cyclopenta[4,5]furo[3,2-c]pyridin-5a-yl)benzonitrile (Cpd. No. 152F), Rac-(5aR,6S,7S,8R,8aS)-5a-(4-cyanophenyl)-7-((3,3-difluoropyrrolidin-1-yl)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 153F), Rac-(5aR,6S,7S,8R,8aS)-5a-(4-cyanophenyl)-7-((3,3-difluoropiperidin-1-yl)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 154F), Rac-(5aR,6S,7S,8R,8aS)-7-((tert-butylamino)methyl)-5a-(4-cyanophenyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 155F), Rac-(5aR,6S,7S,8R,8aS)-5a-(4-bromophenyl)-7-((4-fluoropiperidin-1-yl)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 156aF), Rac-4-((5aR,6S,7S,8R,8aS)-3-chloro-7-((4-fluoropiperidin-1-yl)methyl)-8,8a-dihydroxy-1-methoxy-6-phenyl-6,7,8,8a-tetrahydro-5aH-cyclopenta[4,5]furo[3,2-c]pyridin-5a-yl)benzonitrile (Cpd. No. 156bF), Rac-(5aR,6S,7S,8R,8aS)-5a-(4-cyanophenyl)-7-((4-fluoropiperidin-1-yl)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 156cF), Rac-(5aR,6S,7S,8R,8aS)-5a-(4-bromophenyl)-7-((4,4-difluoropiperidin-1-yl)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 157aF), Rac-4-((5aR,6S,7S,8R,8aS)-3-chloro-7-((4,4-difluoropiperidin-1-yl)methyl)-8,8a-dihydroxy-1-methoxy-6-phenyl-6,7,8,8a-tetrahydro-5aH-cyclopenta[4,5]furo[3,2-c]pyridin-5a-yl)benzonitrile (Cpd. No. 157bF), Rac-(5aR,6S,7S,8R,8aS)-5a-(4-cyanophenyl)-7-((4,4-difluoropiperidin-1-yl)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 157cF), Rac-(5aR,6S,7S,8R,8aS)-5a-(4-bromophenyl)-8,8a-dihydroxy-1-methoxy-6-phenyl-7-(pyrrolidin-1-ylmethyl)-5a,7,8,8a-tetrahydro-6H-cyclopenta[4,5]furo[3,2-c]pyridine-3-carbonitrile (Cpd. No. 158aF), Rac-4-((5aR,6S,7S,8R,8aS)-3-chloro-8,8a-dihydroxy-1-methoxy-6-phenyl-7-(pyrrolidin-1-ylmethyl)-6,7,8,8a-tetrahydro-5aH-cyclopenta[4,5]furo[3,2-c]pyridin-5a-yl)benzonitrile (Cpd. No. 158bF), Rac-(5aR,6S,7S,8R,8aS)-5a-(4-cyanophenyl)-8,8a-dihydroxy-1-methoxy-6-phenyl-7-(pyrrolidin-1-ylmethyl)-5a,7,8,8a-tetrahydro-6H-cyclopenta[4,5]furo[3,2-c]pyridine-3-carbonitrile (Cpd. No. 158cF), Rac-(5aR,6S,7S,8R,8aS)-5a-(4-bromophenyl)-7-((diethylamino)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 159aF), Rac-4-((5aR,6S,7S,8R,8aS)-3-chloro-7-((diethylamino)methyl)-8,8a-dihydroxy-1-methoxy-6-phenyl-6,7,8,8a-tetrahydro-5 aH-cyclopenta[4,5]furo[3,2-c]pyridin-5a-yl)benzonitrile (Cpd. No. 159bF), Rac-(5aR,6S,7S,8R,8aS)-5a-(4-cyanophenyl)-7-((diethylamino)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 159cF), Rac-(5aR,6S,7R,8S,8aS)-5a-(4-bromophenyl)-3-chloro-6-phenyl-7-(pyridin-2-ylthio)-5a,6,7,8-tetrahydro-8aH-cyclopenta[4,5]furo[3,2-b]pyridine-8,8a-diol (Cpd. No. 160aF), Rac-(5aR,6S,7R,8S,8aS)-5a-(4-bromophenyl)-3-chloro-6-phenyl-7-(pyridin-2-ylthio)-5a,6,7,8-tetrahydro-8aH-cyclopenta[4,5]furo[3,2-b]pyridine-8,8a-diol (Cpd. No. 160bF), Rae-methyl (1 aS,2R,3S,3aR,8bS)-3a-(4-bromophenyl)-6-chloro-3-phenyl-1a,2,3,3a-tetrahydro-oxireno[2",3":1',5']cyclopenta[1',2':4,5]furo[3,2-b]pyridine-2-carboxylate (Cpd. No. 161F), Rac-(5aR,6S,8R,8aR)-5a-(4-bromophenyl)-3-chloro-8-(hydroxymethyl)-6-phenyl-5a,6,7,8-tetrahydro-8aH-cyclopenta[4,5]furo[3,2-b]pyridin-8a-ol (Cpd. No. 162F), Rac-(5aR,6S,7R,8S,8aS)-5a-(4-bromophenyl)-3-chloro-6-phenyl-7-(pyridin-2-ylsulfonyl)-5a,6,7,8-tetrahydro-8aH-cyclopenta[4,5]furo[3,2-b]pyridine-8,8a-diol (Cpd. No. 163F), Rac-4-((5aR,6S,7R,8S,8aS)-3-chloro-8,8a-dihydroxy-6-phenyl-7-(pyridin-2-ylsulfonyl)-6,7,8,8a-tetrahydro-5aH-cyclopenta[4,5]furo[3,2-b]pyridin-5a-yl)benzonitrile (Cpd. No. 164F), Rac-(5aR,6S,8S,8aR)-8-(aminomethyl)-5a-(4-bromophenyl)-3-chloro-6-phenyl-5a,6,7,8-tetra-hydro-8aH-cyclopenta[4,5]furo[3,2-b]pyridin-8a-ol (Cpd. No. 165), Rac-(5aR,6S,8S,8aR)-5a-(4-bromophenyl)-3-chloro-8-(hydroxymethyl)-6-phenyl-5a,6,7,8-tetrahydro-8aH-cyclopenta[4,5]furo[3,2-b]pyridin-8a-ol (Cpd. No. 166F), Rac-4-((5aR,6S,8R,8aR)-3-chloro-8a-hydroxy-8-(hydroxymethyl)-6-phenyl-6,7,8,8a-tetrahydro-5aH-cyclopenta[4,5]furo[3,2-b]pyridin-5a-yl)benzonitrile (Cpd. No. 167F), Rac-4-((5aR,6S,8S,8aR)-3-chloro-8a-hydroxy-8-(hydroxymethyl)-6-phenyl-6,7,8,8a-tetrahydro-5aH-cyclopenta[4,5]furo[3,2-b]pyridin-5a-yl)benzonitrile (Cpd. No. 168F), Rac-(2aR,3S,3aR,8bS,8cR)-3a-(4-bromophenyl)-6-chloro-8b-hydroxy-3-phenyl-3,3a,8b,8c-tetrahydrooxeto[3",2":4',5']cyclopenta[1',2':4,5]furo[3,2-b]pyridin-2(2aH)-one (Cpd. No. 169F), Rac-(4bR,5R,6R,7S,7aR)-5-(aminomethyl)-7a-(4-bromophenyl)-6-(hydroxymethyl)-4-methoxy-7-phenyl-5,6,7,7a-tetrahydro-4bH-cyclopenta[4,5]furo[2,3-c]pyridin-4b-ol (Cpd. No. 170F), Rac-4-((4bR,5R,6R,7S,7aR)-5-(aminomethyl)-4b-hydroxy-6-(hydroxymethyl)-4-methoxy-7-phenyl-4b,5,6,7-tetrahydro-7aH-cyclopenta[4,5]furo[2,3-c]pyridin-7a-yl)benzonitrile (Cpd. No. 171F), Rac-(4bR,5R,7S,7aR)-5-(aminomethyl)-7a-(4-bromophenyl)-4-methoxy-7-phenyl-5,6,7,7a-tetrahydro-4bH-cyclopenta[4,5]furo[2,3-c]pyridin-4b-ol (Cpd. No. 172F), Rac-4-((4bR,5R,7S,7aR)-5-(aminomethyl)-4b-hydroxy-4-methoxy-7-phenyl-4b,5,6,7-tetrahydro-7aH-cyclopenta[4,5]furo[2,3-c]pyridin-7a-yl)benzonitrile (Cpd. No. 173F), Rac-(5aR,6S,8R,8aR)-8-(aminomethyl)-5a-(4-bromophenyl)-3-chloro-6-phenyl-5a,6,7,8-tetrahydro-8aH-cyclopenta[4,5]furo[3,2-b]pyridin-8a-ol (Cpd. No. 174F), Rac-4-((5aR,6S,8R,8aR)-8-(aminomethyl)-3-chloro-8a-hydroxy-6-phenyl-6,7,8,8a-tetrahydro-5aH-cyclopenta[4,5]furo[3,2-b]pyridin-5a-yl)benzonitrile (Cpd. No. 175F), Rac-(5aR,6S,8R,8aR)-8-(aminomethyl)-5a-(4-cyanophenyl)-8a-hydroxy-6-phenyl-5a,7,8,8a-tetrahydro-6H-cyclopenta[4,5]furo[3,2-b]pyridine-3-carbonitrile (Cpd. No. 176F), Rac-(5aR,6S,8R,8aR)-5a-(4-bromophenyl)-3-chloro-8-(morpholinomethyl)-6-phenyl-5a,6,7,8-tetrahydro-8aH-cyclopenta[4,5]furo[3,2-b]pyridin-8a-ol (Cpd. No. 177F), Rac-4-((5aR,6S,8R,8aR)-3-chloro-8a-hydroxy-8-(morpholinomethyl)-6-phenyl-6,7,8,8a-tetrahydro-5aH-cyclopenta[4,5]furo[3,2-b]pyridin-5a-yl)benzonitrile (Cpd. No. 178F), Rac-(4bR,5R,6R,7S,7aR)-7a-(4-bromophenyl)-6-(hydroxymethyl)-4-methoxy-5-(morpholinomethyl)-7-phenyl-5,6,7,7a-tetrahydro-4bH-cyclopenta[4,5]furo[2,3-c]pyridin-4b-ol (Cpd. No. 179F), Rac-4-((4bR,5R,6R,7S,7aR)-4b-hydroxy-6-(hydroxymethyl)-4-methoxy-5-(morpholino-methyl)-7-phenyl-4b,5,6,7-tetrahydro-7aH-cyclopenta[4,5]furo[2,3-c]pyridin-7a-yl)benzonitrile (Cpd. No. 180F), Rac-(4bR,5R,6R,7S,7aR)-7a-(4-bromophenyl)-5-(((2,2-difluoroethyl)amino)methyl)-6-(hydroxymethyl)-4-methoxy-7-phenyl-5,6,7,7a-tetrahydro-4bH-cyclopenta[4,5]furo[2,3-c]pyridin-4b-ol (Cpd. No. 181F), Rac-4-((4bR,5R,6R,7S,7aR)-5-(((2,2-difluoroethyl)amino)methyl)-4b-hydroxy-6-(hydroxyl-methyl)-4-methoxy-7-phenyl-4b,5,6,7-tetrahydro-7aH-cyclopenta[4,5]furo[2,3-c]pyridin-7a-yl)benzonitrile (Cpd. No. 182F), Rac-(4bR,5R,6R,7S,7aR)-7a-(4-bromophenyl)-6-(hydroxymethyl)-4-methoxy-5-((4-methylpiperazin-1-yl)methyl)-7-phenyl-5,6,7,7a-tetrahydro-4bH-cyclopenta[4,5]furo[2,3-c]pyridin-4b-ol (Cpd. No. 183F), Rac-4-((4bR,5R,6R,7S,7aR)-4b-hydroxy-6-(hydroxymethyl)-4-methoxy-5-((4-methyl-piperazin-1-yl)methyl)-7-phenyl-4b,5,6,7-tetrahydro-7aH-cyclopenta[4,5]furo[2,3-c]pyridin-7a-yl)benzonitrile (Cpd. No. 184F), Rac-(4bR,5R,6R,7S,7aR)-7a-(4-bromophenyl)-6-(hydroxymethyl)-4-methoxy-5-((oxetan-3-ylamino)methyl)-7-phenyl-5,6,7,7a-tetrahydro-4bH-cyclopenta[4,5]furo[2,3-c]pyridin-4b-ol (Cpd. No. 185F), Rac-4-((4bR,5R,6R,7S,7aR)-4b-hydroxy-6-(hydroxymethyl)-4-methoxy-5-((oxetan-3-ylamino)-methyl)-7-phenyl-4b,5,6,7-tetrahydro-7aH-cyclopenta[4,5]furo[2,3-c]pyridin-7a-yl)-benzonitrile (Cpd. No. 186F), Rac-(4bR,5R,6R,7S,7aR)-7a-(4-bromophenyl)-6-(hydroxymethyl)-4-methoxy-7-phenyl-5-(((pyridin-4-ylmethyl)amino)methyl)-5,6,7,7a-tetrahydro-4bH-cyclopenta[4,5]furo[2,3-c]pyridin-4b-ol (Cpd. No. 187F), Rac-4-((4bR,5R,6R,7S,7aR)-4b-hydroxy-6-(hydroxymethyl)-4-methoxy-7-phenyl-5-(((pyridin-4-ylmethyl)amino)methyl)-4b,5,6,7-tetrahydro-7aH-cyclopenta[4,5]furo[2,3-c]pyridin-7a-yl)benzonitrile (Cpd. No. 188F), Rac-4-((5aR,6S,7R,8S,8aS)-3-chloro-8,8a-dihydroxy-6-phenyl-7-(pyridin-2-ylthio)-6,7,8,8a-tetrahydro-5aH-cyclopenta[4,5]furo[3,2-b]pyridin-5a-yl)benzonitrile (Cpd. No. 189F), Rac-(5aR,6S,8aS)-5a-(4-bromophenyl)-3-chloro-8-ethynyl-8,8a-dihydroxy-N,N-dimethyl-6-phenyl-5a,7,8,8a-tetrahydro-6H-cyclopenta[4,5]furo[3,2-b]pyridine-7-carboxamide (Cpd. No. 190F), Rac-(5aR,6S,8aS)-5a-(4-bromophenyl)-3-chloro-8,8a-dihydroxy-N,N-dimethyl-6-phenyl-8-(prop-1-yn-1-yl)-5a,7,8,8a-tetrahydro-6H-cyclopenta[4,5]furo[3,2-b]pyridine-7-carboxamide (Cpd. No. 191F), Rac-(4bR,7S,7aR)-7a-(4-bromophenyl)-4b-hydroxy-4-methoxy-N,N-dimethyl-5-oxo-7-phenyl-4b,6,7,7a-tetrahydro-5H-cyclopenta[4,5]furo[2,3-c]pyridine-6-carboxamide (Cpd. No. 192F), Rac-methyl (4bS,5R,6R,7aR)-4b,5-dihydroxy-7a-(4-iodophenyl)-4-methoxy-7-phenyl-4b,6,7,7a-tetrahydro-5H-cyclopenta[4,5]furo[2,3-c]pyridine-6-carboxylate (Cpd. No. 193F), Rac-4-((4bS,5R,6S,7S,7aR)-6-((4-acetylpiperazin-1-yl)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 194F), Rac-(5aR,6S,7S,8R,8aS)-5a-(4-bromophenyl)-3-chloro-7-(((2,2-difluoroethyl)amino)methyl)-1-methoxy-6-phenyl-5a,6,7,8-tetrahydro-8aH-cyclopenta[4,5]furo[3,2-c]pyridine-8,8a-diol (Cpd. No. 195F), Rac-4-((5aR,6S,7S,8R,8aS)-3-chloro-7-(((2,2-difluoroethyl)amino)methyl)-8,8a-dihydroxy-1-methoxy-6-phenyl-6,7,8,8a-tetrahydro-5aH-cyclopenta[4,5]furo[3,2-c]pyridin-5a-yl)benzonitrile (Cpd. No. 196F), Rac-(5aR,6S,7S,8R,8aS)-5a-(4-cyanophenyl)-7-(((2,2-difluoroethyl)amino)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 197F), 4-((5aR,6S,7S,8R,8aS)-3-chloro-8,8a-dihydroxy-1-methoxy-7-((4-methylpiperazin-1-yl)methyl)-6-phenyl-6,7,8,8a-tetrahydro-5aH-cyclopenta[4,5]furo[3,2-c]pyridin-5a-yl)benzonitrile (Cpd. No. 198aF), Rac-(5aR,6S,7S,8R,8aS)-5a-(4-cyanophenyl)-8,8a-dihydroxy-1-methoxy-7-((4-methylpiperazin-1-yl)methyl)-6-phenyl-5a,7,8,8a-tetrahydro-6H-cyclopenta[4,5]furo[3,2-c]pyridine-3-carbonitrile (Cpd. No. 198bF), Rac-(5aR,6S,7R,8R,8aR)-5a-(4-bromophenyl)-3-chloro-7-(hydroxymethyl)-1-methoxy-8-(morpholinomethyl)-6-phenyl-5a,6,7,8-tetrahydro-8aH-cyclopenta[4,5]furo[3,2-c]pyridin-8a-ol (Cpd. No. 199F), Rac-(5aR,6S,7R,8R,8aR)-5a-(4-cyanophenyl)-8a-hydroxy-7-(hydroxymethyl)-1-methoxy-8-(morpholinomethyl)-6-phenyl-5a,7,8,8a-tetrahydro-6H-cyclopenta[4,5]furo[3,2-c]pyridine-3-carbonitrile (Cpd. No. 200F), Rac-(4bR,5R,6R,7S,7aR)-5-((2-oxa-6-azaspiro[3.3]heptan-6-yl)methyl)-7a-(4-bromophenyl)-6-(hydroxymethyl)-4-methoxy-7-phenyl-5,6,7,7a-tetrahydro-4bH-cyclopenta[4,5]furo[2,3-c]pyridin-4b-ol (Cpd. No. 201F), Rac-4-((4bR,5R,6R,7S,7aR)-5-((2-oxa-6-azaspiro[3.3]heptan-6-yl)methyl)-4b-hydroxy-6-(hydroxymethyl)-4-methoxy-7-phenyl-4b,5,6,7-tetrahydro-7aH-cyclopenta[4,5]furo[2,3-c]pyridin-7a-yl)benzonitrile (Cpd. No. 202F), Rac-(4bR,5R,6R,7S,7aR)-7a-(4-bromophenyl)-6-(hydroxymethyl)-4-methoxy-5-((((1-methyl-1H-pyrazol-5-yl)methyl)amino)methyl)-7-phenyl-5,6,7,7a-tetrahydro-4bH-cyclopenta[4,5]furo[2,3-c]pyridin-4b-ol (Cpd. No. 203F), Rac-4-((4bR,5R,6R,7S,7aR)-4b-hydroxy-6-(hydroxymethyl)-4-methoxy-5-((((1-methyl-1H-pyrazol-5-yl)methyl)amino)methyl)-7-phenyl-4b,5,6,7-tetrahydro-7aH-cyclopenta[4,5]furo[2,3-c]pyridin-7a-yl)benzonitrile (Cpd. No. 204F), Rac-(4bR,5R,6R,7S,7aR)-7a-(4-bromophenyl)-5-((dimethylamino)methyl)-6-(hydroxymethyl)-4-methoxy-7-phenyl-5,6,7,7a-tetrahydro-4bH-cyclopenta[4,5]furo[2,3-c]pyridin-4b-ol (Cpd. No. 205F), Rac-4-((4bR,5R,6R,7S,7aR)-5-((dimethylamino)methyl)-4b-hydroxy-6-(hydroxymethyl)-4-methoxy-7-phenyl-4b,5,6,7-tetrahydro-7aH-cyclopenta[4,5]furo[2,3-c]pyridin-7a-yl)benzonitrile (Cpd. No. 206F), Rac-(5aR,6S,7S,8R,8aS)-5a-(4-cyanophenyl)-7-((3,3-difluoroazetidin-1-yl)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 207aF), Rac-4-((5aR,6S,7S,8R,8aS)-3-chloro-7-((3,3-difluoroazetidin-1-yl)methyl)-8,8a-dihydroxy-1-methoxy-6-phenyl-6,7,8,8a-tetrahydro-5aH-cyclopenta[4,5]furo[3,2-c]pyridin-5a-yl)benzonitrile (Cpd. No. 207bF), Rac-(5aR,6S,7S,8R,8aS)-5a-(4-cyanophenyl)-7-(((2,2-difluoroethyl)(methyl)amino)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 208aF), Rac-4-((5aR,6S,7S,8R,8aS)-3-chloro-7-(((2,2-difluoroethyl)(methyl)amino)methyl)-8,8a-dihydroxy-1-methoxy-6-phenyl-6,7,8,8a-tetrahydro-5aH-cyclopenta[4,5]furo[3,2-c]pyridin-5a-yl)benzonitrile (Cpd. No. 208bF), Rac-(5aR,6S,7R,8R,8aR)-5a-(4-bromophenyl)-3-chloro-8-((dimethylamino)methyl)-7-(hydroxymethyl)-1-methoxy-6-phenyl-5a,6,7,8-tetrahydro-8aH-cyclopenta[4,5]furo[3,2-c]pyridin-8a-ol (Cpd. No. 209F), Rac-(5aR,6S,7R,8R,8aR)-5a-(4-cyanophenyl)-8-((dimethylamino)methyl)-8a-hydroxy-7-(hydroxymethyl)-1-methoxy-6-phenyl-5a,7,8,8a-tetrahydro-6H-cyclopenta[4,5]furo[3,2-c]pyridine-3-carbonitrile (Cpd. No. 210F), Rac-(5aR,6S,7S,8R,8aS)-5a-(4-cyanophenyl)-7-((3-fluoroazetidin-1-yl)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 211aF), Rac-4-((5aR,6S,7S,8R,8aS)-3-chloro-7-((3-fluoroazetidin-1-yl)methyl)-8,8a-dihydroxy-1-methoxy-6-phenyl-6,7,8,8a-tetrahydro-5aH-cyclopenta[4,5]furo[3,2-c]pyridin-5a-yl)benzonitrile (Cpd. No. 211bF), (5aR,6S,7S,8R,8aS)-7-(Azetidin-1-ylmethyl)-5a-(4-cyanophenyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 212F), Rac-(5aR,6S,7R,8R,8aR)-5a-(4-cyanophenyl)-8-((4,4-difluoropiperidin-1-yl)methyl)-8a-hydroxy-7-(hydroxymethyl)-1-methoxy-6-phenyl-5a,7,8,8a-tetrahydro-6H-cyclopenta[4,5]furo[3,2-c]pyridine-3-carbonitrile (Cpd. No. 213F), Rac-(5aR,6S,7S,8R,8aS)-5a-(4-bromophenyl)-3-chloro-7-((3,3-dimethylmorpholino)methyl)-6-phenyl-5a,6,7,8-tetrahydro-8aH-cyclopenta[4,5]furo[3,2-b]pyridine-8,8a-diol (Cpd. No. 214F), Rac-((5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridin-7-yl)(3-(difluoromethyl)azetidin-1-yl)methanone (Cpd. No. 215F), Rac-((5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridin-7-yl)(3-(difluoromethyl)azetidin-1-yl)methanone (Cpd. No. 216F), Rac-4-((5aR,6S,7S,8R,8aS)-3-chloro-7-((3-(difluoromethyl)azetidin-1-yl)methyl)-8,8a-dihydroxy-1-methoxy-6-phenyl-6,7,8,8a-tetrahydro-5 aH-cyclopenta[4,5]furo[3,2-c]pyridin-5a-yl)benzonitrile (Cpd. No. 217F), Rac-(5aR,6S,7S,8R,8aS)-5a-(4-cyanophenyl)-7-((3-(difluoromethyl)azetidin-1-yl)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 218F), Rac-((5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridin-7-yl)(1,1-difluoro-4-azaspiro[2.3]hexan-4-yl)methanone (Cpd. No. 219F), Rac-(5aR,6S,7S,8R,8aS)-5a-(4-bromophenyl)-3-chloro-7-((1,1-difluoro-4-azaspiro[2.3]hexan-4-yl)methyl)-1-methoxy-6-phenyl-5a,6,7,8-tetrahydro-8aH-cyclopenta[4,5]furo[3,2-c]pyridine-8,8a-diol (Cpd. No. 220F), Rac-(5aR,6S,7S,8R,8aS)-5a-(4-cyanophenyl)-7-((1,1-difluoro-4-azaspiro[2.3]hexan-4-yl)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 221F), Rac-4-((5aR,6S,7S,8R,8aS)-3-chloro-7-((1,1-difluoro-4-azaspiro[2.3]hexan-4-yl)methyl)-8,8a-dihydroxy-1-methoxy-6-phenyl-6,7,8,8a-tetrahydro-5 aH-cyclopenta[4,5]furo[3,2-c]pyridin-5a-yl)benzonitrile (Cpd. No. 222F), Rac-(5aR,6S,7S,8R,8aS)-5a-(4-bromophenyl)-3-chloro-1-methoxy-7-((methylamino)methyl)-6-phenyl-5a,6,7,8-tetrahydro-8aH-cyclopenta[4,5]furo[3,2-c]pyridine-8,8a-diol (Cpd. No. 223F), Rac-4-((5aR,6S,7S,8R,8aS)-3-chloro-8,8a-dihydroxy-1-methoxy-7-((methylamino)methyl)-6-phenyl-6,7,8,8a-tetrahydro-5 aH-cyclopenta[4,5]furo[3,2-c]pyridin-5a-yl)benzonitrile (Cpd. No. 224F), Rac-(5aR,6S,7S,8R,8aS)-5a-(4-cyanophenyl)-8,8a-dihydroxy-1-methoxy-7-((methylamino)methyl)-6-phenyl-5a,7,8,8a-tetrahydro-6H-cyclopenta[4,5]furo[3,2-c]pyridine-3-carbonitrile (Cpd. No. 225F), Rac-(4bR,5R,6R,7S,7aR)-7a-(4-bromophenyl)-5-((tert-butylamino)methyl)-6-(hydroxymethyl)-4-methoxy-7-phenyl-5,6,7,7a-tetrahydro-4bH-cyclopenta[4,5]furo[2,3-c]pyridin-4b-ol (Cpd. No. 226F), Rac-(5aR,6S,7R,8S,8aR)-5a-(4-bromophenyl)-3-chloro-7-((dimethylamino)methyl)-8a-hydroxy-6-phenyl-5a,7,8,8a-tetrahydro-6H-cyclopenta[4,5]furo[3,2-b]pyridine-8-carbonitrile (Cpd. No. 227F), Rac-(5aR,6S,7R,8S,8aR)-3-chloro-5a-(4-cyanophenyl)-7-((dimethylamino)methyl)-8a-hydroxy-6-phenyl-5a,7,8,8a-tetrahydro-6H-cyclopenta[4,5]furo[3,2-b]pyridine-8-carbonitrile (Cpd. No. 228F), Rac-(5aR,6S,7R,8R,8aS)-5a-(4-bromophenyl)-8,8a-dihydroxy-1,3-dimethoxy-N,N-dimethyl-6-phenyl-5a,7,8,8a-tetrahydro-6H-cyclopenta[4,5]furo[3,2-c]pyridine-7-carboxamide (Cpd. No. 229F), Rac-(5aR,6S,7S,8R,8aS)-5a-(4-bromophenyl)-7-((dimethylamino)methyl)-1,3-dimethoxy-6-phenyl-5a,6,7,8-tetrahydro-8aH-cyclopenta[4,5]furo[3,2-c]pyridine-8,8a-diol (Cpd. No. 230F), 4-((5aR,6S,7S,8R,8aS)-7-((dimethylamino)methyl)-8,8a-dihydroxy-1,3-dimethoxy-6-phenyl-6,7,8,8a-tetrahydro-5 aH-cyclopenta[4,5]furo[3,2-c]pyridin-5a-yl)benzonitrile (Cpd. No. 231F), Rac-4-((5aR,6S,7S,8R,8aS)-7-((diethylamino)methyl)-8,8a-dihydroxy-1,3-dimethoxy-6-phenyl-6,7,8,8a-tetrahydro-5 aH-cyclopenta[4,5]furo[3,2-c]pyridin-5a-yl)benzonitrile (Cpd. No. 232F), 4-((4bS,5R,6S,7S,7aR)-4b,5-dihydroxy-4-methoxy-6-((methyl(2,2,2-trifluoroethyl)amino)methyl)-7-phenyl-4b,5,6,7-tetrahydro-7aH-cyclopenta[4,5]furo[2,3-c]pyridin-7a-yl)benzonitrile (Cpd. No. 233F), Rac-(4bR,5R,7S,7aR)-7a-(4-(aminomethyl)phenyl)-5-(hydroxymethyl)-4-methoxy-7-phenyl-5,6,7,7a-tetrahydro-4bH-cyclopenta[4,5]furo[2,3-c]pyridin-4b-ol (Cpd. No. 234F), Rac-((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)(2-oxa-6-azaspiro[3.3]heptan-6-yl)methanone (Cpd. No. 235F), Rac-4-((4bS,5R,6S,7S,7aR)-6-((2-oxa-6-azaspiro[3.3]heptan-6-yl)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 236F), Rac-(4bS,5R,6R,7S,7aR)-7a-(4-bromophenyl)-4b,5-dihydroxy-4-methoxy-N-methyl-N-(oxetan-3-yl)-7-phenyl-4b,6,7,7a-tetrahydro-5H-cyclopenta[4,5]furo[2,3-c]pyridine-6-carboxamide (Cpd. No. 237F), Rac-4-((4bS,5R,6S,7S,7aR)-4b,5-dihydroxy-4-methoxy-6-((methyl(oxetan-3-yl)amino)methyl)-7-phenyl-4b,5,6,7- tetrahydro-7aH-cyclopenta[4,5]furo[2,3-c]pyridin-7a-yl)benzonitrile (Cpd. No. 238F), Rac-(4bS,5R,6R,7S,7aR)-7a-(4-bromophenyl)-4b,5-dihydroxy-4-methoxy-N-(oxetan-3-yl)-7-phenyl-4b,6,7,7a-tetrahydro-5H-cyclopenta[4,5]furo[2,3-c]pyridine-6-carboxamide (Cpd. No. 239F), Rac-4-((4bS,5R,6S,7S,7aR)-4b,5-dihydroxy-4-methoxy-6-((oxetan-3-yl amino)methyl)-7-phenyl-4b,5,6,7-tetrahydro-7aH-cyclopenta[4,5]furo[2,3-c]pyridin-7a-yl)benzonitrile (Cpd. No. 240F), Rac-4-((4bS,5R,6S,7S,7aR)-4b,5-dihydroxy-4-methoxy-6-((((1-methyl-1H-pyrazol-5-yl)methyl)amino)methyl)-7-phenyl-4b,5,6,7-tetrahydro-7aH-cyclopenta[4,5]furo[2,3-c]pyridin-7a-yl)benzonitrile (Cpd. No. 241F), Rac-4-((4bS,5R,6S,7S,7aR)-4b,5-dihydroxy-4-methoxy-6-((((1-methyl-1H-pyrazol-5-yl)methyl)amino)methyl)-7-phenyl-4b,5,6,7-tetrahydro-7aH-cyclopenta[4,5]furo[2,3-c]pyridin-7a-yl)benzonitrile (Cpd. No. 242F), 4-((4bS,5R,6S,7S,7aR)-6-((tert-butyl(methyl)amino)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 243F), Rac-4-((4bS,5R,6S,7S,7aR)-6-((cyclopropylamino)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 244F), Rac-(4bS,5R,6R,7S,7aR)-7a-(4-bromophenyl)-N-cyclopropyl-4b,5-dihydroxy-4-methoxy-N-methyl-7-phenyl-4b,6,7,7a-tetrahydro-5H-cyclopenta[4,5]furo[2,3-c]pyridine-6-carboxamide (Cpd. No. 245F), Rac-4-((4bS,5R,6S,7S,7aR)-6-((cyclopropyl(methyl)amino)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 246F), Rac-(4bS,5R,6R,7S,7aR)-7a-(4-bromophenyl)-N-(2-fluoroethyl)-4b,5-dihydroxy-4-methoxy-N-methyl-7-phenyl-4b,6,7,7a-tetrahydro-5H-cyclopenta[4,5]furo[2,3-c]pyridine-6-carboxamide (Cpd. No. 247F), 4-((4bS,5R,6S,7S,7aR)-6-(((2-fluoroethyl)(methyl)amino)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 248F), Rac-(4bS,5R,6R,7S,7aR)-7a-(4-bromophenyl)-4b,5-dihydroxy-4-methoxy-N-methyl-N-((1-methyl-1H-pyrazol-5-yl)methyl)-7-phenyl-4b,6,7,7a-tetrahydro-5H-cyclopenta[4,5]furo[2,3-c]pyridine-6-carboxamide (Cpd. No. 249F), 4-((4bS,5R,6S,7S,7aR)-4b,5-dihydroxy-4-methoxy-6-((methyl((1-methyl-1H-pyrazol-5-yl)methyl)amino)methyl)-7-phenyl-4b,5,6,7-tetrahydro-7aH-cyclopenta[4,5]furo[2,3-c]pyridin-7a-yl)benzonitrile (Cpd. No. 250F), Rac-(4bS,5R,6R,7S,7aR)-7a-(4-bromophenyl)-4b,5-dihydroxy-N-(2-hydroxy-2-methylpropyl)-4-methoxy-N-methyl-7-phenyl-4b,6,7,7a-tetrahydro-5H-cyclopenta[4,5]furo[2,3-c]pyridine-6-carboxamide (Cpd. No. 251F), 4-((4bS,5R,6S,7S,7aR)-4b,5-dihydroxy-6-(((2-hydroxy-2-methylpropyl)(methyl)amino)methyl)-4-methoxy-7-phenyl-4b,5,6,7-tetrahydro-7aH-cyclopenta[4,5]furo[2,3-c]pyridin-7a-yl)benzonitrile (Cpd. No. 252F), Rac-(4bS,5R,6R,7S,7aR)-7a-(4-bromophenyl)-4b,5-dihydroxy-N-(2-hydroxy-2-methylpropyl)-4-methoxy-7-phenyl-4b,6,7,7a-tetrahydro-5H-cyclopenta[4,5]furo[2,3-c]pyridine-6-carboxamide (Cpd. No. 253F), 4-((4bS,5R,6S,7S,7aR)-4b,5-dihydroxy-6-(((2-hydroxy-2-methylpropyl)amino)methyl)-4-methoxy-7-phenyl-4b,5,6,7-tetrahydro-7aH-cyclopenta[4,5]furo[2,3-c]pyridin-7a-yl)benzonitrile (Cpd. No. 254F), Rac-(4bS,5R,6S,7S,7aR)-6-((dimethylamino)methyl)-4-methoxy-7-phenyl-7a-(p-tolyl)-5,6,7,7a-tetrahydro-4bH-cyclopenta[4,5]furo[2,3-c]pyridine-4b,5-diol (Cpd. No. 255F), (4bS,5R,6S,7S,7aR)-6-((dimethylamino)methyl)-4-methoxy-7-phenyl-7a-(p-tolyl)-5,6,7,7a-tetrahydro-4bH-cyclopenta[4,5]furo[2,3-c]pyridine-4b,5-diol (Cpd. No. 256F), Rac-((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)(piperidin-1-yl)methanone (Cpd. No. 257F), 4-((4bS,5R,6S,7S,7aR)-4b,5-dihydroxy-4-methoxy-7-phenyl-6-(piperidin-1-ylmethyl)-4b,5,6,7-tetrahydro-7aH-cyclopenta[4,5]furo[2,3-c]pyridin-7a-yl)benzonitrile (Cpd. No. 258F), Rac-4-((4bS,5R,6S,7S,7aR)-6-(((2-fluoroethyl)amino)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 259F), Rac-((4bS,5R,6R,7S,7aR)-7a-(4-bromophenyl)-4b,5-dihydroxy-4-methoxy-N-(2-methoxyethyl)-N-methyl-7-phenyl-4b,6,7,7a-tetrahydro-5H-cyclopenta[4,5]furo[2,3-c]pyridine-6-carboxamide (Cpd. No. 260F), 4-((4bS,5R,6S,7S,7aR)-4b,5-dihydroxy-4-methoxy-6-(((2-methoxyethyl)(methyl)amino)methyl)-7-phenyl-4b,5,6,7-tetrahydro-7aH-cyclopenta[4,5]furo[2,3-c]pyridin-7a-yl)benzonitrile (Cpd. No. 261F), Rac-(4bS,5R,6R,7S,7aR)-7a-(4-bromophenyl)-4b,5-dihydroxy-4-methoxy-N-(2-methoxyethyl)-7-phenyl-4b,6,7,7a-tetrahydro-5H-cyclopenta[4,5]furo[2,3-c]pyridine-6-carboxamide (Cpd. No. 262F), 4-((4bS,5R,6S,7S,7aR)-4b,5-dihydroxy-4-methoxy-6-(((2-methoxyethyl)amino)methyl)-7-phenyl-4b,5,6,7-tetrahydro-7aH-cyclopenta[4,5]furo[2,3-c]pyridin-7a-yl)benzonitrile hydrochloride (Cpd. No. 263F), Rac-((1R,5S)-3-oxa-8-azabicyclo[3.2.1]octan-8-yl)((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)methanone (Cpd. No. 264F), 4-((4bS,5R,6S,7S,7aR)-6-(((1R,5S)-3-oxa-8-azabicyclo[3.2.1]octan-8-yl) methyl)-4b,5-dihydroxy-4-methoxy-7-phenyl-4b,5,6,7-tetrahydro-7aH-cyclopenta [4,5]furo[2,3-c]pyridin-7a-yl)benzonitrile (Cpd. No. 265F), Rac-((1R,5S)-3-oxa-6-azabicyclo[3.1.1]heptan-6-yl)((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)methanone (Cpd. No. 266F), Rac-4-((4bS,5R,6S,7S,7aR)-6-(((1R,5S)-3-oxa-6-azabicyclo[3.1.1]heptan-6-yl)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 267F), 4-((4bS,5R,6S,7S,7aR)-6-(((1R,5S)-8-azabicyclo[3.2.1]octan-8-yl)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 268F), Rac-(3aR,4R,4aR,9bS,9cR)-4a-(4-(difluoromethyl)phenyl)-9b-hydroxy-9-methoxy-4-phenyl-3,3a,4,4a,9b,9c-hexahydro-2H-oxazolo[4'',5'':4',5']cyclopenta[1',2':4,5]furo[2,3-c]pyridin-2-one (Cpd. No. 269F), Rac-(4bS,5R,6R,7R,7aR)-6-amino-7a-(4-(difluoromethyl)phenyl)-4-methoxy-7-phenyl-5,6,7,7a-tetrahydro-4bH-cyclopenta[4,5]furo[2,3-c]pyridine-4b,5-diol (Cpd. No. 270F), Rac-((4bS,5R,6R,7S,7aR)-7a-(4-chlorophenyl)-4b,5-dihydroxy-4-methoxy-N,N-dimethyl-7-phenyl-4b,6,7,7a-tetrahydro-5H-cyclopenta[4,5]furo[2,3-c]pyridine-6-carboxamide (Cpd. No. 271F), (4bS,5R,6S,7S,7aR)-7a-(4-Chlorophenyl)-6-((dimethylamino)methyl)-4-methoxy-7-phenyl-5,6,7,7a-tetrahydro-4bH-cyclopenta[4,5]furo[2,3-c]pyridine-4b,5-diol (Cpd. No. 272F), Rac-(6-oxa-3-azabicyclo[3.1.1]heptan-3-yl)((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)methanone (Cpd. No. 273F), 4-((4bS,5R,6S,7S,7aR)-6-((6-oxa-3-azabicyclo[3.1.1]heptan-3-yl)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 274F), Rac-(3aR,4S,4aR,9bS,9cR)-4a-(4-bromophenyl)-9b-hydroxy-9-methoxy-4-phenyl-3,3a,4,4a,9b,9c-hexahydro-2H-furo[3",2":4',5']cyclopenta[1',2':4,5]furo[2,3-c]pyridin-2-one (Cpd. No. 275F), Rac-4-((4bS,5R,6R,7S,7aR)-6-(2-(dimethylamino)ethyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 276F), Rac-(4bS,5R,6R,7S,7aR)-7a-(4-bromophenyl)-4b,5-dihydroxy-4-methoxy-N-methyl-7-phenyl-N-(pyridin-3-ylmethyl)-4b,6,7,7a-tetrahydro-5H-cyclopenta[4,5]furo[2,3-c]pyridine-6-carboxamide (Cpd. No. 277F), 4-((4bS,5R,6S,7S,7aR)-4b,5-dihydroxy-4-methoxy-6-((methyl(pyridin-3-ylmethyl)amino)methyl)-7-phenyl-4b,5,6,7-tetrahydro-7aH-cyclopenta[4,5]furo[2,3-c]pyridin-7a-yl)benzonitrile (Cpd. No. 278F), Rac-((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)(3,3-difluoropyrrolidin-1-yl)methanone (Cpd. No. 279F), 4-((4bS,5R,6S,7S,7aR)-6-((3,3-difluoropyrrolidin-1-yl)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 280F), Rac-((4bS,5R,6R,7S,7aR)-4b,5-dihydroxy-4-methoxy-7-phenyl-7a-(4-(trifluoromethyl)phenyl)-4b,6,7,7a-tetrahydro-5H-cyclopenta[4,5]furo[2,3-c]pyridin-6-yl)(morpholino)methanone (Cpd. No. 281F), (4bS,5R,6S,7S,7aR)-4-Methoxy-6-(morpholinomethyl)-7-phenyl-7a-(4-(trifluoromethyl)phenyl)-5,6,7,7a-tetrahydro-4bH-cyclopenta[4,5]furo[2,3-c]pyridine-4b,5-diol (Cpd. No. 282F), Rac-(4bS,5R,6S,7S,7aR)-4-methoxy-6-((4-methylpiperazin-1-yl)methyl)-7-phenyl-7a-(4-(trifluoromethyl)phenyl)-5,6,7,7a-tetrahydro-4bH-cyclopenta[4,5]furo[2,3-c]pyridine-4b,5-diol (Cpd. No. 283F), (4bS,5R,6S,7S,7aR)-4-Methoxy-6-((4-methylpiperazin-1-yl)methyl)-7-phenyl-7a-(4-(trifluoromethyl)phenyl)-5,6,7,7a-tetrahydro-4bH-cyclopenta[4,5]furo[2,3-c]pyridine-4b,5-diol (Cpd. No. 284F), Rac-(4bS,5R,6R,7S,7aR)—N-(2,2-difluoroethyl)-4b,5-dihydroxy-4-methoxy-7-phenyl-7a-(4-(trifluoromethyl)phenyl)-4b,6,7,7a-tetrahydro-5H-cyclopenta[4,5]furo[2,3-c]pyridine-6-carboxamide (Cpd. No. 285F), (4bS,5R,6S,7S,7aR)-6-(((2,2-Difluoroethyl)amino)methyl)-4-methoxy-7-phenyl-7a-(4-(trifluoromethyl)phenyl)-5,6,7,7a-tetrahydro-4bH-cyclopenta[4,5]furo[2,3-c]pyridine-4b,5-diol (Cpd. No. 286F), Rac-4-((4bS,5R,7S,7aR)-4b,5-dihydroxy-4-methoxy-5-(morpholinomethyl)-7-phenyl-4b,5,6,7-tetrahydro-7aH-cyclopenta[4,5]furo[2,3-c]pyridin-7a-yl)benzonitrile (Cpd. No. 287F), (5aR,6S,7S,8R,8aS)-5a-(4-Cyanophenyl)-7-((3,3-difluoroazetidin-1-yl)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 288F), Rac-(4bR,7S,7aR)-4-methoxy-5-(morpholinomethyl)-7-phenyl-7a-(4-(trifluoromethyl)phenyl)-5,6,7,7a-tetrahydro-4bH-cyclopenta[4,5]furo[2,3-c]pyridin-4b-ol (Cpd. No. 289F), 4-((4bS,5R,6S,7S,7aR)-6-((tert-butylamino)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 290F), 4-((4bS,5R,6S,7S,7aR)-4b,5-dihydroxy-4-methoxy-7-phenyl-6-(((2,2,2-trifluoroethyl)amino)methyl)-4b,5,6,7-tetrahydro-7aH-cyclopenta[4,5]furo[2,3-c]pyridin-7a-yl)benzonitrile (Cpd. No. 291F), Rac-(5aR,6S,7S,8R,8aS)-7-(aminomethyl)-5a-(4-bromophenyl)-3-chloro-1-methoxy-6-phenyl-5a,6,7,8-tetrahydro-8aH-cyclopenta[4,5]furo[3,2-c]pyridine-8,8a-diol (Cpd. No. 292F), Rac-(5aR,6S,7S,8R,8aS)-7-(aminomethyl)-5a-(4-cyanophenyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 293F), Rac-4-((5aR,6S,7S,8R,8aS)-7-(aminomethyl)-3-chloro-8,8a-dihydroxy-1-methoxy-6-phenyl-6,7,8,8a-tetrahydro-5aH-cyclopenta[4,5]furo[3,2-c]pyridin-5a-yl)benzonitrile (Cpd. No. 294F), and Rac-(5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridine-7-carboxylic acid (Cpd. No. 295F).

In certain embodiments, the compounds according to Formula I are selected from (5aR,6S,7S,8R,8aS)-7-((Dimethylamino)methyl)-8,8a-dihydroxy-methoxy-6-phenyl-5a-(4-(trifluoromethyl)phenyl)-5a,7,8,8a-tetrahydro-6H-cyclopenta[4,5]furo[3,2-c]pyridine-3-carbonitrile (Cpd. No. 147F), 4-((5aR,6S,7S,8R,8aS)-3-Chloro-8,8a-dihydroxy-1-methoxy-7-((4-methylpiperazin-1-yl)methyl)-6-phenyl-6,7,8,8a-tetrahydro-5 aH-cyclopenta[4,5]furo[3,2-c]pyridin-5a-yl)benzonitrile (Cpd. No. 198aF), (5aR,6S,7S,8R,8aS)-7-(Azetidin-1-ylmethyl)-5a-(4-cyanophenyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 212F), (5aR,6S,7S,8R,8aS)-5a-(4-Chlorophenyl)-7-((dimethylamino)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 145F), Rac-(5aR,6S,7S,8R,8aS)-3-chloro-7-((dimethylamino)methyl)-1-methoxy-6-phenyl-5a-(4-(trifluoromethyl)phenyl)-5a,6,7,8-tetrahydro-8aH-cyclopenta[4,5]furo[3,2-c]pyridine-8,8a-diol (Cpd. No. 144F), Rac-(5aR,6S,7S,8R,8aS)-3-chloro-5a-(4-(difluoromethyl)phenyl)-7-((dimethylamino)methyl)-1-methoxy-6-phenyl-5a,6,7,8-tetrahydro-8aH-cyclopenta[4,5]furo[3,2-c]pyridine-8,8a-diol (Cpd. No. 143F), Rac-(5aR,6S,7S,8R,8aS)-3-chloro-5a-(4-chlorophenyl)-7-((dimethylamino)methyl)-1-methoxy-6-phenyl-5a,6,7,8-tetrahydro-8aH-cyclopenta[4,5]furo[3,2-c]pyridine-8,8a-diol (Cpd. No. 142F), Rac-4-((5aR,6S,7S,8R,8aS)-3-chloro-7-(((2,2-difluoro-ethyl)amino)methyl)-8,8a-dihydroxy-1-methoxy-6-phenyl-6,7,8,8a-tetrahydro-5aH-cyclopenta[4,5]furo[3,2-c]pyridin-5a-yl)benzonitrile (Cpd. No. 196F),
(5aR,6S,7S,8R,8aS)-5a-(4-Cyanophenyl)-7-((dimethyl-amino)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 139F),
Rac-4-((5aR,6S,7S,8R,8aS)-3-chloro-7-((3,3-difluoroazetidin-1-yl)methyl)-8,8a-dihydroxy-1-methoxy-6-phenyl-6,7,8,8a-tetrahydro-5aH-cyclopenta[4,5]furo[3,2-c]pyridin-5a-yl)benzonitrile (Cpd. No. 207bF),
Rac-4-((5aR,6S,7S,8R,8aS)-3-chloro-8,8a-dihydroxy-1-methoxy-7-(morpholinomethyl)-6-phenyl-6,7,8,8a-tetrahydro-5aH-cyclopenta[4,5]furo[3,2-c]pyridin-5a-yl)benzonitrile (Cpd. No. 152F),
Rac-4-((5aR,6S,7S,8R,8aS)-3-chloro-7-((4,4-difluoropiperidin-1-yl)methyl)-8,8a-dihydroxy-1-methoxy-6-phenyl-6,7,8,8a-tetrahydro-5aH-cyclopenta[4,5]furo[3,2-c]pyridin-5a-yl)benzonitrile (Cpd. No. 157bF),
Rac-4-((5aR,6S,7S,8R,8aS)-3-chloro-8,8a-dihydroxy-1-methoxy-6-phenyl-7-(pyrrolidin-1-ylmethyl)-6,7,8,8a-tetrahydro-5aH-cyclopenta[4,5]furo[3,2-c]pyridin-5a-yl)benzonitrile (Cpd. No. 158bF),
4-((5aR,6S,7S,8R,8aS)-7-((Dimethylamino)methyl)-8,8a-dihydroxy-1,3-dimethoxy-6-phenyl-6,7,8,8a-tetrahydro-5aH-cyclopenta[4,5]furo[3,2-c]pyridin-5a-yl)benzonitrile (Cpd. No. 231F),
Rac-4-((5aR,6S,7S,8R,8aS)-3-chloro-7-((diethylamino)methyl)-8,8a-dihydroxy-1-methoxy-6-phenyl-6,7,8,8a-tetrahydro-5 aH-cyclopenta[4,5]furo[3,2-c]pyridin-5a-yl)benzonitrile (Cpd. No. 159bF),
4-((5aR,6S,7S,8R,8aS)-3-Chloro-7-((dimethylamino)methyl)-8,8a-dihydroxy-1-methoxy-6-phenyl-6,7,8,8a-tetrahydro-5aH-cyclopenta[4,5]furo[3,2-c]pyridin-5a-yl)benzonitrile (Cpd. No. 140F),
Rac-(5aR,6S,7S,8R,8aS)-5a-(4-(difluoromethyl)phenyl)-7-((dimethylamino)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 146F),
(5aR,6S,7S,8R,8aS)-5a-(4-Cyanophenyl)-8,8a-dihydroxy-1-methoxy-7-(morpholinomethyl)-6-phenyl-5a,7,8,8a-tetrahydro-6H-cyclopenta[4,5]furo[3,2-c]pyridine-3-carbonitrile (Cpd. No. 151F),
Rac-(5aR,6S,7S,8R,8aS)-5a-(4-cyanophenyl)-7-(((2,2-difluoroethyl)amino)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 197F),
Rac-(5aR,6S,7S,8R,8aS)-5a-(4-cyanophenyl)-7-((3,3-difluoroazetidin-1-yl)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 207aF),
Rac-(5aR,6S,7S,8R,8aS)-5a-(4-cyanophenyl)-7-((4,4-difluoropiperidin-1-yl)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 157cF),
Rac-(5aR,6S,7S,8R,8aS)-5a-(4-cyanophenyl)-7-((3,3-difluoropyrrolidin-1-yl)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 153F),
Rac-(5aR,6S,7S,8R,8aS)-5a-(4-cyanophenyl)-7-((diethylamino)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 159cF),
Rac-(5aR,6S,7S,8R,8aS)-5a-(4-cyanophenyl)-8,8a-dihydroxy-1-methoxy-6-phenyl-7-(pyrrolidin-1-ylmethyl)-5a,7,8,8a-tetrahydro-6H-cyclopenta[4,5]furo[3,2-c]pyridine-3-carbonitrile (Cpd. No. 158cF),
Rac-4-((4bR,5R,6R,7S,7aR)-4b-hydroxy-6-(hydroxymethyl)-4-methoxy-5-(morpholino-methyl)-7-phenyl-4b,5,6,7-tetrahydro-7aH-cyclopenta[4,5]furo[2,3-c]pyridin-7a-yl)benzonitrile (Cpd. No. 180F),
Rac-4-((4bR,5R,6R,7S,7aR)-5-((dimethylamino)methyl)-4b-hydroxy-6-(hydroxymethyl)-4-methoxy-7-phenyl-4b,5,6,7-tetrahydro-7aH-cyclopenta[4,5]furo[2,3-c]pyridin-7a-yl)benzonitrile (Cpd. No. 206F),
4-((4bS,5R,6S,7S,7aR)-6-((Dimethylamino)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 66F),
(4bS,5R,6S,7S,7aR)-7a-(4-Chlorophenyl)-6-((dimethylamino)methyl)-4-methoxy-7-phenyl-5,6,7,7a-tetrahydro-4bH-cyclopenta[4,5]furo[2,3-c]pyridine-4b,5-diol (Cpd. No. 272F),
(4bS,5R,6S,7S,7aR)-7a-(4-(Difluoromethyl)phenyl)-6-((dimethylamino)methyl)-4-methoxy-7-phenyl-5,6,7,7a-tetrahydro-4bH-cyclopenta[4,5]furo[2,3-c]pyridine-4b,5-diol (Cpd. No. 106F), and
(4bS,5R,6S,7S,7aR)-6-((Dimethylamino)methyl)-4-methoxy-7-phenyl-7a-(4-(trifluoromethyl)phenyl)-5,6,7,7a-tetrahydro-4bH-cyclopenta[4,5]furo[2,3-c]pyridine-4b,5-diol (Cpd. No. 107F).

Cpd. No. 232F, which is referred to as "Cmp1" in the Examples, has the following structure:

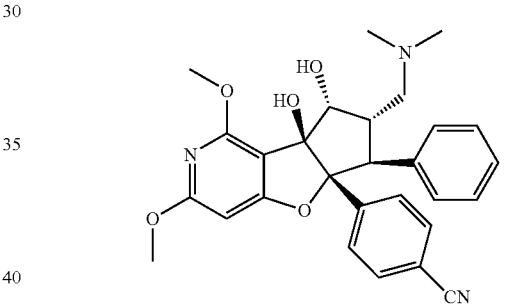

Cpd. No. 140F, which is referred to as "Cmp2" in the Examples, has the following structure:

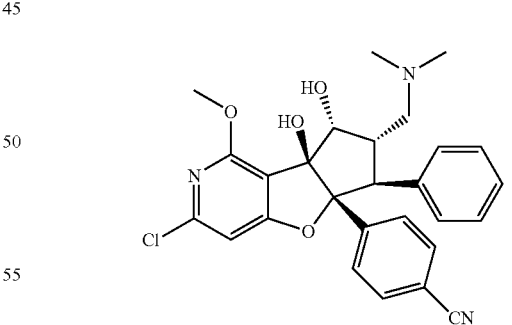

Further examples of site-directed eIF4A inhibitors include compounds as disclosed in PCT Application No. PCT/US2016/063353, which compounds and synthetic methods disclosed therein are incorporated herein by reference in their entirety.

Compounds according to Formula I may be isotopically labeled by having one or more atoms replaced by an atom having a different atomic mass or mass number. Examples of isotopes that can be incorporated into compounds of according to Formula I include isotopes of hydrogen, carbon, nitrogen, oxygen, phosphorous, fluorine, chlorine, or iodine. Illustrative of such isotopes are $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively. These radiolabeled compounds can be used to measure the biodistribution, tissue concentration and the kinetics of transport and excretion from biological tissues including a subject to which such a labeled compound is administered. Labeled compounds are also used to determine therapeutic effectiveness, the site or mode of action, and the binding affinity of a candidate therapeutic to a pharmacologically important target. Certain radioactive-labeled compounds according to Formula I, therefore, are useful in drug and/or tissue distribution studies. The radioactive isotopes tritium, i.e., $^3$H, and carbon-14, i.e., $^{14}$C, are particularly useful for this purpose in view of their ease of incorporation and ready means of detection.

Substitution with heavier isotopes such as deuterium, i.e., $^2$H, affords certain therapeutic advantages resulting from the greater metabolic stability, for example, increased in vivo half-life of compounds containing deuterium. Substitution of hydrogen with deuterium may reduce dose required for therapeutic effect, and hence may be preferred in a discovery or clinical setting.

Substitution with positron-emitting isotopes, such as $^{11}$C, $^{18}$F, $^{15}$O and $^{13}$N, provides labeled analogs of presently disclosed compounds that are useful in Positron Emission Tomography (PET) studies, e.g., for examining substrate receptor occupancy. Isotopically labeled compounds according to Formula I, can generally be prepared by techniques or processes analogous to those described in the Preparations and Examples section as set out below using an appropriate isotopic-labeling reagent.

In certain embodiments, methods disclosed herein also encompass use or activity of in vivo metabolic products of compounds according to Formula I. Such products may result from, for example, the oxidation, reduction, hydrolysis, amidation, esterification, and like processes primarily due to enzymatic activity upon administration of a compound of the invention. Accordingly, in certain embodiments, the presently disclosed methods include use of compounds that are produced as by-products of enzymatic or non-enzymatic activity on an eIF4A inhibitor following the administration of such a compound to a mammal for a period of time sufficient to yield a metabolic product. Metabolic products, particularly pharmaceutically active metabolites, are typically identified by administering a radiolabeled compound of the present disclosure in a detectable dose to a subject, such as rat, mouse, guinea pig, monkey, or human, for a sufficient period of time during which metabolism occurs, and isolating the metabolic products from urine, blood or other biological samples that are obtained from the subject receiving the radiolabeled compound.

In some embodiments, the methods disclosed herein also provide use of pharmaceutically acceptable salt forms of eIF4A inhibitors such as Formula I compounds. Encompassed within the scope of this disclosure are uses of both acid and base addition salts that are formed by contacting a pharmaceutically suitable acid or a pharmaceutically suitable base with an eIF4A inhibitor.

To this end, a "pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

Similarly, a "pharmaceutically acceptable base addition salt" refers to those salts which retain the biological effectiveness and properties of the free acids, which are not biologically or otherwise undesirable. These salts are prepared by addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often, crystallizations produce a solvate of the compound for use in the disclosed methods. As used herein, the term "solvate" refers to an aggregate that comprises one or more molecules of a compound of the present disclosure with one or more molecules of solvent. The solvent may be water, in which case the solvate may be a hydrate. Alternatively, the solvent may be an organic solvent. Thus, an eIF4A inhibitor for use in the presently disclosed methods may exist as a hydrate, including a monohydrate, dihydrate, hemihydrate, sesquihydrate, trihydrate, tetrahydrate and the like, as well as the corresponding solvated forms. A compound for use in methods of the present disclosure may be a true solvate, or may merely retain adventitious water or may be a mixture of water plus some adventitious solvent. A "stereoisomer" refers to a compound made up of the same atoms bonded by the same bonds but having different three-dimensional structures, which are not interchangeable. The present disclosure contemplates various stereoisomers and mixtures thereof and includes "enantiomers", which refers to two stereoisomers whose molecules are non-superimposable mirror images of one another.

Compounds or their pharmaceutically acceptable salts for use in the presently disclosed methods may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present disclosure is meant to include all such possible isomers, as well as their racemic and optically pure forms. Optically active (+) and (−), (R)- and (S)-, or (D)- and (L)-isomers may be prepared using chiral synthons or chiral reagents, or resolved using, for example, chromatography and fractional crystallization. Techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When compounds described herein contain olefinic double bonds or other centers of geometric asymmetry, and unless specified otherwise, it is intended that the compounds include both E and Z geometric isomers. Likewise, all tautomeric forms are also intended to be included. The term "tautomer" refers to a proton shift from one atom of a molecule to another atom of the same molecule.

Site-directed eIF4A inhibitors may be synthesized using synthetic methods, and more specifically may be synthesized using methods disclosed in PCT Application No. PCT/US2016/063353.

It will also be appreciated by those of skill in the art, although such protected derivatives of compounds of this disclosure may not possess pharmacological activity as such, they may be administered to a mammal and thereafter metabolized in the body to form compounds of this disclosure that are pharmacologically active. Such protected derivatives may, therefore, be described as "prodrugs." In certain embodiments, compounds of this disclosure are in the form of a prodrug.

In certain embodiments, eIF4A inhibitors are formulated as pharmaceutically acceptable compositions that contain an eIF4A inhibitor in an amount effective to inhibit eIF4A activity in a non-inflamed solid tumor in a subject. Pharmaceutical compositions for use in methods of the present disclosure can comprise an eIF4A inhibitor in combination with a pharmaceutically acceptable carrier, diluent or excipient.

In this regard, a "pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

Further, a "mammal" includes humans and both domestic animals such as laboratory animals and household pets (e.g., cats, dogs, swine, cattle, sheep, goats, horses, rabbits), and non-domestic animals such as wildlife and the like.

Pharmaceutical compositions disclosed herein can be prepared by combining an eIF4A inhibitor with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Exemplary routes of administering such pharmaceutical compositions include, without limitation, oral, topical, transdermal, inhalation, parenteral, sublingual, buccal, intratumoral, rectal, vaginal, and intranasal. The term "parenteral" as used herein includes subcutaneous injections, intravenous, intramuscular, intrasternal injection or infusion techniques. Pharmaceutical compositions for use in the presently disclosed methods are formulated so as to allow the active ingredients contained therein to be bioavailable upon administration of the composition to a subject. Pharmaceutical compositions that will be administered to a subject may take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see Remington: *The Science and Practice of Pharmacy*, 20th Edition (Philadelphia College of Pharmacy and Science, 2000). The composition to be administered will, in any event, contain a therapeutically effective amount of an eIF4A inhibitor as described herein, or a pharmaceutically acceptable salt thereof, for use in a method as described herein.

A pharmaceutical composition for use in the present methods may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, for example, inhalatory administration. When intended for oral administration, a pharmaceutical composition is preferably in either solid or liquid form, where semi-solid, semi-liquid, suspension and gel forms are included within the forms considered herein as either solid or liquid.

As a solid composition for oral administration, a pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example, a gelatin capsule, it may contain, in addition to materials of the above type, a liquid carrier such as polyethylene glycol or oil.

A pharmaceutical composition may be in the form of a liquid, for example, an elixir, syrup, solution, emulsion or suspension. The liquid may be for oral administration or for delivery by injection, as two examples. When intended for oral administration, a composition may contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

Liquid pharmaceutical compositions, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition intended for either parenteral or oral administration in a method of this disclosure should contain an amount of a compound of the invention such that a suitable dosage will be obtained.

A pharmaceutical composition may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device.

A pharmaceutical composition may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

A pharmaceutical composition may include various materials that modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

A pharmaceutical composition in solid or liquid form may include an agent that binds to the compound of the invention and thereby assists in the delivery of the compound. Suitable agents that may act in this capacity include a monoclonal or polyclonal antibody, a protein or a liposome.

A pharmaceutical composition may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation, may determine preferred aerosols.

Pharmaceutical compositions may be prepared by any methodology well known in the pharmaceutical art. For example, a pharmaceutical composition intended to be administered by injection can be prepared by combining a compound of the invention with sterile, distilled water so as to form a solution. A surfactant may be added to facilitate the formation of a homogeneous solution or suspension. Surfactants are compounds that non-covalently interact with the compound of the invention so as to facilitate dissolution or homogeneous suspension of the compound in the aqueous delivery system.

eIF4A inhibitors and pharmaceutical compositions of this disclosure may also be useful for the manufacture of a medicament for treating a non-inflamed solid tumor or a related cancer, e.g., by promoting or stimulating infiltration of antitumor lymphocytes.

Antitumor Lymphocytes

In certain embodiments, the present disclosure provides methods for treating a hyperproliferative disorder, such as cancer, comprising administering an eIF4A inhibitor to promote infiltration of antitumor lymphocytes into a non-inflamed solid tumor. As used herein, the term "antitumor lymphocyte" refers to a white blood cell that has antitumor activity. Antitumor activity can include, for example, preventing or slowing the growth of or causing regression of a tumor, cytotoxic activity resulting in the death of a tumor cell, or reducing the ability of a tumor cell to grow, migrate, divide, metabolize nutrients, or send signals to or receive signals from other cells. Antitumor lymphocytes include, for example, tumor antigen-specific T cells, including $CD8^+$ ("effector") T cells and $CD4^+$ ("helper") T cells, natural killer (NK) cells, natural killer T cells (NK-T cells), B cells, and plasma cells.

A "T cell" is a cell of the adaptive immune system that matures in the thymus and produces T cell receptors (TCRs). As used herein, "T cell receptor" (TCR) refers to a molecule found on the surface of T cells and NK-T cells that, in association with CD3, is generally responsible for recognizing antigens bound to MHC (HLA) molecules. The TCR has a disulfide-linked heterodimer of the highly variable α and β chains (also known as TCRα and TCRβ, respectively) in most T cells. In a subset of T cells, a TCR is made up of a heterodimer of variable γ and δ chains (also known as TCRγ and TCR δ, respectively). Each chain of the TCR is a member of the immunoglobulin superfamily and possesses one N-terminal immunoglobulin variable domain, one immunoglobulin constant domain, a transmembrane region, and a short cytoplasmic tail at the C-terminal end (see Janeway et al., *Immunobiology: The Immune System in Health and Disease*, 3rd Ed., Current Biology Publications, p. 4:33, 1997). In the case of NK cells, the receptor comprises an NK-receptor. NK-receptors include both activating receptors (Ly49 activating receptors, NKR, CD94:NKG2 heterodimers, and CD16 (FcγRIII)) and inhibitory receptors (killer-cell immunoglobulin-like receptors, leukocyte inhibitory receptors, and inhibitory Ly49receptors). TCRs recognize antigens presented by MHC/HLA complexes on antigen presenting cells (APCs) to initiate cytotoxic immune responses. T cells can be naïve (not exposed to antigen; increased expression of CD62L, CCR7, CD28, CD3, CD127, and CD45RA, and decreased expression of CD45RO as compared to $T_{CM}$), memory T cells ($T_M$) (antigen-experienced and long-lived), and effector cells (antigen-experienced, cytotoxic). $T_M$ can be further divided into subsets of central memory T cells ($T_{CM}$, increased expression of CD62L, CCR7, CD28, CD127, CD45RO, and CD95, and decreased expression of CD54RA as compared to naïve T cells) and effector memory T cells ($T_{EM}$, decreased expression of CD62L, CCR7, CD28, CD45RA, and increased expression of CD127 as compared to naïve T cells or $T_{CM}$). Effector T cells ($T_E$, also called CTLs, killer T cells, cytolytic T cells, or cytotoxic T cells) are antigen-experienced $CD8^+$ cytotoxic T lymphocytes that have decreased expression of CD62L, CCR7, CD28, and are positive for granzyme and perforin as compared to $T_{CM}$. T helper cells ($T_H$) release cytokines to aid in antigen signaling and, when mature, express the surface protein CD4 (are CD4$^+$). "T cells" or "T lymphocytes" as described herein may be from any mammal, including primates or mice, and preferably from a human. In certain embodiments, T cells are autologous, allogeneic, or syngeneic to a subject treatable by the methods disclosed herein.

A "component of a TCR complex," as used herein, refers to a TCR chain (i.e., TCRα, TCRβ, TCRγ or TCRδ), a CD3 chain (i.e., CD3γ, CD3δ, CD3ε or CD3ζ), or a complex formed by two or more TCR chains or CD3 chains (e.g., a complex of TCRα and TCRβ, a complex of TCRγ and TCRδ, a complex of CD3ε and CD3δ, a complex of CD3γ and CD3ε, or a sub-TCR complex of TCRα, TCRβ, CD3γ, CD3δ, and two CD3ε chains).

Natural Killer cells are cytotoxic lymphocytes of the innate immune system. Unlike T cells, NK cells recognize stressed cells in the absence of MHC/HLA presentation, but play a similar cytotoxic role to CD8$^+$ effector T cells. In humans, NK cells typically express the surface markers CD16 (FcγRIII) and CD56. Upon activation (e.g., by antigen-binding or cytokine signaling from stressed cells), NK cells can release perforins and proteases (e.g., granzymes) that cause apoptosis or osmotic lysis of the stressed target cell. NK cells can also recognize antigen-bound antibodies through CD16 (FcγRIII) to initiate ADCC-mediated cytotoxic killing of target cells.

"NK-T" cells are a heterogeneous subpopulation of T cells that share properties of both T cells and NK cells. NK-T cells express both an αβ-TCR and the NK-marker NK1.1 (CD161), and recognize the antigen-presenting molecule CD1d (are CD1d-restricted). Following antigen activation, NK-T cells produce a number of cytokines that assist in immune response, including IFN-γ, IL-2, IL-4, and GM-CSF.

B cells, also referred to as B lymphocytes, are white blood cells of the adaptive immune system. B cells produce antibodies that bind to, and in some cases mediate destruction of, foreign substances or pathogens. Mature B cells and their differentiated progeny can be identified by molecules on their cell surface, such as B cell maturation antigen (BCMA, also known as tumor necrosis factor receptor superfamily member 17 (TNFRSF17), TNFRSF13A, and CD269), which is expressed on plasma cells and some mature B cells. BCMA has been shown to specifically bind to B cell activating factor (BAFF, also known as TNFSF13B TALL 1, and CD257) and a proliferation inducing ligand (APRIL, also known as TNFSF13 TALL 2, and CD256), which can lead to NF-κB activation. Plasma cells, also called plasma B cells, plasmocytes, plasmacytes, or effector B cells, are differentiated B cells that produce antibodies and are transported in serum or lymph.

Antitumor activity of the lymphocytes may be direct (e.g., cytotoxicity), such as in the case of CD8$^+$ effector T cells, NK cells, and NK-T cells that specifically recognize proteins expressed on the surface of cancer cells as antigens and attack the cancer, or may be indirect, such as in the case of B cells, which can produce antibodies that may be specific for cancer proteins, or CD4$^+$ T cells, which may identify cancer antigens and recruit, via cytokine release and other signaling mechanisms, other cells for direct antitumor activity.

Antitumor lymphocytes may be normally produced by the subject (i.e., "endogenous" or "native") and, in certain embodiments, may be isolated, engineered ex vivo to provide antigen specificity or for improved antitumor activity, and re-introduced into the subject in a cell-based therapy. As used herein, the term "endogenous" or "native" refers to a tissue, cell, polynucleotide, gene, protein, compound, molecule, or activity that is normally present in a host cell or a subject. Alternatively, antitumor lymphocytes may be derived from another source (i.e., "exogenous", "heterologous", or "non-endogenous") and administered to the subject in an adoptive cell therapy. In certain embodiments, cells modified ex vivo for use in adoptive cell therapy may be autologous, allogeneic, or syngeneic to the subject receiving the cells. As used herein, "heterologous" or "non-endogenous" or "exogenous" refers to any tissue, cell, gene, protein, compound, nucleic acid molecule, or activity that is not native to a host cell or a subject, or any tissue, cell, gene, protein, compound, nucleic acid molecule, or activity native to a host cell or a subject that has been altered. Heterologous, non-endogenous, or exogenous includes tissues, cells, genes, proteins, compounds, or nucleic acid molecules that have been engineered by human intervention (e.g., mutated) or otherwise altered such that the structure, activity, or both is different as between the native and altered cells, genes, proteins, compounds, or nucleic acid molecules.

Heterologous, non-endogenous, or exogenous tissues, cells, genes, proteins, or nucleic acid molecules (e.g., receptors, ligands, etc.) may not be endogenous to a host cell or a subject. In certain embodiments, nucleic acids encoding heterologous genes, proteins, or nucleic acid molecules may have been added to a host cell by conjugation, transformation, transfection, electroporation, or the like, wherein the added nucleic acid molecule may integrate into a host cell genome or can exist as extra-chromosomal genetic material (e.g., as a plasmid or other self-replicating vector). The term "homologous" or "homolog" refers to a gene, protein, compound, nucleic acid molecule, or activity found in or derived from a host cell, species, or strain. For example, a heterologous or exogenous polynucleotide or gene encoding a polypeptide may be homologous to a native polynucleotide or gene and encode a homologous polypeptide or activity, but the polynucleotide or polypeptide may have an altered structure, sequence, expression level, or any combination thereof. A non-endogenous polynucleotide or gene, as well as the encoded polypeptide or activity, may be from the same species, a different species, or a combination thereof.

As used herein, the term "engineered," "modified," "recombinant," or "non-natural" refers to an organism, microorganism, tissue, cell, nucleic acid molecule, or vector that includes at least one genetic alteration or has been modified by introduction of an exogenous nucleic acid molecule, wherein such alterations or modifications are introduced by genetic engineering (i.e., human intervention). Genetic alterations include, for example, modifications introducing expressible nucleic acid molecules encoding proteins, fusion proteins or enzymes, or other nucleic acid molecule additions, deletions, substitutions or other functional disruption of a cell's genetic material. Additional modifications include, for example, non-coding regulatory regions in which the modifications alter expression of a polynucleotide, gene or operon.

Various techniques are known for engineering or otherwise manipulating cells to attain or augment antitumor properties. For example, in some adoptive cell immunotherapies, peripheral blood mononuclear cells (PBMCs), hematopoietic stem cells (HSCs), or lymphocytes are removed from a subject, sorted, selected for antitumor activity, and cultured in vitro with lymphocyte-activating cytokines such as IL-2 and, optionally, an antigen (e.g., a cancer antigen), and then infused back into the same (autologous) or a different (allogeneic or syngeneic) subject to perform antitumor activity.

More specifically, a source of lymphocytes may be obtained from a subject (e.g., PBMCs, bone marrow, lymph node tissue, cord blood, thymus tissue, tissue from a site of infection, ascites, pleural effusion, or spleen tissue), from which lymphocytes are isolated. Specific lymphocyte subsets can be collected and enriched or depleted, such as affinity binding to antibodies, flow cytometry, or immunomagnetic selection. After enrichment or depletion steps to select desired cells, in vitro expansion of the desired lymphocytes can be carried out in accordance with known techniques (including those described in U.S. Pat. No. 6,040,177), or variations thereof that will be apparent to those skilled in the art. A desired lymphocyte population or subpopulation may be expanded by adding an initial lymphocyte population to a culture medium in vitro, and then adding feeder cells, such as non-dividing PBMCs, to the culture medium, (e.g., such that the resulting population of cells contains at least about 5, 10, 20, or 40 or more PBMC feeder cells for each lymphocyte cell in the initial population to be expanded); and incubating the culture (e.g. for a time sufficient to expand the numbers of T cells). Non-dividing feeder cells can comprise gamma-irradiated PBMC feeder cells. PBMCs can be irradiated with gamma rays in the range of about 3000 to 3600 rads. The order of addition of lymphocytes and feeder cells to the culture media can be reversed if desired. A culture can typically be incubated under conditions of temperature and the like that are suitable for the growth of the lymphocytes. For the growth of human T cells, for example, the temperature will generally be at least about 25° C., preferably at least about 30° C., more preferably about 37° C.

Optionally, expansion of the lymphocytes can comprise adding non-dividing Epstein-Barr Virus (EBV)-transformed lymphoblastoid cells (LCL) as feeder cells. LCL can be irradiated with gamma rays in the range of about 6000 to 10,000 rads. The LCL feeder cells may be provided in any suitable amount, such as a ratio of LCL feeder cells to initial lymphocytes of at least about 10:1. Following isolation, the lymphocytes may be sorted for desired characteristics. For example, for T lymphocytes, both CD8$^+$ cytotoxic and CD4$^+$ helper T lymphocytes can be sorted into naïve, memory, and effector T cell subpopulations before expanding. Further, lymphocytes may be sorted for antitumor activity, such as activation, expansion, cytokine secretion, antigen-binding, and cytotoxicity in the case of T cells, NK cells, and NK-T cells, or the production of antibodies specific for a cancer antigen, in the case of B cells. For example, immunomagnetic selection methods may also be used to purify T cell subpopulations using commercially available clinical grade antibody bead conjugates using a CliniMACS® device (see, e.g., Terakura et al., *Blood* 119:72-82, 2012; Wang et al., *J. Immunother.* 35:689-701, 2012). For example, human CD8$^+$ T$_{CM}$ cells may be enriched, isolated or purified by depleting CD4$^+$, CD14$^+$, and CD45RA$^+$ cells from peripheral blood mononuclear cells with antibody-conjugated paramagnetic beads, and then the CD62L$^+$ fraction from the remaining cells is positively selected with an anti-CD62L labeled bead to enrich for the CD45RO$^+$, CD62L$^+$, CD8$^+$ T$_{CM}$ subpopulation. The enriched CD8$^+$ T$_{CM}$ subpopulation can be activated with anti-CD3/CD28 beads or with antigen, modified with tumor-specific CAR using retroviral or lentiviral vectors, and expanded for use in cellular immunotherapy (see, e.g., Terakura et al., supra; Wang et al., supra).

Alternatively, lymphocyte subsets may be selected using low-affinity Fab fragments fused to an affinity binder (e.g., Strep-tag II). Fab monomers do not have sufficient binding affinity for stable binding to a target antigen on the cell surface. However, when multimerized on a Strep-Tactin® bead, these reagents stably bind a target cell and enable selection based on cell surface marker specificity. A Fab multimer binding can be rapidly reversed by the addition of excess D-biotin, which has a higher affinity for Strep-Tactin® and disrupts the binding between a Strep-tag on a Fab-fragment and a Strep-Tactin® "backbone." Fab monomers cannot maintain stable binding to the cell. This "Fab-Streptamers" technology allows for serial positive enrichment of lymphocytes based on multiple cell surface markers and can be used to select any desired lymphocyte subset (see, e.g., Stemberger et al., *PloS One* 7:e35798, 2012).

In another example, bulk CD8$^+$ T cells can be obtained and, optionally, further sorted into naïve, central memory, and effector T cells by identifying certain cell surface markers that are associated with each of those types of CD8$^+$ T cells. For example, memory T cells are present in both CD62L$^+$ and CD62L$^-$ subsets of CD8$^+$ peripheral blood lymphocytes. In another example, PBMCs can be sorted into CD62L$^-$CD8$^+$ and CD62L$^+$CD8$^+$ fractions after staining with anti-CD8 and anti-CD62L antibodies. Expression of phenotypic markers of CD8$^+$ central memory T cells include CD45RO, CD62L, CCR7, CD28, CD3, or CD127 or are negative for granzyme B. Central memory T cells are CD45RO$^+$, CD62L$^+$, CD8$^+$ T cells, and CD8$^+$ effector T cells are negative for or have reduced expression of CD62L, CCR7, CD28, or CD127, or are positive for or have increased expression of granzyme B or perforin, as compared to CD8$^+$ central memory T cells. Naïve CD8$^+$ T cells are characterized by the expression of phenotypic markers of naïve T cells including CD62L, CCR7, CD28, CD3, CD127, or CD45RA.

Bulk CD4$^+$ lymphocytes can also be obtained and may optionally be further sorted into naïve, central memory, and effector cells by identifying cell populations that have certain cell surface markers (e.g., naïve CD4$^+$ T lymphocytes are CD45RO$^-$, CD45RA$^+$, CD62L$^+$, CD4$^+$ T cells; central memory CD4$^+$ cells are CD62L positive and CD45RO positive; effector CD4$^+$ cells are CD62L or CD45RO negative or have reduced expression of CD62L or CD45RO as compared to central memory CD4$^+$ cells.

Further, lymphocytes may be sorted for antitumor activity, such as by activation, expansion, cytokine secretion, specific antigen-binding, and cytotoxicity in the case of T cells, NK cells, and NK-T cells, or the production of antibodies specific for a cancer antigen in the case of B cells. Using T cells as an example, populations of CD4$^+$ or CD8$^+$ having TCRs that are antigen-specific can be obtained by stimulating naïve or antigen-specific T lymphocytes with an antigen (e.g., tumor associated antigen, TAA). For example, T cell clones having antigen-specific TCRs can be generated against, for example, a TAA by isolating T cells from subjects having the particular tumor and stimulating the cells in vitro with the same antigen (e.g., in an antigen:MHC complex). Naïve T cells may also be used by exposing them to peptide antigens presented in the context of an antigen presenting cell or a peptide-MHC complex. Any number of antigens from tumor cells or cancer cells may be utilized. Exemplary tumor antigens include ROR1, EGFR, EGFRvIII, GD2, GD3, HPV E6, HPV E7, Her2, L1-CAM, Lewis A, Lewis Y, MUC1, MUC16, PSMA, CD19, CD20, CD22, CD56, CD23, CD24, CD37, CD30, CD33, CD38, CD56, CD123, CA125, c-MET, FcRH5, WT1, folate receptor α, VEGF-α, VEGFR1, VEGFR2, IL-13Rα2, IL-11Rα, MAGE-A1, PSA, ephrin A2, ephrin B2, NKG2D ligands, NY-ESO-1, TAG-72, mesothelin, CEA, or the like. Such T cells having antigen-specific TCRs may be further modified to contain a fusion protein as described herein, wherein the fusion protein is specific for the same antigen, specific for a different epitope on the same antigen, or specific for a different antigen.

Methods of preparing and modifying lymphocytes to have antitumor or improved antitumor activity, confirming modified T cell activity, and expanding modified T cell populations are described, for example, in Hollyman et al., *J. Immunother.* 32:169-180, 2009; PCT Publication No. WO 2012/079000; U.S. Pat. No. 8,802,374; Brentjens et al., *Blood* 118:4817-4828, 2011; U.S. Patent Publication No. US 2014/0271635; and Walseng et al., *Scientific Reports* 7:10713, 2017; the methods, modified lymphocytes, and antigen-binding proteins of which are hereby incorporated by reference in their entirety.

Further, lymphocytes such as CD8$^+$ effector T cells, CD4$^+$ helper T cells, NK cells, or NK-T cells may be engineered to express a heterologous immunoreceptor that specifically binds a cancer protein expressed by tumor cells. See, e.g., Humphries, C., *Nature* 504:S13-S15, 2013. An example of a heterologous immunoreceptor that may be expressed by an engineered antitumor lymphocyte includes a naturally occurring T cell receptor (TCR) specific for a cancer antigen. Other exemplar heterologous immunoreceptors include chimeric antigen receptors (CARs, also called chimeric immunoreceptors), which are fusion proteins comprising an antigen binding domain (e.g., obtained or derived from an immunoglobulin or immunoglobulin-like molecule, such as an scFv or scTCR derived from an antibody or TCR specific for a cancer antigen, or an antigen binding domain obtained or derived from a killer immunoreceptor from an NK cell) linked to a transmembrane domain and one or more intracellular signaling domains (optionally containing co-stimulatory domain(s)), and modified TCRs (see, e.g., Sadelain et al., *Cancer Discov.*, 3(4): 388-398, 2013; see also Harris and Kranz, *Trends Pharmacol. Sci.*, 37(3): 220-230, 2016; Stone et al., *Cancer Immunol. Immunother.*, 63(11):1163-1176, 2014). Methods of making synthetic immunoreceptors, including CARs, are described, for example, in U.S. Pat. Nos. 6,410,319; 7,446,191; U.S. Patent Publication No. 2010/065818; U.S. Pat. No. 8,822,647; PCT Publication No. WO 2014/031687; U.S. Pat. No. 7,514,537; Walseng et al., *Scientific Reports* 7:10713, 2017; and Brentjens et al., *Clin. Cancer Res.* 13:5426, 2007.

As used herein, the term "immune response" refers to the action of an immune cell, for example, a lymphocyte (including antitumor lymphocyte), antigen presenting cell, phagocytic cell, granulocyte, or soluble macromolecule produced by the above cells or the liver (including antibodies, cytokines, and complement), that results in selective damage to, reduction in growth or spread of, destruction of, or elimination of cancerous cells. In certain embodiments, an immune response comprises an antigen-specific T cell response.

The phrase "inducing or enhancing an immune response" refers to causing or stimulating an immune cell (e.g., an antitumor lymphocyte) to have a sustained or amplified biological function. For example, induced or enhanced T cell responses include increased production of cytokines by CD8+ T cells, increased proliferation, or increased antigen responsiveness relative to the response before intervention, or an induced or enhanced B cell response includes activation of, increased or prolonged production of antibodies. In certain embodiments, the level of antitumor activity (e.g., cytotoxic activity against cancer cells in a non-inflamed solid tumor) after, e.g., exposure to an activating cytokine or a peptide antigen, or administration of an inhibitor of an immune checkpoint molecule as described herein, is as least about 25%, 30%, 35%, 40%, 45%, 50%, 55%, 60%, 65%, 70%, 75%, 80%, 85%, 90%, 95%, 99%, or more, as compared to immune cells not contacted with the activating cytokine, peptide antigen, or without administration of the inhibitor of an immune checkpoint molecule. An assay for detecting cytokine levels (e.g., IL-2, IL-10, IFNγ) to determine whether an immune response induced or enhanced comprises the multiplex assay described by Dossus et al. (*J. Immunol. Methods* 350:125, 2009). An assay for detecting T cell proliferation to determine whether an immune response induced or enhanced comprises the assay described by Liu et al. (*Clin. Cancer Res.* 21:1639, 2015). An assay for determining increased antigen responsiveness comprises the assay described by Tumeh et al. (*Nature* 515:568, 2014).

Antitumor lymphocytes generated for a subject may be given as fresh cells immediately after manufacture, or may be cryopreserved and stored in a liquid nitrogen freezer before being thawed and washed to remove residual cryoprotectant to prepare a composition for infusion. The total number of cells will be sufficient to account for cell loss during recovery from thaw and to achieve the cell dose level specified in the clinical protocol. In certain embodiments comprising both CD4$^+$ and CD8$^+$ T cells, the total ratio of CD4$^+$ and CD8$^+$ T cells may differ from 1:1 due to differences in transduction of the individual subsets in individual subjects. For this reason, the subsets may be transduced separately to achieve a desired formulation of the transduced T cells. CD4 and CD8 CAR T cells have demonstrated synergistic effects in animal models (Sommermeyer et al., *Leukemia* 2015).

Transformed cells may be suspended in an appropriate cryopreservation medium (e.g., CryoStor CS10®) for cryopreservation in a controlled rate freezer. Cryopreserved cells may be stored in the vapor phase of a liquid nitrogen freezer. The fresh or thawed cells may then be resuspended in Normosol+ 1% HSA and transferred to a transfer pack at the total cell dose level specified in the clinical protocol. The formulated product may be stored at 2-8° C. and then transferred under appropriate conditions to the clinical site for administration.

Following leukapharesis, subjects may receive cytoreductive chemotherapy to control disease during production of the transformed cells. For example, in certain embodiments, a subject may receive may receive low-intensity chemotherapy (e.g. lenalidomide, ibrutinib) after leukapheresis. Prior to administering transformed cells according to the present disclosure, chemotherapy or immune modulatory therapy may be appropriate in order to provide lymphodepletion to facilitate survival of transferred T cells, and to reduce the tumor burden prior to infusion of the cells. For example, subjects may receive lymphodepleting chemotherapy for a predetermined time prior to (e.g., 36-96 hours) the infusion of the cells. In certain embodiments, a subject may initially be treated with a single dose of a chemotherapy agent such as cyclophosphamide (CY) i.v. (e.g., at 1 g/m$^2$) initially. However, if the subject response rate is determined to be inadequate, the lymphodepletion regimen may be changed so that subsequent patients receive a second, further chemotherapeutic or immunomodulatory agent (e.g., CY+ fludarabine). Additionally, a subject may, but need not, receive a premedication prior to administration of the cells.

One or more intravenous infusions of the antitumor lymphocytes described herein may be administered to the subject following completion of lymphodepleting chemotherapy (e.g., 36-96 hours thereafter). The dose of cells administered to the subject may be determined according to predetermined dose levels, and may be adjusted thereafter to increase, decrease, or otherwise change the amount, composition, ratio, or rate of the cells administered. In certain embodiments, a single infusion is administered to the subject. In further embodiments, a second infusion may be given if the first infusion does not produce a complete response (CR), or if the disease relapses after a CR. In still further embodiments, a third, fourth, fifth, sixth, seventh, eighth, ninth, tenth, or further infusion may be given. In certain embodiments, a cell infusion may be administered intravenously over a selected period of time (e.g., approximately 20-30 minutes), adjusted as needed to comply with guidelines for endotoxin limits for parenteral drugs (about 5 EU/kg/hour). Further, adoptive cell therapy using allogeneic lymphocytes may involve modulating host (recipient) immune recognition of transplanted or engineered cells as "non-self." This may involve inhibiting or abrogating expression of endogenous immunoreceptors in the transplanted cells (see, e.g., U.S. Pat. No. 9,181,527) or, as discussed further herein, modulating immune inhibitor systems in the host (e.g., immune checkpoint inhibitors; see Baghdadi et al., *mAbs* 6(5):1124-1132, 2014).

In certain embodiments, an antitumor lymphocyte of this disclosure is engineered to comprise a chromosomal gene knockout of one or more genes encoding a PD-1, LAG-3, CTLA4, TIM3, TIGIT, an HLA complex component (e.g., a gene that encodes an $\alpha 1$ macroglobulin, an $\alpha 2$ macroglobulin, an $\alpha 3$ macroglobulin, a $\beta 1$ microglobulin, or a $\beta 2$ microglobulin), a TCR component (e.g., a gene that encodes a TCR variable region or a TCR constant region) (see, e.g., Torikai et al., *Nature Sci. Rep.* 6:21757 (2016); Torikai et al., *Blood* 119(24):5697 (2012); and Torikai et al., *Blood* 122(8): 1341 (2013); the gene editing techniques, compositions, and adoptive cell therapies of which are incorporated herein by reference in their entirety). For example, in some embodiments, a chromosomal gene knockout is produced using a CRISPR/Cas9 system, and may involve transfection of the lymphocyte with a lentivirus (e.g., pLentiCRISPRv2; Torikai et al., *Blood* (2016)) expressing a CRISPR/Cas9 system targeting PD-1, LAG-3, CTLA4, an HLA component, or a TCR component, or any combination thereof. In other embodiments, a chromosomal gene knockout is generated using a homing endonuclease that have been modified with the modular DNA binding domains of TALENs to make a fusion protein known as megaTALs. MegaTALS can be utilized not only to knock-out genes but also to introduce (knock in) heterologous or exogenous polynucleotides when used in combination with an exogenous donor template encoding a polynucleotide of interest, such as a TCRα chain, TCRβ chain or both.

A therapeutically effective amount of cells in an antitumor lymphocyte composition, for administration concurrently with, simultaneously to, or after an eIF4A inhibitor, is at least one greater than $10^2$ cells, for example, up to $10^6$, up to $10^7$, up to $10^8$ cells, up to $10^9$ cells, or more than $10^{10}$ cells. In certain embodiments, the cells are administered in a range from about $10^6$ to about $10^{10}$ cells/m$^2$, or in a range of about $10^5$ to about $10^9$ cells/m$^2$. For example, cells (naturally occurring or engineered) specific for a particular antigen will comprise a cell population containing at least 30%, 35%, 40%, 45%, 50%, 55%, 60%, 65%, 70%, 75%, 80%, 85%, 90%, 95% or more of such cells. For uses provided herein, cells are generally in a volume of a liter or less, 500 mls or less, 250 mls or less, or 100 mls or less. In some embodiments, the density of the desired cells is typically greater than $10^4$ cells/ml and generally is greater than $10^7$ cells/ml, $10^8$ cells/ml or greater. The cells may be administered as a single infusion or in multiple infusions over a range of time. A clinically relevant number of immune cells can be apportioned into multiple infusions that cumulatively equal or exceed $10^6$, $10^7$, $10^8$, $10^9$, $10^{10}$, or $10^{11}$ cells.

In certain embodiments, a unit dose of antitumor lymphocytes comprises (i) a composition comprising at least about 30%, at least about 40%, at least about 50%, at least about 60%, at least about 70%, at least about 80%, at least about 85%, at least about 90%, or at least about 95% engineered CD4$^+$ T cells, combined with (ii) a composition comprising at least about 30%, at least about 40%, at least about 50%, at least about 60%, at least about 70%, at least about 80%, at least about 85%, at least about 90%, or at least about 95% engineered CD8$^+$ T cells, in about a 1:1 ratio, wherein the unit dose contains a reduced amount or substantially no naïve T cells (i.e., has less than about 50%, less than about 40%, less than about 30%, less than about 20%, less than about 10%, less than about 5%, or less then about 1% the population of naïve T cells present in a unit dose as compared to a patient sample having a comparable number of PBMCs).

In some embodiments, a unit dose comprises (i) a composition comprising at least about 50% engineered CD4$^+$ T cells, combined with (ii) a composition comprising at least about 50% engineered CD8$^+$ T cells, in about a 1:1 ratio, wherein the unit dose contains a reduced amount or substantially no naïve T cells. In further embodiments, a unit dose comprises (i) a composition comprising at least about 60% engineered CD4$^+$ T cells, combined with (ii) a composition comprising at least about 60% engineered CD8$^+$ T cells, in about a 1:1 ratio, wherein the unit dose contains a reduced amount or substantially no naïve T cells. In still further embodiments, a unit dose comprises (i) a composition comprising at least about 70% engineered CD4$^+$ T cells, combined with (ii) a composition comprising at least about 70% engineered CD8$^+$ T cells, in about a 1:1 ratio, wherein the unit dose contains a reduced amount or substantially no naïve T cells. In some embodiments, a unit dose comprises (i) a composition comprising at least about 80% engineered CD4$^+$ T cells, combined with (ii) a composition comprising at least about 80% engineered CD8$^+$ T cells, in about a 1:1 ratio, wherein the unit dose contains a reduced amount or substantially no naïve T cells. In some embodiments, a unit dose comprises (i) a composition comprising at least about 85% engineered CD4$^+$ T cells, combined with (ii) a composition comprising at least about 85% engineered CD8$^+$ T cells, in about a 1:1 ratio, wherein the unit dose contains a reduced amount or substantially no naïve T cells. In some embodiments, a unit dose comprises (i) a composition comprising at least about 90% engineered CD4$^+$ T cells, combined with (ii) a composition comprising at least about 90% engineered CD8$^+$ T cells, in about a 1:1 ratio, wherein the unit dose contains a reduced amount or substantially no naïve T cells.

In any of the embodiments described herein, a unit dose comprises equal, or approximately equal, numbers of engineered CD45RA$^-$ CD3$^+$ CD8$^+$ and engineered CD45RA$^-$ CD3$^+$ CD4$^+$ T$_M$ cells.

Methods of Treatment

In certain embodiments, the present disclosure provides methods for treating a hyperproliferative disorder, such as a non-inflamed tumor, by administering an eIF4A inhibitor to promote infiltration of antitumor lymphocytes (i.e., endogenous or non-endogenous lymphocytes) into a tumor. For example, administration of an effective amount of an eIF4A inhibitor may result in the infiltration of a tumor by antitumor lymphocytes where there had not previously been infiltration, or may increase the infiltration of a tumor by antitumor lymphocytes by about 10%, about 20%, about 30%, about 40%, about 50%, about 60%, about 70%, about 80%, about 90%, about 100%, about 200%, about 300%, about 400%, about 500%, about 1000%, or more. Infiltration by, or antitumor activity of, antitumor lymphocytes can be determined using, for example, immunohistochemistry staining for known markers of the antitumor lymphocyte (e.g., CD8, CD4, CD3, or a heterologous or synthetic surface marker protein), imaging for a reporter protein (e.g., a fluorescent protein expressed by the antitumor lymphocyte), or in vivo imaging techniques (e.g., MRI, PET, or the like), or by measuring levels of cytokines indicative of lymphocyte antitumor activity (e.g., IL-6, IL-8, IL-10, TNF-α, MCP1, IL-1β, IL-15, and IFN-γ), or by measuring levels of immunogenic cell death markers as indicators of tumor cell death (see, e.g., Tesniere et al., *Cell Death and Differentiation* 15:3 (2008); see also Woller et al., *Front. Oncol.* 4:188 (2014)).

As used herein, "hyperproliferative disorder" refers to excessive growth or proliferation as compared to a normal or undiseased cell. Exemplary hyperproliferative disorders include tumors, cancers, neoplastic tissue, carcinoma, sarcoma, malignant cells, pre malignant cells, as well as non-neoplastic or non-malignant hyperproliferative disorders (e.g., adenoma, fibroma, lipoma, leiomyoma, hemangioma, fibrosis, restenosis, as well as autoimmune diseases such as rheumatoid arthritis, osteoarthritis, psoriasis, inflammatory bowel disease, or the like). The increased infiltration of the tumor by antitumor lymphocytes may result in treatment of the cancer in the subject, which may include one or more of: an improved clinical outcome; lessening or alleviation of symptoms associated with cancer; decreased occurrence of symptoms; improved quality of life; longer disease-free status; diminishment of extent of cancer (e.g., tumor growth, grade, size, number, or spread or rate of spread of the cancer); stabilization of cancer; delay of cancer progression; remission; survival; or prolonging survival.

In certain embodiments, methods for treating a hyperproliferative disorder (e.g., cancer, non-inflamed tumor) according to the present disclosure comprise administering a therapeutically effective amount of an eIF4A inhibitor according to Formula I:

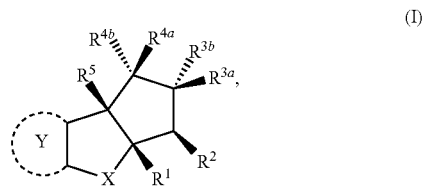

(I)

or stereoisomers, tautomers or pharmaceutically acceptable salts thereof, wherein:

X is $CR^6R^7$, O, S, NH, $N(C_1-C_8)$alkyl, C(O), $C=CR^6R^7$, $N(CO)R^8$, S(O) or $S(O)_2$;

Y is a 5-membered heteroaryl or a 6-membered aryl or heteroaryl;

$R^1$ and $R^2$ independently are aryl, heterocyclyl, heteroaryl or cycloalkyl;

$R^{3a}$, $R^{3b}$, $R^{4a}$ and $R^{4b}$ independently are H, halogen, CN, $C_1-C_8$(alkyl), $(C_1-C_8)$haloalkyl, $C_2-C_8$(alkenyl), $(C_2-C_8)$alkynyl, $OR^9$, $NHR^9$, $NR^9R^9$, $[(C_1-C_8)$alkylene]$OR^9$, $[(C_1-C_8)$alkylene]$NHR^9$, $[(C_1-C_8)$alkylene]$NR^9R^9$, $C(O)R^8$, $C(O)NHR^9$, $C(O)NR^9R^9$, $C(O)[(C_1-C_8)$alkylene]$NHR^9$, $C(O)[(C_1-C_8)$alkylene]$NR^9R^9$, $CO_2R^9$, $C(S)NHR^9$, $C(S)NR^9R^9$, $SR^9$, $S(O)R^9$, $SO_2R^9$, $SO_2NHR^9$, $SO_2NR^9R^9$, $NH(CO)R^8$, $NR^9(CO)R^8$, $NH(CO)NHR^9$, $NH(CO)NR^9R^9$, $NR^9(CO)NHR^9$, $NR^9(CO)NR^9R^9$, $P(O)(OH)(OR^9)$, $P(O)(OR^9)(OR^9)$, aryl, heteroaryl, cycloalkyl or heterocyclyl;

$R^{3a}$ and $R^{3b}$, and $R^{4a}$ and $R^{4b}$ independently combine to form oxo or alkenyl, or a cycloalkyl or heterocyclyl ring; or $R^{3a}$ and $R^{4a}$, $R^{3b}$ and $R^{4b}$ or $R^{4a}$ and $R^5$ together with the carbon atom to which they are attached form a cycloalkyl or heterocyclyl ring; or $R^2$ and $R^{3a}$ together with the carbon atom to which they are attached form a bicyclic ring system;

$R^5$ is H, halogen, OH, CN, $N_3$, $SR^9$, $(C_1-C_8)$alkyl, $(C_1-C_8)$haloalkyl, $O(C_1-C_8)$alkyl, $O(C_1-C_8)$haloalkyl, $(C_2-C_8)$alkynyl, $NHC(O)(C_1-C_8)$alkyl or heteroaryl;

$R^6$ and $R^7$ independently are H, CN, halogen, $OR^9$, $SR^9$, $(C_1-C_8)$alkyl, $NH(R^9)$ or $NR^9R^9$;

$R^8$ is H, $(C_1-C_8)$alkyl, $(C_1-C_8)$haloalkyl, $O(C_1-C_8)$alkyl, $O(C_1-C_8)$haloalkyl, cycloalkyl, O(cycloalkyl), heterocyclyl, O(heterocyclyl), aryl, O(aryl), heteroaryl or O(heteroaryl);

$R^9$ is H, $(C_1-C_8)$alkyl, $(C_1-C_8)$haloalkyl, cycloalkyl, heterocyclyl, $[(C_1-C_8)$alkylene] heterocyclyl, aryl, $[(C_1-C_8)$alkylene] aryl or heteroaryl;

wherein the two $R^9$'s together with the nitrogen atom to which they are attached of $NR^9R^9$, $[(C_1-C_8)$alkylene]$NR^9R^9$, $C(O)NR^9R^9$, $C(O)[(C_1-C_8)$alkylene]$NR^9R^9$, $C(S)NR^9R^9$, $SO_2NR^9R^9$, $NH(CO)NR^9R^9$ or $NR^9(CO)NR^9R^9$, optionally form a heterocyclyl ring;

wherein any alkyl, alkenyl, cycloalkyl, heterocyclyl, heteroaryl or aryl is optionally substituted with 1, 2, or 3 groups selected from OH, CN, SH, $SO_2NH_2$, $SO_2(C_1-C_4)$alkyl, $SO_2NH(C_1-C_4)$alkyl, halogen, $NH_2$, $NH(C_1-C_4)$alkyl, $N[(C_1-C_4)$alkyl]$_2$, $C(O)NH_2$, COOH, COOMe, acetyl, $(C_1-C_8)$alkyl, $O(C_1-C_8)$alkyl, $O(C_1-C_8)$haloalkyl, $(C_2-C_8)$alkenyl, $(C_2-C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—$[CH(OH)]_m$—$(CH_2)_p$—OH, $CH_2$—$[CH(OH)]_m$—$(CH_2)_p$—$NH_2$ or $CH_2$-aryl-alkoxy; or wherein any alkyl, cycloalkyl or heterocyclyl is optionally substituted with oxo;

"m" and "p" are 1, 2, 3, 4, 5 or 6; and wherein when Y is a 6-membered aryl then X is not O.

In some embodiments, the 6-membered aryl or heteroaryl is

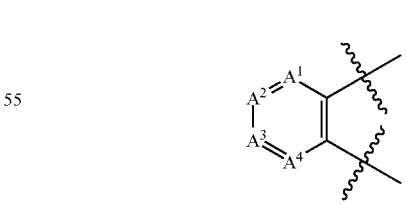

wherein $A^1$ is N or CR;

$A^2$ is N or CR;

$A^3$ is N or $CR^{12}$;

$A^4$ is N or $CR^{13}$; and $R^{10}$, $R^{11}$, $R^{12}$ and $R^{13}$ independently are H, halogen, $C_1-C_8$(alkyl), $(C_1-C_8)$haloalkyl, $C(O)O(C_1-C_8)$alkyl, C(O)

$(C_1-C_8)$alkyl, $SO_2(C_1-C_8)$alkyl, $C_2-C_8$(alkenyl), $(C_2-C_8)$alkynyl, $OR^9$, $NHR^9$, $NR^9R^9$, CN, $[(C_1-C_8)$alkylene$]OR^9$, $[(C_1-C_8)$alkylene$]NHR^9$, $[(C_1-C_8)$alkylene$]NR^9R^9$, $C(O)R^8$, $C(O)NHR^9$, $C(O)NR^9R^9$, $C(O)[(C_1-C_8)$alkylene$]NHR^9$, $C(O)[(C_1-C_8)$alkylene$]NR^9R^9$, $CO_2R^9$, $C(S)NHR^9$, $C(S)NR^9R^9$, $SR^9$, $S(O)R^9$, $SO_2R^9$, $SO_2NHR^9$, $SO_2NR^9R^9$, $NH(CO)R^8$, $NR^9(CO)R^8$, $NH(CO)NHR^9$, $NH(CO)NR^9R^9$, $NR^9(CO)NHR^9$, $NR^9(CO)NR^9R^9$, $P(O)(OH)(OR^9)$, $P(O)(OR^9)(OR^9)$, aryl, heteroaryl, cycloalkyl or heterocyclyl.

In certain embodiments, the 5-membered heteroaryl is

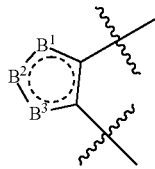

wherein any two of $B^1$, $B^2$ and $B^3$ are $CR^{14}$ and N and the remaining B ring atom is $N(R^{15})$ or S, wherein $R^{14}$ is H, CN, halogen, $OR^9$, $SR^9$, $(C_1-C_8)$alkyl, $C(O)O(C_1-C_8)$alkyl, $C(O)(C_1-C_8)$alkyl, $SO_2(C_1-C_8)$alkyl, $SO_2NR^9R^9$, $C(O)NR^9R^9$, $NR^9R^9$ or $NR^9C(O)R^8$, and $R^{15}$ is H or $(C_1-C_8)$alkyl.

In certain embodiments, methods for treating a hyperproliferative disorder (e.g., cancer, non-inflamed tumor) according to the present disclosure comprises administering a therapeutically effective amount of an eIF4A inhibitor according to the following formula:

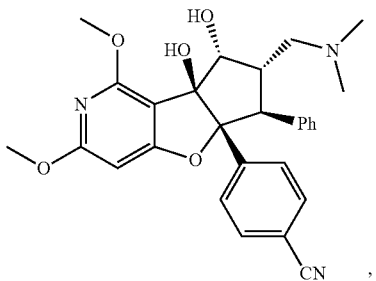

or a stereoisomer, tautomer, or pharmaceutically acceptable salt thereof.

A "therapeutically effective amount" or "effective amount", as used herein, is an amount of a therapeutic reagent sufficient to result in a therapeutic effect, including: improved clinical outcome; lessening or alleviation of symptoms associated with a disease; decreased occurrence of symptoms; improved quality of life; longer disease-free status; diminishment of extent of disease, stabilization of disease state; delay of disease progression; remission; survival; or prolonged survival in a statistically significant manner. When referring to an individual reagent or cell as disclosed herein, administered alone, a therapeutically effective amount refers to the effects of the individual reagent or cell. When referring to a combination, a therapeutically effective amount refers to the combined amounts of reagents or combined adjunctive reagent with a cell that results in a therapeutic effect, whether administered concurrently, sequentially, or simultaneously. A combination may also and another relevant therapeutic reagent.

As used herein, "statistically significant" refers to a p value of 0.050 or less when calculated using the Students t-test and indicates that it is unlikely that a particular event or result being measured has arisen by chance.

"Treat" or "treatment" or "ameliorate" refers to medical management of a disease, disorder, or condition of a subject (e.g., a human or non-human mammal, such as a primate, horse, cat, dog, goat, mouse, or rat). In general, an appropriate dose or treatment regimen comprising a therapeutically effective amount of an eIF4A inhibitor is sufficient to result in one or more therapeutic benefit, such as, for example, decreased translation of TGFβ in a non-inflamed solid tumor, decreased translation of collagen in a non-inflamed solid tumor, decreased presence of TGFβ in a non-inflamed solid tumor or in the microenvironment of a non-inflamed solid tumor; decreased TGFβ-mediated signaling (e.g., of cytokines) in a non-inflamed solid tumor or in the microenvironment of a non-inflamed solid tumor; decreased presence of collagen or collagen having decreased stability in a non-inflamed solid tumor or in the microenvironment of the non-inflamed solid tumor; a decrease in the amount, density, replacement rate, or structural integrity of the extracellular matrix of a non-inflamed solid tumor; and increased infiltration of a non-inflamed solid tumor by lymphocytes, preferably by antitumor lymphocytes as described herein.

Methods according to this disclosure may comprise administering an eIF4A inhibitor in combination with one or more additional agents, wherein the eIF4A inhibitor increases infiltration of antitumor lymphocytes into a non-inflamed solid tumor, thereby treating the cancer. For example, in certain embodiments, a combination therapy comprises administering an eIF4A inhibitor with (concurrently, simultaneously, or sequentially) antitumor lymphocytes (e.g., modified antitumor lymphocytes) as described herein. In some embodiments, a combination therapy comprises administering an eIF4A inhibitor with an inhibitor of an immune suppression component. In certain embodiments, a combination therapy comprises administering an eIF4A inhibitor with an agonist of a stimulatory immune checkpoint component. In yet other embodiments, a combination therapy comprises administering an eIF4A inhibitor with a secondary therapy, such as an antibody or antigen-binding fragment specific for a cancer antigen expressed on the non-inflamed solid tumor, a chemotherapeutic agent, radiation therapy, surgery, an anticancer cytokine, an RNA interference molecule, or any combination thereof, either simultaneously, concurrently, or sequentially.

As used herein, the term "immune suppression component" or "immunosuppression component" refers to one or more cells, proteins, molecules, compounds or complexes providing inhibitory signals to assist in controlling or suppressing an immune response. For example, immune suppression components include those molecules that partially or totally block immune stimulation; decrease, prevent or delay immune activation; or increase, activate, or up regulate immune suppression. Exemplary immunosuppression component targets are described in further detail herein and include PD-1, PD-L1, PD-L2, LAG3, CTLA4, B7-H3, B7-H4, CD244/2B4, HVEM, BTLA, CD160, TIM3, GAL9, KIR, PVR1G (CD112R), PVRL2, adenosine, A2aR, immunosuppressive cytokines (e.g., IL-10, IL-4, IL-1RA, IL-35), IDO, arginase, VISTA, TIGIT, LAIR1, CEACAM-1, CEACAM-3, CEACAM-5, Treg cells, or any combination thereof.

An inhibitor of an immune suppression component may be a compound, an antibody, an antibody fragment or fusion polypeptide (e.g., Fc fusion, such as CTLA4-Fc or LAG3-Fc), an antisense molecule, a ribozyme or RNAi molecule, or a low molecular weight organic molecule. In any of the embodiments disclosed herein, a method may comprise administering an eIF4A inhibitor with one or more inhibitor of any one of the following immune suppression components, singly or in any combination.

In certain embodiments, an eIF4A inhibitor is used in combination with a PD-1 inhibitor, for example a PD-1-specific antibody or binding fragment thereof, such as pidilizumab, nivolumab (Keytruda, formerly MDX-1106), pembrolizumab (Opdivo, formerly MK-3475), MEDI0680 (formerly AMP-514), AMP-224, BMS-936558 or any combination thereof. In some embodiments, an eIF4A inhibitor is used in combination with a PD-L1 specific antibody or binding fragment thereof, such as BMS-936559, durvalumab (MEDI4736), atezolizumab (RG7446), avelumab (MSB0010718C), MPDL3280A, or any combination thereof.

In some embodiments, an eIF4A inhibitor is used in combination with a LAG3 inhibitor, such as LAG525, IMP321, IMP701, 9H12, BMS-986016, or any combination thereof.

In certain embodiments, an eIF4A inhibitor is used in combination with an inhibitor of CTLA4. In particular embodiments, an eIF4A inhibitor is used in combination with a CTLA4 specific antibody or binding fragment thereof, such as ipilimumab, tremelimumab, CTLA4-Ig fusion proteins (e.g., abatacept, belatacept), or any combination thereof.

In certain embodiments, an eIF4A inhibitor is used in combination with a B7-H3 specific antibody or binding fragment thereof, such as enoblituzumab (MGA271), 376.96, or both. A B7-H4 antibody binding fragment may be a scFv or fusion protein thereof, as described in, for example, Dangaj et al., Cancer Res. 73:4820, 2013, as well as those described in U.S. Pat. No. 9,574,000 and PCT Patent Publication Nos. WO 2016/40724 and WO 2013/025779.

In some embodiments, an eIF4A inhibitor is used in combination with an inhibitor of CD244.

In certain embodiments, an eIF4A inhibitor is used in combination with an inhibitor of BLTA, HVEM, CD160, or any combination thereof. Anti-CD-160 antibodies are described in, for example, PCT Publication No. WO 2010/084158.

In more embodiments, an eIF4A inhibitor is used in combination with an inhibitor of TIM3.

In still more embodiments, an eIF4A inhibitor is used in combination with an inhibitor of Gal9.

In certain embodiments, an eIF4A inhibitor is used in combination with an inhibitor of adenosine signaling, such as a decoy adenosine receptor.

In certain embodiments, an eIF4A inhibitor is used in combination with an inhibitor of A2aR.

In certain embodiments, an eIF4A inhibitor is used in combination with an inhibitor of KIR, such as lirilumab (BMS-986015).

In certain embodiments, an eIF4A inhibitor is used in combination with an inhibitor of an inhibitory cytokine (typically, a cytokine other than TGFβ) or Treg development or activity.

In some embodiments, an eIF4A inhibitor is used in combination with an IDO inhibitor, such as levo-1-methyl tryptophan, epacadostat (INCB024360; Liu et al., Blood 115:3520-30, 2010), ebselen (Terentis et al., Biochem. 49:591-600, 2010), indoximod, NLG919 (Mautino et al., American Association for Cancer Research 104th Annual Meeting 2013; Apr. 6-10, 2013), 1-methyl-tryptophan (1-MT)-tira-pazamine, or any combination thereof.

In certain embodiments, an eIF4A inhibitor is used in combination with an arginase inhibitor, such as N(omega)-Nitro-L-arginine methyl ester (L-NAME), N-omega-hydroxy-nor-l-arginine (nor-NOHA), L-NOHA, 2(S)-amino-6-boronohexanoic acid (ABH), S-(2-boronoethyl)-L-cysteine (BEC), or any combination thereof.

In some embodiments, an eIF4A inhibitor is used in combination with an inhibitor of VISTA, such as CA-170 (Curis, Lexington, Mass.).

In some embodiments, an eIF4A inhibitor is used in combination with an inhibitor of TIGIT such as, for example, COM902 (Compugen, Toronto, Ontario Canada), an inhibitor of CD155, such as, for example, COM701 (Compugen), or both.

In certain embodiments, an eIF4A inhibitor is used in combination with an inhibitor of PVRIG, PVRL2, or both. Anti-PVRIG antibodies are described in, for example, PCT Publication No. WO 2016/134333. Anti-PVRL2 antibodies are described in, for example, PCT Publication No. WO 2017/021526.

In certain embodiments, an eIF4A inhibitor is used in combination with a LAIR1 inhibitor.

In more embodiments, an eIF4A inhibitor is used in combination with an inhibitor of CEACAM-1, CEACAM-3, CEACAM-5, or any combination thereof.

In certain embodiments, an eIF4A inhibitor is used in combination with an agent that increases the activity (i.e., is an agonist) of a stimulatory immune checkpoint molecule. For example, an eIF4A inhibitor can be used in combination with a CD137 (4-1BB) agonist (such as, for example, urelumab), a CD134 (OX-40) agonist (such as, for example, MED16469, MEDI6383, or MED10562), lenalidomide, pomalidomide, a CD27 agonist (such as, for example, CDX-1127), a CD28 agonist (such as, for example, TGN1412, CD80, or CD86), a CD40 agonist (such as, for example, CP-870,893, rhuCD40L, or SGN-40), a CD122 agonist (such as, for example, IL-2), an agonist of GITR (such as, for example, humanized monoclonal antibodies described in PCT Patent Publication No. WO 2016/054638), or an agonist of ICOS (CD278) (such as, for example, GSK3359609, mAb 88.2, JTX-2011, Icos 145-1, or Icos 314-8), or any combination thereof. In any of the embodiments disclosed herein, a method may comprise administering an eIF4A inhibitor with one or more agonist of a stimulatory immune checkpoint molecule, including any of the foregoing, singly or in any combination.

In certain embodiments, a combination therapy comprises administering an eIF4A inhibitor and a secondary therapy comprising one or more of an antibody or antigen binding-fragment thereof that is specific for a cancer antigen expressed by the non-inflamed solid tumor, radiation treatment, surgery, a chemotherapeutic agent, a cytokine, a RNAi, or any combination thereof.

Exemplary monoclonal antibodies useful in cancer therapies are known in the art and include, for example, monoclonal antibodies described in Galluzzi et al., Oncotarget 5(24):12472-12508, 2014.

In certain embodiments, a combination therapy method comprises administering an eIF4A inhibitor and further administering a radiation treatment or a surgery. Radiation therapy is well-known in the art and includes X-ray therapies, such as gamma-irradiation, and radiopharmaceutical therapies. Surgeries and surgical techniques appropriate to treating a given cancer or non-inflamed solid tumor in a subject are well-known to those of ordinary skill in the art.

In certain embodiments, a combination therapy method comprises administering an eIF4A inhibitor and further administering a chemotherapeutic agent. A chemotherapeutic agent includes, but is not limited to, an inhibitor of chromatin function, a topoisomerase inhibitor, a microtubule inhibiting drug, a DNA damaging agent, an antimetabolite (such as folate antagonists, pyrimidine analogs, purine analogs, and sugar-modified analogs), a DNA synthesis inhibitor, a DNA interactive agent (such as an intercalating agent), and a DNA repair inhibitor. Illustrative chemotherapeutic agents include, without limitation, the following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including *vinca* alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethylmelamineoxaliplatin, iphosphamide, melphalan, merchlorehtamine, mitomycin, mitoxantrone, nitrosourea, plicamycin, procarbazine, taxol, taxotere, temozolamide, teniposide, triethylenethiophosphoramide and etoposide (VP 16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (TNP470, genistein) and growth factor inhibitors (vascular endothelial growth factor (VEGF) inhibitors, fibroblast growth factor (FGF) inhibitors); angiotensin receptor blocker; nitric oxide donors; anti-sense oligonucleotides; antibodies (trastuzumab, rituximab); chimeric antigen receptors; cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin, irinotecan (CPT-11) and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers, toxins such as Cholera toxin, ricin, *Pseudomonas* exotoxin, *Bordetella pertussis* adenylate cyclase toxin, or diphtheria toxin, and caspase activators; and chromatin disruptors.

Cytokines are increasingly used to manipulate host immune response towards anticancer activity. See, e.g., Floros & Tarhini, *Semin. Oncol.* 42(4):539-548, 2015. Cytokines useful for promoting immune anticancer or antitumor response include, for example, IFN-α, IL-2, IL-3, IL-4, IL-10, IL-12, IL-13, IL-15, IL-16, IL-17, IL-18, IL-21, IL-24, and GM-CSF, singly or in any combination.

Another cancer therapy approach involves reducing expression of oncogenes and other genes needed for growth, maintenance, proliferation, and immune evasion by cancer cells. RNA interference, and in particular the use of microRNAs (miRNAs) small inhibitory RNAs (siRNAs) provides an approach for knocking down expression of cancer genes. See, e.g., Larsson et al., *Cancer Treat. Rev.* 16(55):128-135, 2017. Techniques for making and using RNA for cancer therapy are known to those having ordinary skill in the art.

In any of the embodiments disclosed herein, any of the therapeutic agents (e.g., an eIF4A inhibitor, an inhibitor of an immune suppression component, an agonist of a stimulatory immune checkpoint molecule, an antitumor lymphocyte, a chemotherapeutic agent, a radiation therapy, a surgery, a cytokine, or an inhibitory RNA) may be administered once or more than once to the subject over the course of a treatment, and, in combinations, may be administered to the subject in any order or any combination. An appropriate dose, suitable duration, and frequency of administration of the compositions will be determined by such factors as a condition of the patient; size, type, spread, growth, and severity of the tumor or cancer; particular form of the active ingredient; and the method of administration.

The methods and compositions disclosed herein may be useful in treating one or more forms of cancer, including cancers associated with non-inflamed solid tumors. In any of the embodiments disclosed herein, a non-inflamed solid tumor comprises a sarcoma, a carcinoma, a glioma, a lymphoma, or any combination thereof. In any of the embodiments disclosed herein, a subject being treated has, or is suspected of having a cancer of the head or neck, melanoma, pancreatic cancer, cholangiocarcinoma, hepatocellular cancer, breast cancer, gastric cancer, non-small-cell lung cancer, prostate cancer, esophageal cancer, mesothelioma, small-cell lung cancer, colorectal cancer, glioblastoma, or any combination thereof. In certain embodiments, the cancer comprises Askin's tumor, sarcoma botryoides, chondrosarcoma, Ewing's sarcoma, PNET, malignant hemangioendothelioma, malignant schwannoma, osteosarcoma, alveolar soft part sarcoma, angiosarcoma, cystosarcoma phyllodes, dermatofibrosarcoma protuberans (DFSP), desmoid tumor, desmoplastic small round cell tumor, epithelioid sarcoma, extraskeletal chondrosarcoma, extraskeletal osteosarcoma, fibrosarcoma, gastrointestinal stromal tumor (GIST), hemangiopericytoma, hemangiosarcoma, Kaposi's sarcoma, leiomyosarcoma, liposarcoma, lymphangiosarcoma, lymphosarcoma, undifferentiated pleomorphic sarcoma, malignant peripheral nerve sheath tumor (MPNST), neurofibrosarcoma, rhabdomyosarcoma, synovial sarcoma, undifferentiated pleomorphic sarcoma, squamous cell carcinoma, basal cell carcinoma, adenocarcinoma, linitis plastic, vipoma, cholangiocarcinoma, hepatocellular carcinoma, adenoid cystic carcinoma, renal cell carcinoma, Grawitz tumor, ependymoma, astrocytoma, oligodendroglioma, brainstem glioma, optice nerve glioma, a mixed glioma, Hodgkin's lymphoma, a B-cell lymphoma such as non-Hodgkin's lymphoma (NHL) (including Burkitt's lymphoma, small lymphocytic lymphoma (SLL), diffuse large B-cell lymphoma, follicular lymphoma, immunoblastic large cell lymphoma, precursor B-lymphoblastic lymphoma, and mantle cell lymphoma), Waldenström's macroglobulinemia, CD37+ dendritic cell lymphoma, lymphoplasmacytic lymphoma, splenic marginal zone lymphoma, extranodal marginal zone B-cell lymphoma of mucosa-associated (MALT) lymphoid tissue, nodal marginal zone B-cell lymphoma, mediastinal (thymic) large B-cell lymphoma, intravascular large B-cell lymphoma, primary effusion lymphoma, adult T-cell lymphoma, extranodal NK/T-cell lymphoma, nasal type, enteropathy-associated T-cell lymphoma, hepatosplenic T-cell lymphoma, blastic NK cell lymphoma, Sezary syndrome, angioimmunoblastic T cell lymphoma, anaplastic large cell lymphoma, or any combination thereof.

Also provided herein are methods of disrupting an extracellular matrix of a cell in a non-inflamed solid tumor in a subject, wherein the method comprises administering to the subject a therapeutically effective amount of an eIF4A inhibitor. In certain embodiments, a method of disrupting an extracellular matrix of a cell in a non-inflamed solid tumor comprises administering an effective amount of an eIF4A inhibitor selected from (a) a rocaglamate or a derivative thereof, or (b) a compound in accordance with Formula I:

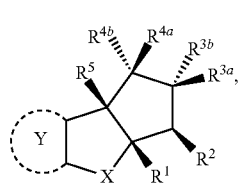

(I)

or stereoisomers, tautomers or pharmaceutically acceptable salts thereof, wherein:

X is $CR^6R^7$, O, S, NH, $N(C_1-C_8)$alkyl, C(O), $C=CR^6R^7$, $N(CO)R^8$, S(O) or $S(O)_2$;

Y is a 5-membered heteroaryl or a 6-membered aryl or heteroaryl;

$R^1$ and $R^2$ independently are aryl, heterocyclyl, heteroaryl or cycloalkyl;

$R^{3a}$, $R^{3b}$, $R^{4a}$ and $R^{4b}$ independently are H, halogen, CN, $C_1-C_8$(alkyl), $(C_1-C_8)$haloalkyl, $C_2-C_8$(alkenyl), $(C_2-C_8)$alkynyl, $OR^9$, $NHR^9$, $NR^9R^9$, $[(C_1-C_8)$alkylene$]OR^9$, $[(C_1-C_8)$alkylene$]NHR^9$, $[(C_1-C_8)$alkylene$]NR^9R^9$, $C(O)R^8$, $C(O)NHR^9$, $C(O)NR^9R^9$, $C(O)[(C_1-C_8)$alkylene$]NHR^9$, $C(O)[(C_1-C_8)$alkylene$]NR^9R^9$, $CO_2R^9$, $C(S)NHR^9$, $C(S)NR^9R^9$, $SR^9$, $S(O)R^9$, $SO_2R^9$, $SO_2NHR^9$, $SO_2NR^9R^9$, $NH(CO)R^8$, $NR^9(CO)R^8$, $NH(CO)NHR^9$, $NH(CO)NR^9R^9$, $NR^9(CO)NHR^9$, $NR^9(CO)NR^9R^9$, $P(O)(OH)(OR^9)$, $P(O)(OR^9)(OR^9)$, aryl, heteroaryl, cycloalkyl or heterocyclyl;

$R^{3a}$ and $R^{3b}$, and $R^{4a}$ and $R^{4b}$ independently combine to form oxo or alkenyl, or a cycloalkyl or heterocyclyl ring; or $R^{3a}$ and $R^{4a}$, $R^{3b}$ and $R^{4b}$ or $R^{4a}$ and $R^5$ together with the carbon atom to which they are attached form a cycloalkyl or heterocyclyl ring; or $R^2$ and $R^{3a}$ together with the carbon atom to which they are attached form a bicyclic ring system;

$R^5$ is H, halogen, OH, CN, $N_3$, $SR^9$, $(C_1-C_8)$alkyl, $(C_1-C_8)$haloalkyl, $O(C_1-C_8)$alkyl, $O(C_1-C_8)$haloalkyl, $(C_2-C_8)$alkynyl, $NHC(O)(C_1-C_8)$alkyl or heteroaryl; $R^6$ and $R^7$ independently are H, CN, halogen, $OR^9$, $SR^9$, $(C_1-C_8)$alkyl, $NH(R^9)$ or $NR^9R^9$;

$R^8$ is H, $(C_1-C_8)$alkyl, $(C_1-C_8)$haloalkyl, $O(C_1-C_8)$alkyl, $O(C_1-C_8)$haloalkyl, cycloalkyl, O(cycloalkyl), heterocyclyl, O(heterocyclyl), aryl, O(aryl), heteroaryl or O(heteroaryl);

$R^9$ is H, $(C_1-C_8)$alkyl, $(C_1-C_8)$haloalkyl, cycloalkyl, heterocyclyl, $[(C_1-C_8)$alkylene$]$ heterocyclyl, aryl, $[(C_1-C_8)$alkylene$]$ aryl or heteroaryl;

wherein the two $R^9$'s together with the nitrogen atom to which they are attached of $NR^9R^9$, $[(C_1-C_8)$alkylene$]NR^9R^9$, $C(O)NR^9R^9$, $C(O)[(C_1-C_8)$alkylene$]NR^9R^9$, $C(S)NR^9R^9$, $SO_2NR^9R^9$, $NH(CO)NR^9R^9$ or $NR^9(CO)NR^9R^9$, optionally form a heterocyclyl ring;

wherein any alkyl, alkenyl, cycloalkyl, heterocyclyl, heteroaryl or aryl is optionally substituted with 1, 2, or 3 groups selected from OH, CN, SH, $SO_2NH_2$, $SO_2(C_1-C_4)$alkyl, $SO_2NH(C_1-C_4)$alkyl, halogen, $NH_2$, $NH(C_1-C_4)$alkyl, $N[(C_1-C_4)$alkyl$]_2$, $C(O)NH_2$, COOH, COOMe, acetyl, $(C_1-C_8)$alkyl, $O(C_1-C_8)$alkyl, $O(C_1-C_8)$haloalkyl, $(C_2-C_8)$alkenyl, $(C_2-C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—$[CH(OH)]_m$—$(CH_2)_p$—OH, $CH_2$—$[CH(OH)]_m$—$(CH_2)_p$—$NH_2$ or $CH_2$-aryl-alkoxy; or wherein any alkyl, cycloalkyl or heterocyclyl is optionally substituted with oxo;

"m" and "p" are 1, 2, 3, 4, 5 or 6; and wherein when Y is a 6-membered aryl then X is not O.

In particular embodiments, an eIF4A inhibitor is a compound according to the following formula:

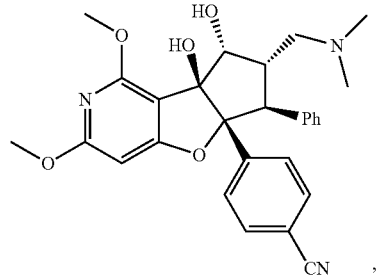

or a stereoisomer, tautomer, or pharmaceutically acceptable salt thereof.

Uses

In another aspect, the present disclosure provides uses of any of the herein described eIF4A inhibitors in the manufacture of a medicament for treating a non-inflamed solid tumor in a subject. In another aspect, the present disclosure provides use of an eIF4A inhibitor as described herein in the manufacture of a medicament for treating a cancer associated with a non-inflamed solid tumor. In certain embodiments, an eIF4A inhibitor useful in the manufacture of a medicament of the present disclosure comprises (a) a rocaglamate or derivative thereof or (b) a compound in accordance with Formula I:

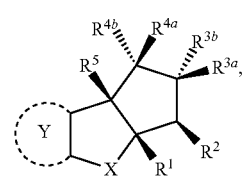

(I)

or stereoisomers, tautomers or pharmaceutically acceptable salts thereof, wherein:

X is $CR^6R^7$, O, S, NH, $N(C_1-C_8)$alkyl, C(O), $C=CR^6R^7$, $N(CO)R^8$, S(O) or $S(O)_2$;

Y is a 5-membered heteroaryl or a 6-membered aryl or heteroaryl;

$R^1$ and $R^2$ independently are aryl, heterocyclyl, heteroaryl or cycloalkyl;

$R^{3a}$, $R^{3b}$, $R^{4a}$ and $R^{4b}$ independently are H, halogen, CN, $C_1-C_8$(alkyl), $(C_1-C_8)$haloalkyl, $C_2-C_8$(alkenyl), $(C_2-C_8)$ alkynyl, $OR^9$, $NHR^9$, $NR^9R^9$, $[(C_1-C_8)$alkylene$]OR^9$, $[(C_1-C_8)$alkylene$]NHR^9$, $[(C_1-C_8)$alkylene$]NR^9R^9$, $C(O)R^8$, $C(O)NHR^9$, $C(O)NR^9R^9$, $C(O)[(C_1-C_8)$alkylene$]NHR^9$, $C(O)[(C_1-C_8)$alkylene$]NR^9R^9$, $CO_2R^9$, $C(S)NHR^9$, $C(S)NR^9R^9$, $SR^9$, $S(O)R^9$, $SO_2R^9$, $SO_2NHR^9$, $SO_2NR^9R^9$, $NH(CO)R^8$, $NR^9(CO)R^8$, $NH(CO)NHR^9$, $NH(CO)NR^9R^9$, $NR^9(CO)NHR^9$, $NR^9(CO)NR^9R^9$, $P(O)(OH)(OR^9)$, $P(O)(OR^9)(OR^9)$, aryl, heteroaryl, cycloalkyl or heterocyclyl;

$R^{3a}$ and $R^{3b}$, and $R^{4a}$ and $R^{4b}$ independently combine to form oxo or alkenyl, or a cycloalkyl or heterocyclyl ring; or $R^{3a}$ and $R^{4a}$, $R^{3b}$ and $R^{4b}$ or $R^{4a}$ and $R^5$ together with the carbon atom to which they are attached form a cycloalkyl or heterocyclyl ring; or $R^2$ and $R^{3a}$ together with the carbon atom to which they are attached form a bicyclic ring system;

$R^5$ is H, halogen, OH, CN, $N_3$, $SR^9$, $(C_1-C_8)$alkyl, $(C_1-C_8)$haloalkyl, $O(C_1-C_8)$alkyl, $O(C_1-C_8)$haloalkyl, $(C_2-C_8)$ alkynyl, $NHC(O)(C_1-C_8)$alkyl or heteroaryl;

$R^6$ and $R^7$ independently are H, CN, halogen, $OR^9$, $SR^9$, $(C_1-C_8)$alkyl, $NH(R^9)$ or $NR^9R^9$;

$R^8$ is H, $(C_1-C_8)$alkyl, $(C_1-C_8)$haloalkyl, $O(C_1-C_8)$alkyl, $O(C_1-C_8)$haloalkyl, cycloalkyl, O(cycloalkyl), heterocyclyl, O(heterocyclyl), aryl, O(aryl), heteroaryl or O(heteroaryl);

$R^9$ is H, $(C_1-C_8)$alkyl, $(C_1-C_8)$haloalkyl, cycloalkyl, heterocyclyl, $[(C_1-C_8)$alkylene$]$ heterocyclyl, aryl, $[(C_1-C_8)$alkylene$]$ aryl or heteroaryl;

wherein the two $R^9$'s together with the nitrogen atom to which they are attached of $NR^9R^9$, $[(C_1-C_8)$alkylene$]$ $NR^9R^9$, $C(O)NR^9R^9$, $C(O)[(C_1-C_8)$alkylene$]NR^9R^9$, $C(S)NR^9R^9$, $SO_2NR^9R^9$, $NH(CO)NR^9R^9$ or $NR^9(CO)NR^9R^9$, optionally form a heterocyclyl ring;

wherein any alkyl, alkenyl, cycloalkyl, heterocyclyl, heteroaryl or aryl is optionally substituted with 1, 2, or 3 groups selected from OH, CN, SH, $SO_2NH_2$, $SO_2(C_1-C_4)$alkyl, $SO_2NH(C_1-C_4)$alkyl, halogen, $NH_2$, $NH(C_1-C_4)$alkyl, $N[(C_1-C_4)$alkyl$]_2$, $C(O)NH_2$, COOH, COOMe, acetyl, $(C_1-C_8)$alkyl, $O(C_1-C_8)$alkyl, $O(C_1-C_8)$haloalkyl, $(C_2-C_8)$alkenyl, $(C_2-C_8)$alkynyl, haloalkyl, thioalkyl, cyanomethylene, alkylaminyl, $NH_2-C(O)$-alkylene, NH(Me)-C(O)-alkylene, $CH_2-C(O)$-lower alkyl, C(O)-lower alkyl, alkylcarbonylaminyl, $CH_2-[CH(OH)]_m-(CH_2)_p-OH$, $CH_2-[CH(OH)]_m(CH_2)_p-NH_2$ or $CH_2$-aryl-alkoxy; or wherein any alkyl, cycloalkyl or heterocyclyl is optionally substituted with oxo;

"m" and "p" are 1, 2, 3, 4, 5 or 6; and wherein when Y is a 6-membered aryl then X is not O.

In particular embodiments, an eIF4A inhibitor is a compound according to the following formula:

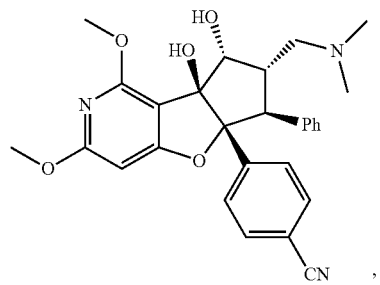

or a stereoisomer, tautomer, or pharmaceutically acceptable salt thereof.

EXAMPLES

Example 1

Effect of eIF4A Inhibitors on Tumor Stromal Remodeling

Cmp1 and Cmp2 are potent and sequence-selective eIF4A inhibitors that regulate eIF4A through a reversible enhancement of eIF4A binding to mRNAs with specific polypurine motifs within the 5'-untranslated region (UTR). Oncoprotein expression is tightly controlled at the level of protein synthesis and is largely regulated by the eukaryotic translation initiation factor 4F (eIF4F), a complex consisting of eIF4A, eIF4E and eIF4G. eIF4F catalyzes the recruitment of mRNA to the 40S ribosomal subunit to form the 48S initiation complex. The translation initiation factor eIF4A is a member of the "DEAD box" family of ATP-dependent helicases that catalyze the ATP-dependent unwinding of RNA duplexes, and facilitates 43 S ribosome complex scanning within the 5'-UTR until encountering an initiation codon.

Myofibroblasts are believed to be associated with tumor growth, vascularization, and metastasis (see, e.g., Webber et al., *Cancer Res.* 70:9621, 2010). The ability of Cmp1 or Cmp2 to inhibit the TGFβ-mediated fibroblast-to-myofibroblast transformation and components of the extracellular matrix was evaluated in fibroblasts.

Briefly, fibroblasts (Lonza #CC-2512; cell passage numbers 2 through 5 were used for all experiments) were seeded (Day 0) and cultured in Dulbecco's modified Eagle medium (DMEM) supplemented with 10% fetal bovine serum (FBS), penicillin, streptomycin and glutamax (Invitrogen) at 37° C. in a humidified incubator with 5% $CO_2$ overnight. On Day 1, cells were washed with phosphate buffered saline (PBS), and then incubated for 48 hours in fresh serum-free DMEM supplemented with penicillin, streptomycin, and glutamax. On Day 3, cells were washed, followed by addition of fresh serum-free DMEM containing eIF4A inhibitor Cmp1 or Cmp2 (0, 1.5, 4, 13, or 40 nM) and 10 ng/ml TGFβ, and cultured for 24 hours. Controls included untreated cells and cells treated with TGFβ only.

After a 24-hour incubation period, the effects of eIF4A inhibition on fibroblast transformation and production of extracellular matrix components were evaluated. Smooth muscle actin (α-SMA) protein levels were analyzed by western blot. Procollagen type 1 C-Peptide (PIPC) levels were analyzed by collecting culture media, centrifuging to pellet cellular debris, and quantifying using the (PIP) EIA kit (Clontech, Cat. No. MK101) according to the manufacturer's instructions.

Results

Figure 2A:
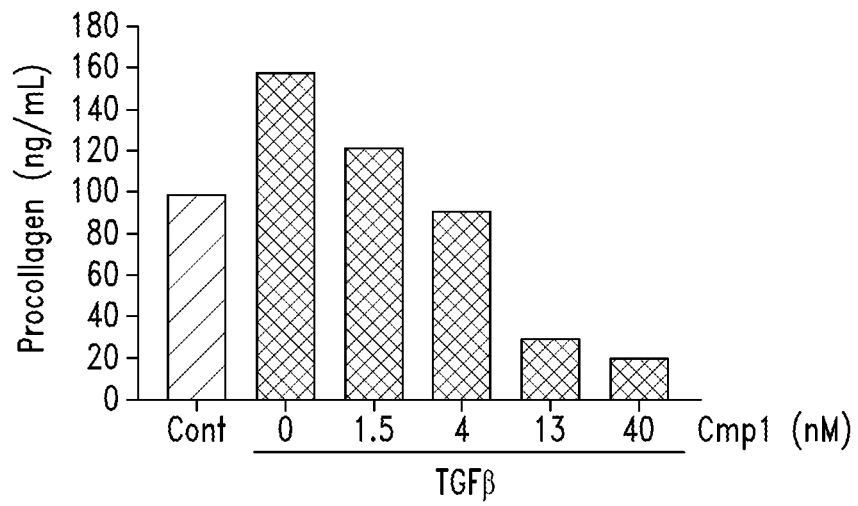
FIGS. 2A and 2B show the effect of (A) Cmp1 and (B) Cmp2 on the induction of procollagen secretion from fibroblasts treated with TGFβ. Procollagen type 1 levels (Procollagen Type 1C-Peptide, "PIPC") were measured after 24 hours of treating fibroblasts with various concentrations of the eIF4A inhibitors and 10 ng/mL TGFβ.
Figure 2B:
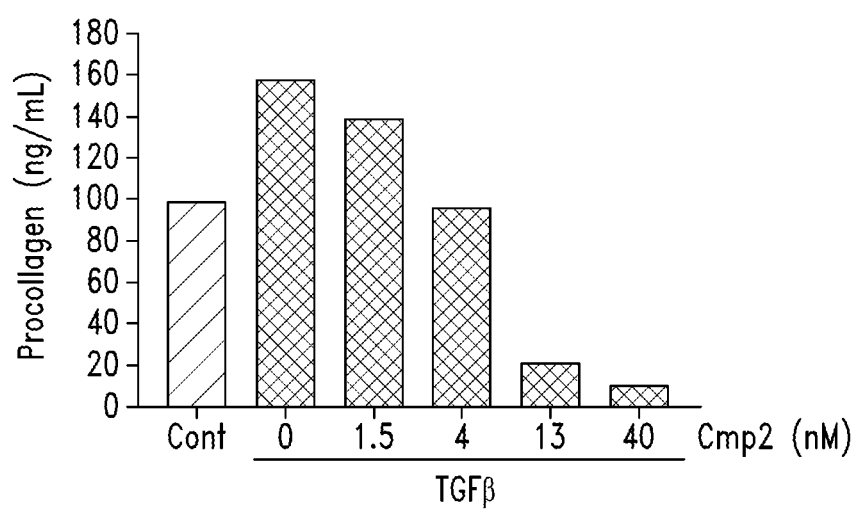

Transformation of fibroblasts into myofibroblasts by 24-hour treatment with TGFβ was assessed by expression of the TGFβ-induced myofibroblast differentiation marker, smooth muscle actin (α-SMA), and by the production of extracellular matrix components such as collagen type I. Analysis of α-SMA protein levels by western blot after 24-hour TGFβ treatment confirmed an increase in α-SMA corresponding to fibroblast transformation, as well as an increase in extracellular matrix procollagen production. Co-incubation of cells with TGFβ and an eIF4A inhibitor (Cmp1 or Cmp2) caused a dose-dependent reduction of the α-SMA protein level, such that the ratio of a-SMA to β-actin at higher Cmp1 or Cmp2 concentrations approached that of untransformed, untreated fibroblasts (FIG. 1). Treatment with an eIF4A inhibitor (Cmp1 or Cmp2) also blocked the increase in procollagen type I secretion, a component of the extracellular matrix (FIGS. 2A and 2B).

Conclusions

A hallmark of TGFβ-mediated fibroblast transformation into myofibroblasts is an increase in α-SMA and in extracellular matrix components such as collagen. Co-administration of eIF4A inhibitors Cmp1 or Cmp2 with TGFβ blocked fibroblast-to-myofibroblast transformation, as seen by an inhibition of a-smooth muscle actin. Cmp1 and Cmp2 were also observed to inhibit the production of extracellular matrix components that are upregulated during differentiation, as evidenced by an inhibition of increased levels of type 1 procollagen.

Example 2

Effect of eIF4A Inhibition on TGFβ and Extracellular Matrix Production

Figure 3A:
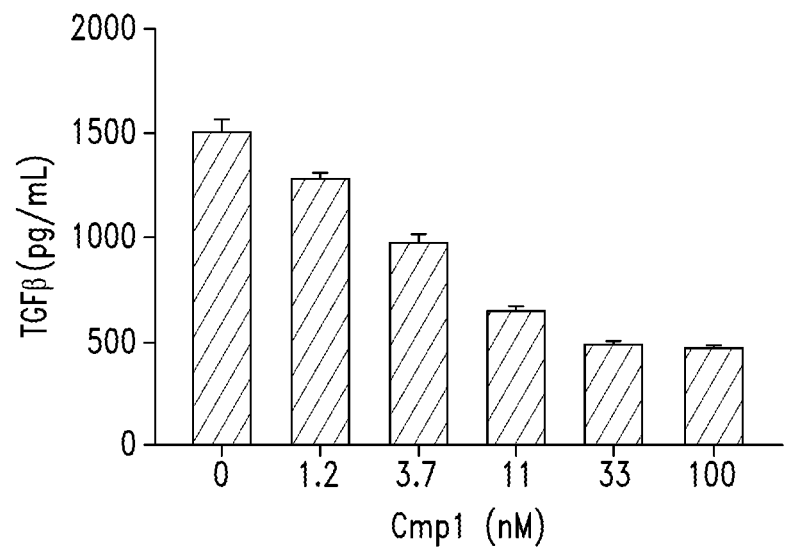
FIGS. 3A and 3B show the effect of Cmp1 on (A) the induction of TGFβ secretion and (B) procollagen secretion from myofibroblasts. Fibroblasts were transformed into myofibroblasts with 10 ng/mL TGFβ treatment for 24 hours. TGFβ was washed out and the myofibroblasts were treated with various concentrations of Cmp1 for 48 hours.
Figure 3B:
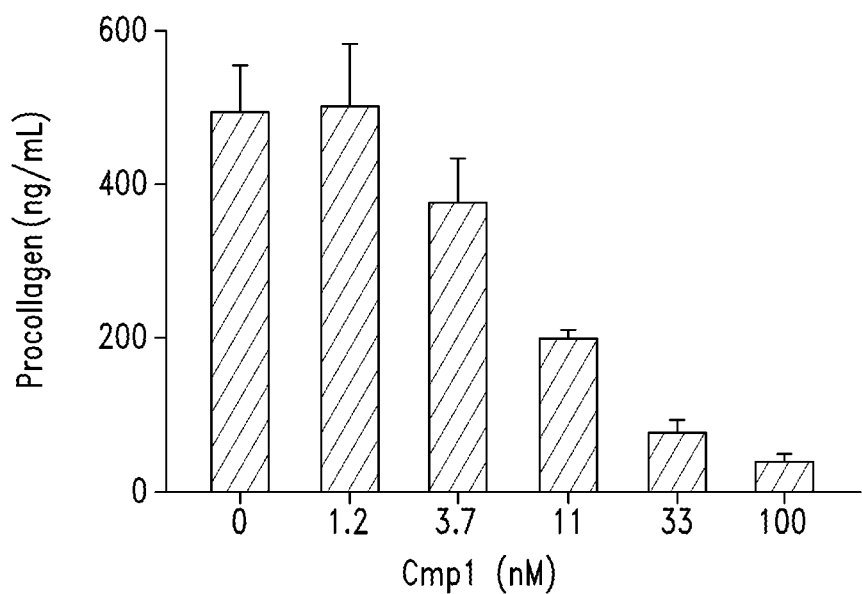

Briefly, fibroblasts (Lonza #CC-2512; cell passage numbers 2 through 5 were used for all experiments) were seeded (Day 0) and cultured in Dulbecco's modified Eagle medium (DMEM) supplemented with 10% fetal bovine serum (FBS), penicillin, streptomycin and glutamax (Invitrogen) at 37° C. in a humidified incubator with 5% $CO_2$ overnight. On Day 1, cells were washed with phosphate buffered saline (PBS), and then incubated for 72 hours in fresh serum-free DMEM supplemented with penicillin, streptomycin, and glutamax. On Day 4, cells were washed, followed by addition of fresh serum-free DMEM containing 10 ng/ml TGFβ, and cultured for 24 hours. On Day 5, cells were washed, followed by addition of fresh serum-free DMEM containing eIF4A inhibitor Cmp1 (0, 1.2, 3.7, 11.1, 33.3 or 100 nM), and cultured. Controls included untreated cells. At 48 hours post-addition of eIF4A inhibitor, 300 ul of culture media was harvested, centrifuged to pellet cellular debris, and frozen at −80° C. TGFβ1 in the culture medium was quantified using the Human TGF-B1 ELISA kit (R&D System DY240-05) according to the manufacturer's instructions. Procollagen type 1 C-Peptide (PIPC) levels were analyzed using the (PIP) EIA kit (Clontech, Cat. No. MK101) according to the manufacturer's instructions.
Results Myofibroblasts were differentiated and activated using exogenous addition of transforming growth factor-β. The ability of Cmp1 to inhibit TGFβ secretion from pre-formed myofibroblasts was evaluated by ELISA analysis. As shown in FIG. 3A, treatment of myofibroblasts for 48 hours with eIF4A inhibitor Cmp1 reduced the levels of secreted TGFβ in a dose-dependent manner. Inhibition of TGFβ with Cmp1 treatment led to a corresponding dose-dependent decrease in procollagen type I levels (FIG. 3B).

Conclusions

Pre-formed myofibroblasts secrete TGFβ, leading to the continued expression of extracellular matrix components such as collagen type I. Treatment of pre-formed myofibroblasts with an eIF4A inhibitor (Cmp1) inhibited the secretion of TGFβ and procollagen type I, indicating that inhibition of eIF4A can alter tumor stromal remodeling by regulating TGFβ and collagen production. These data show that eIF4A inhibition has the potential to impact T cell localization and infiltration into the tumor.

Example 3

Effect of Cmp1 on Tumor Infiltrating Lymphocytes

Stroma-rich tumor types (e.g., pancreatic ductal adenocarcinoma) are highly challenging cancers to treat. A complex network of soluble cytokines, growth factors, proteases, and components of the extracellular matrix collaboratively interacts within the tumor microenvironment, sustaining and driving cancer cell proliferation, invasion, and early metastasis, as well as mediating therapeutic resistance. Localization and migration of T cells is a prerequisite for antitumor immune surveillance. T cells are found to accumulate more efficiently in the stroma than in tumor, with the stromal extracellular matrix playing a key role in controlling the migration of T cells. Inhibition of extracellular matrix components increases T cell infiltration into the tumor, demonstrating that the stromal extracellular matrix influences antitumor immunity by controlling the positioning and migration of T cells.

To evaluate the effect of an eIF4A inhibitor on tumor infiltrating lymphocytes, an allograft tumor model was used. Briefly, KPC-3 (mouse pancreatic carcinoma) cells grown in DMEM supplemented with 10% FBS were harvested during exponential growth and counted for tumor inoculation in immune competent C57BL/6J mice. Each mouse was inoculated subcutaneously with $0.1 \times 10^6$ KPC-3 tumor cells in the right flank region in 0.1 mL volume comprising a 1:1 ratio (volume to volume) of cells in growth media and Matrigel® matrix (BD Biosciences, San Jose Calif.). Tumors were grown to 100-200 $mm^3$ prior to study initiation. Before beginning treatment, all animals were weighed and tumor volumes measured using a caliper. Since the tumor volume can affect the effectiveness of any given treatment, mice were randomly assigned into vehicle and test article treatment groups after tumors had reached a similar size. Each study group contained 8 mice, with each group receiving either vehicle (D5W) or Cmp1 administered parenterally on two dosing schedules (0.33 mg/kg Q2D and 1 mg/kg Q1W for 17 days). Following treatment, tumor biopsies were collected for four representative animals from each treatment group, formalin-fixed, and paraffin-embedded. Tumor samples were sectioned and stained with anti-CD3 and anti-CD8 antibodies or isotype control. A hematoxylin nuclear counterstain was also applied. Image analysis and quantification were conducted using ImageDx™. Increased $CD3^+$ and $CD8^+$ T cell staining within the tumor sample for eIF4A inhibitor treatment relative to vehicle indicates an increase in infiltrating lymphocytes into the tumor.

Results

Figure 4A:
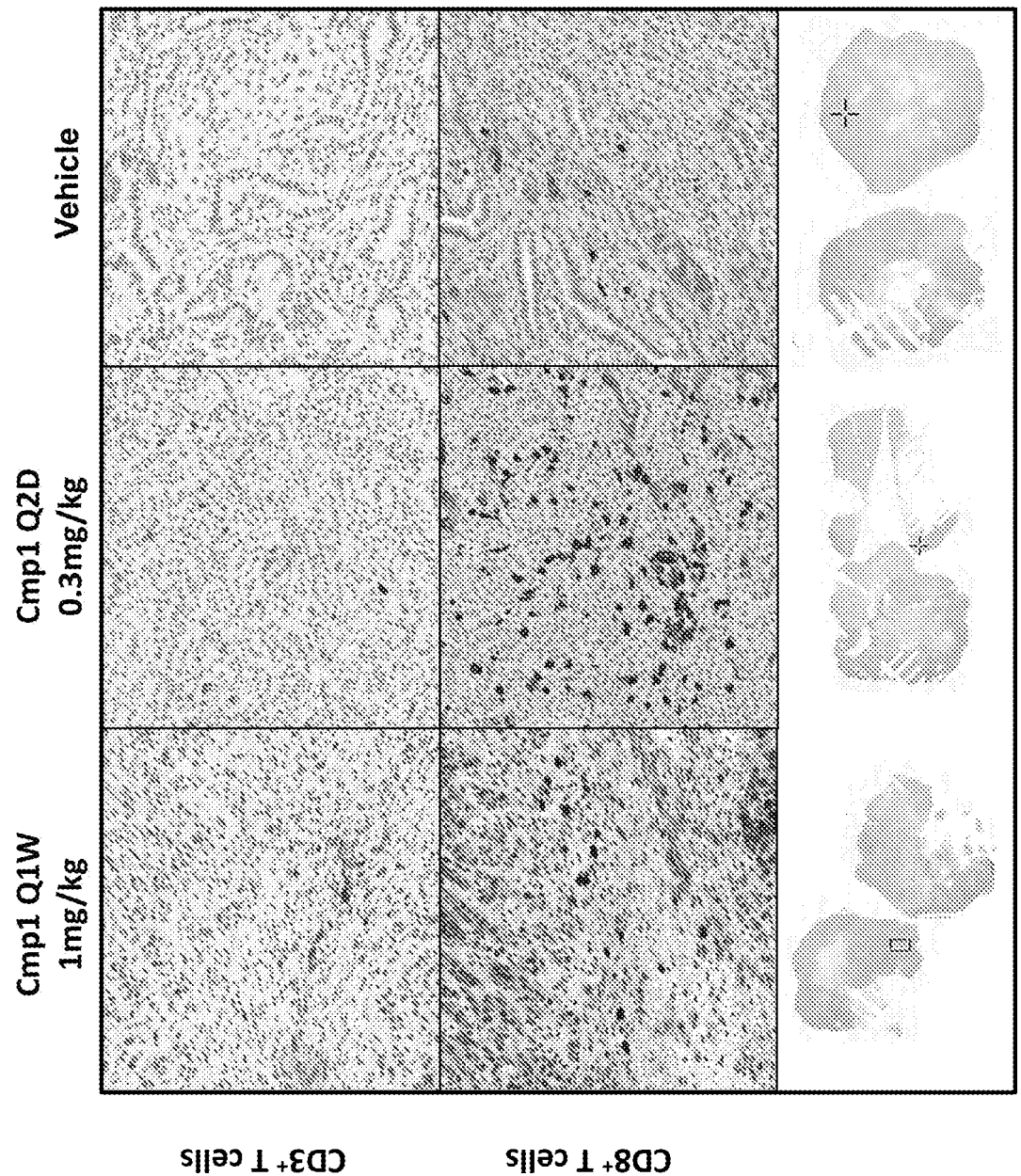
FIGS. 4A-4C show the in vivo effect of Cmp1 on immune cell infiltration using an allograft KPC3 tumor model. (A) $CD3^+$ and $CD8^+$ T cell infiltration in KPC3 tumor samples after treatment with Cmp1 (Q2D or Q1W) for 17 days was evaluated using IHC analysis. Positive density of (B) $CD3^+$ and (C) $CD8^+$ cells within tumor samples from treated allograft mice is quantified.
Figure 4B:
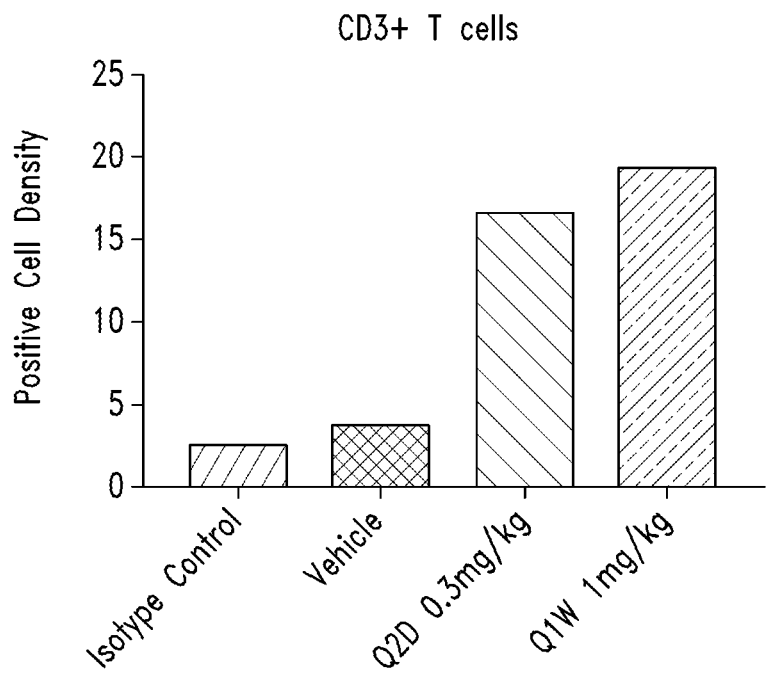
Figure 4C:
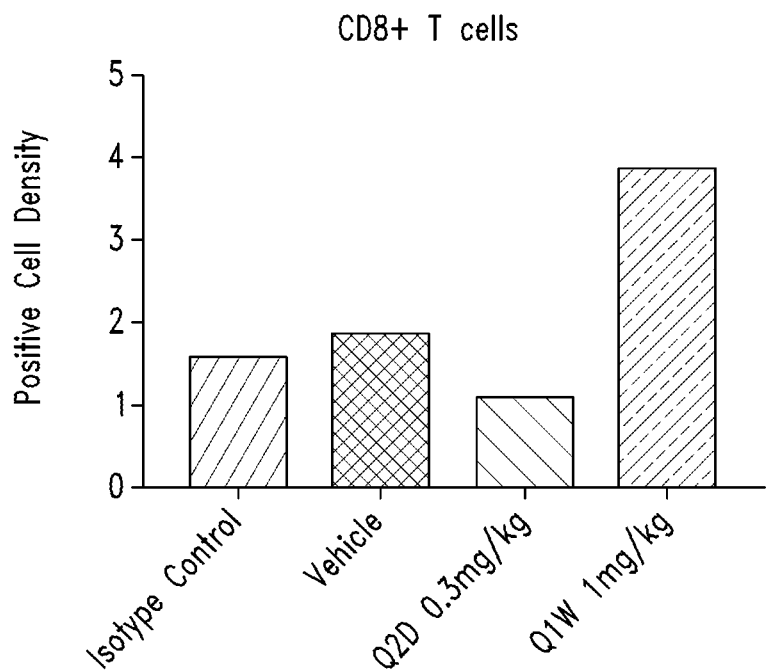

The ability of Cmp1 to regulate immune cell infiltration was evaluated in vivo in the mouse KPC-3 tumor model by IHC analysis (FIG. 4A). Minimal CD3- or CD8-positive T cells were detected in vehicle treated tumor samples. Administration of Cmp1 at 0.3 mg/kg Q2D or 1 mg/kg Q1W for 17 days resulted in a significant increase in $CD3^+$ T cells in the KPC-3 tumor samples (FIG. 4B). A significant increase in $CD8^+$ T cells was also observed for animals treated with 1 mg/kg Q1W Cmp1 (FIG. 4C).

CONCLUSIONS

The stromal extracellular matrix has been shown to influence antitumor immunity by controlling the localization and migration of T cells. eIF4A inhibitors were observed to alter the stromal extracellular matrix through reduction in TGF D levels, leading to the down-regulation in collagen type I levels. In vivo treatment of the pancreatic KPC-3 tumor model with Cmp1 resulted in an increase in $CD3^+$ and $CD8^+$ T cells within the tumor. These results suggest that Cmp1 can alter the extracellular matrix and affect the localization of tumor infiltrating lymphocytes that can be important in eliciting immune responses.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, including U.S. Provisional Patent Application No. 62/510,643, filed May 24, 2017, are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A method for treating a non-inflamed solid tumor in a subject, the method comprising administering to the subject a therapeutically effective amount of an eIF4A inhibitor comprising a compound of formula I:

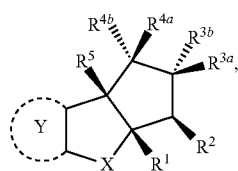

(I)

or stereoisomers, tautomers or pharmaceutically acceptable salts thereof,
wherein:
X is $CR^6R^7$, O, S, NH, $N(C_1-C_8)$alkyl, C(O), $C=CR^6R^7$, $N(CO)R^8$, S(O) or $S(O)_2$;
Y is a 5-membered heteroaryl or a 6-membered aryl or heteroaryl;

$R^1$ and $R^2$ independently are aryl, heterocyclyl, heteroaryl or cycloalkyl;

$R^{3a}$, $R^{3b}$, $R^{4a}$ and $R^{4b}$ independently are H, halogen, CN, $C_1-C_8$(alkyl), $(C_1-C_8)$haloalkyl, $C_2-C_8$(alkenyl), $(C_2-C_8)$alkynyl, $OR^9$, $NHR^9$, $NR^9R^9$, $[(C_1-C_8)$alkylene]$OR^9$, $[(C_1-C_8)$alkylene]$NHR^9$, $[(C_1-C_8)$alkylene]$NR^9R^9$, $C(O)R^8$, $C(O)NHR^9$, $C(O)NR^9R^9$, $C(O)[(C_1-C_8)$alkylene]$NHR^9$, $C(O)[(C_1-C_8)$alkylene]$NR^9R^9$, $CO_2R^9$, $C(S)NHR^9$, $C(S)NR^9R^9$, $SR^9$, $S(O)R^9$, $SO_2R^9$, $SO_2NHR^9$, $SO_2NR^9R^9$, $NH(CO)R^8$, $NR^9(CO)R^8$, $NH(CO)NHR^9$, $NH(CO)NR^9R^9$, $NR^9(CO)NHR^9$, $NR^9(CO)NR^9R^9$, $P(O)(OH)(OR^9)$, $P(O)(OR^9)(OR^9)$, aryl, heteroaryl, cycloalkyl or heterocyclyl;

$R^{3a}$ and $R^{3b}$, and $R^{4a}$ and $R^{4b}$ independently combine to form oxo or alkenyl, or a cycloalkyl or heterocyclyl ring; or $R^{3a}$ and $R^{4a}$, $R^{3b}$ and $R^{4b}$ or $R^{4a}$ and $R^5$ together with the carbon atom to which they are attached form a cycloalkyl or heterocyclyl ring; or $R^2$ and $R^{3a}$ together with the carbon atom to which they are attached form a bicyclic ring system;

$R^5$ is H, halogen, OH, CN, $N_3$, $SR^9$, $(C_1-C_8)$alkyl, $(C_1-C_8)$haloalkyl, $O(C_1-C_8)$alkyl, $O(C_1-C_8)$haloalkyl, $(C_2-C_8)$alkynyl, $NHC(O)(C_1-C_8)$alkyl or heteroaryl;

$R^6$ and $R^7$ independently are H, CN, halogen, $OR^9$, $SR^9$, $(C_1-C_8)$alkyl, $NH(R^9)$ or $NR^9R^9$;

$R^8$ is H, $(C_1-C_8)$alkyl, $(C_1-C_8)$haloalkyl, $O(C_1-C_8)$alkyl, $O(C_1-C_8)$haloalkyl, cycloalkyl, O(cycloalkyl), heterocyclyl, O(heterocyclyl), aryl, O(aryl), heteroaryl or O(heteroaryl);

$R^9$ is H, $(C_1-C_8)$alkyl, $(C_1-C_8)$haloalkyl, cycloalkyl, heterocyclyl, $[(C_1-C_8)$alkylene] heterocyclyl, aryl, $[(C_1-C_8)$alkylene] aryl or heteroaryl;

wherein the two $R^9$'s together with the nitrogen atom to which they are attached of $NR^9R^9$, $[(C_1-C_8)$alkylene]$NR^9R^9$, $C(O)NR^9R^9$, $C(O)[(C_1-C_8)$alkylene]$NR^9R^9$, $C(S)NR^9R^9$, $SO_2NR^9R^9$, $NH(CO)NR^9R^9$ or $NR^9(CO)NR^9R^9$, optionally form a heterocyclyl ring;

wherein any alkyl, alkenyl, cycloalkyl, heterocyclyl, heteroaryl or aryl is optionally substituted with 1, 2, or 3 groups selected from OH, CN, SH, $SO_2NH_2$, $SO_2(C_1-C_4)$alkyl, $SO_2NH(C_1-C_4)$alkyl, halogen, $NH_2$, $NH(C_1-C_4)$alkyl, $N[(C_1-C_4)$alkyl$]_2$, $C(O)NH_2$, COOH, COOMe, acetyl, $(C_1-C_8)$alkyl, $O(C_1-C_8)$alkyl, $O(C_1-C_8)$haloalkyl, $(C_2-C_8)$alkenyl, $(C_2-C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—[CH(OH)]$_m$—(CH$_2$)$_p$—OH, $CH_2$—[CH(OH)]$_m$—(CH$_2$)$_p$—$NH_2$ or $CH_2$-aryl-alkoxy; or wherein any alkyl, cycloalkyl or heterocyclyl is optionally substituted with oxo;

"m" and "p" are 1, 2, 3, 4, 5 or 6; and wherein when Y is a 6-membered aryl then X is not O, thereby promoting infiltration of the non-inflamed solid tumor by antitumor lymphocytes, wherein the tumor is a melanoma, pancreatic cancer, hepatocellular cancer, breast cancer, lung cancer, prostate cancer, colorectal cancer, glioblastoma, or any combination thereof.

2. The method according to claim 1, wherein the eIF4A inhibitor is a compound according to the following formula:

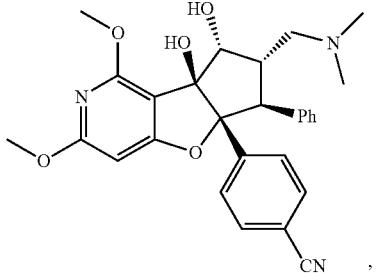

231F or a stereoisomer, tautomer, or pharmaceutically acceptable salt thereof.

3. The method according to claim 1, wherein the compound of Formula I is administered orally, parenterally, sublingually, buccally, intravenously, via direct intratumoral injection, or any combination thereof.

4. The method according to claim 1, further comprising administering an inhibitor of an immune suppression component to the subject, wherein the inhibitor of the immune suppression component inhibits activity of PD-1, PD-L1, PD-L2, LAG3, CTLA4, B7-H3, B7-H4, CD244/2B4, HVEM, BTLA, CD160, TIM3, GALS, adenosine, A2aR, an immunosuppressive cytokine, IDO, arginase, VISTA, TIGIT, PVRIG, PVRL2, KIRs, LAIR1, CEACAM-1, CEACAM-3, CEACAM-5, CD160, Treg cells, or any combination thereof, and wherein the eIF4A inhibitor and the inhibitor of the immune suppression component are administered to the subject concurrently, contemporaneously, or sequentially.

5. The method according to claim 4, wherein the inhibitor of the immune suppression component is selected from the group consisting of an antibody or antigen binding fragment thereof, a fusion protein, a small molecule, an RNAi molecule, a ribozyme, an aptamer, an antisense oligonucleotide, or any combination thereof.

6. The method according to claim 5, wherein the inhibitor of the immune suppression component comprises pidilizumab, nivolumab, pembrolizumab, MEDI0680, AMP-224, BMS-936558 BMS-936559, durvalumab, atezolizumab, avelumab, MPDL3280A, LAG525, IMP321, IMP701, 9H12, BMS-986016, ipilimumab, tremelimumab, abatacept, belatacept, enoblituzumab, 376.96, an anti-B7-H4 antibody or antigen binding fragment thereof, lirilumab, levo-1-methyl tryptophan, epacadostat, ebselen, indoximod, NLG919, 1-methyl-tryptophan (1-MT)-tira-pazamine, N(omega)-Nitro-L-arginine methyl ester (L-NAME), N-omega-hydroxy-nor-1-arginine (nor-NOHA), L-NOHA, 2(S)-amino-6-boronohexanoic acid (ABH), S-(2-boronoethyl)-L-cysteine (BEC), CA-170, COM902, COM701, or antigen binding fragments thereof, or any combination thereof.

7. The method according to claim 1, further comprising administering to the subject a therapeutically effective amount of an agonist of a stimulatory immune checkpoint molecule, wherein the agonist is selected from urelumab, MEDI6469, MEDI6383, MEDI0562, lenalidomide, pomalidomide, CDX-1127, TGN1412, CD80, CD86, CP-870,893, rhuCD40L, SGN-40, IL-2, GSK3359609, mAb 88.2, JTX-2011, Icos 145-1, Icos 314-8, or any combination thereof.

8. The method according to claim 1, further comprising administering a therapeutically effective amount of a modified antitumor lymphocyte.

9. The method according to claim 8, wherein the modified antitumor lymphocytes comprise $CD8^+$ T cells, $CD4^+$ T cells, or both.

10. The method according to claim 8, wherein the modified antitumor lymphocytes were made from allogeneic T cells, autologous T cells, syngeneic T cells, or any combination thereof.

11. The method according to claim 8, wherein the modified antitumor lymphocytes comprise a heterologous receptor that specifically binds a cancer antigen expressed by the non-inflamed solid tumor.

12. The method according to claim 8, wherein the modified antitumor lymphocytes comprise:
  (a) T cells, comprising a chimeric antigen receptor, a heterologous T cell receptor, a heterologous high-affinity T cell receptor, or any combination thereof;
  (b) NK cells optionally comprising a chimeric antigen receptor, a heterologous T cell receptor, a heterologous high-affinity T cell receptor, or any combination thereof;
  (c) NK-T cells optionally comprising a chimeric antigen receptor, a heterologous T cell receptor, a heterologous high-affinity T cell receptor, or any combination thereof;
  (d) B cells producing one or more antibody specific for a cancer antigen expressed by the non-inflamed solid tumor; or
  (e) any combination of (a)-(d), wherein the chimeric antigen receptor specifically binds to and/or the TCR specifically binds to an antigen peptide: MHC complex, wherein the antigen is from a ROR1, EGFR, EGFRvIII, GD2, GD3, HPV E6, HPV E7, Her2, L1-CAM, Lewis A, Lewis Y, MUC1, MUC16, PSMA, CD19, CD20, CD22, CD56, CD23, CD24, CD37, CD30, CD33, CD38, CD56, CD123, CA125, c-MET, FcRH5, WT1, folate receptor α, VEGF-α, VEGFR1, VEGFR2, IL-13Rα2, IL-11Rα, MAGE-Al, PSA, ephrin A2, ephrin B2, NKG2D ligands, NY-ESO-1, TAG-72, mesothelin, or CEA.

13. The method according to claim 1, further comprising administering to the subject a secondary therapy selected from an antibody or antigen-binding fragment specific for a cancer antigen expressed on the non-inflamed solid tumor, a chemotherapeutic agent, surgery, radiation therapy, an anti-cancer cytokine, an RNA interference molecule, or any combination thereof, wherein the secondary therapy is administered simultaneously, concurrently, or sequentially with the eIF4A inhibitor.

14. The method according to claim 13, wherein the secondary therapy comprises a cytokine comprising IFN-α, IL-2, IL-3, IL-4, IL-10, IL-12, IL-13, IL-15, IL-16, IL-17, IL-18, IL-21, IL-24, and GM-CSF, or any combination thereof.

15. A method for disrupting an extracellular matrix of a cell in a non-inflamed solid tumor in a subject, the method comprising administering to the subject a therapeutically effective amount of an eIF4A inhibitor comprising a compound of formula I:

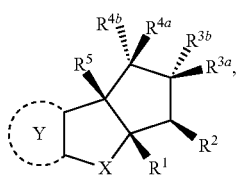

or stereoisomers, tautomers or pharmaceutically acceptable salts thereof,
wherein:
X is $CR^6R^7$, O, S, NH, $N(C_1-C_8)$alkyl, C(O), $C=CR^6R^7$, $N(CO)R^8$, S(O) or $S(O)_2$;
Y is a 5-membered heteroaryl or a 6-membered aryl or heteroaryl;
$R^1$ and $R^2$ independently are aryl, heterocyclyl, heteroaryl or cycloalkyl;
$R^{3a}$, $R^{3b}$, $R^{4a}$ and $R^{4b}$ independently are H, halogen, CN, $C_1-C_8$(alkyl), $(C_1-C_8)$haloalkyl, $C_2-C_8$(alkenyl), $(C_2-C_8)$alkynyl, $OR^9$, $NHR^9$, $NR^9R^9$, $[(C_1-C_8)$alkylene]$OR^9$, $[(C_1-C_8)$alkylene]$NHR^9$, $[(C_1-C_8)$alkylene]$NR^9R^9$, $C(O)R^8$, C(O)$NHR^9$, C(O)$NR^9R^9$, C(O)$[(C_1-C_8)$alkylene]$NHR^9$, C(O)$[(C_1-C_8)$alkylene]$NR^9R^9$, $CO_2R^9$, C(S)$NHR^9$, C(S)$NR^9R^9$, $SR^9$, $S(O)R^9$, $SO_2R^9$, $SO_2NHR^9$, $SO_2NR^9R^9$, NH(CO)$R^8$, $NR^9$(CO)$R^8$, NH(CO)$NHR^9$, NH(CO)$NR^9R^9$, $NR^9$(CO)$NHR^9$, $NR^9$(CO)$NR^9R^9$, P(O)(OH)($OR^9$), P(O)($OR^9$)($OR^9$), aryl, heteroaryl, cycloalkyl or heterocyclyl;
$R^{3a}$ and $R^{3b}$, and $R^{4a}$ and $R^{4b}$ independently combine to form oxo or alkenyl, or a cycloalkyl or heterocyclyl ring; or
$R^{3a}$ and $R^{4a}$, $R^{3b}$ and $R^{4b}$ or $R^{4a}$ and $R^5$ together with the carbon atom to which they are attached form a cycloalkyl or heterocyclyl ring; or
$R^2$ and $R^{3a}$ together with the carbon atom to which they are attached form a bicyclic ring system;
$R^5$ is H, halogen, OH, CN, $N_3$, $SR^9$, $(C_1-C_8)$alkyl, $(C_1-C_8)$haloalkyl, $O(C_1-C_8)$alkyl, $O(C_1-C_8)$haloalkyl, $(C_2-C_8)$alkynyl, NHC(O)$(C_1-C_8)$alkyl or heteroaryl;
$R^6$ and $R^7$ independently are H, CN, halogen, $OR^9$, $SR^9$, $(C_1-C_8)$alkyl, NH($R^9$) or $NR^9R^9$;
$R^8$ is H, $(C_1-C_8)$alkyl, $(C_1-C_8)$haloalkyl, $O(C_1-C_8)$alkyl, $O(C_1-C_8)$haloalkyl, cycloalkyl, O(cycloalkyl), heterocyclyl, O(heterocyclyl), aryl, O(aryl), heteroaryl or O(heteroaryl);
$R^9$ is H, $(C_1-C_8)$alkyl, $(C_1-C_8)$haloalkyl, cycloalkyl, heterocyclyl, $[(C_1-C_8)$alkylene] heterocyclyl, aryl, $[(C_1-C_8)$alkylene] aryl or heteroaryl;
wherein the two $R^9$'s together with the nitrogen atom to which they are attached of $NR^9R^9$, $[(C_1-C_8)$alkylene]$NR^9R^9$, C(O)$NR^9R^9$, C(O)$[(C_1-C_8)$alkylene]$NR^9R^9$, C(S)$NR^9R^9$, $SO_2NR^9R^9$, NH(CO)$NR^9R^9$ or $NR^9$(CO)$NR^9R^9$, optionally form a heterocyclyl ring;
wherein any alkyl, alkenyl, cycloalkyl, heterocyclyl, heteroaryl or aryl is optionally substituted with 1, 2, or 3 groups selected from OH, CN, SH, $SO_2NH_2$, $SO_2(C_1-C_4)$alkyl, $SO_2NH(C_1-C_4)$alkyl, halogen, $NH_2$, NH($C_1-C_4$)alkyl, N[($C_1-C_4$)alkyl]$_2$, C(O)$NH_2$, COOH, COOMe, acetyl, $(C_1-C_8)$alkyl, $O(C_1-C_8)$alkyl, $O(C_1-C_8)$haloalkyl, $(C_2-C_8)$alkenyl, $(C_2-C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—[CH(OH)]$_m$—$(CH_2)_p$—OH, $CH_2$—[CH(OH)]$_m$—$(CH_2)_p$—$NH_2$ or $CH_2$-aryl-alkoxy; or wherein any alkyl, cycloalkyl or heterocyclyl is optionally substituted with oxo;
"m" and "p" are 1, 2, 3, 4, 5 or 6; and
wherein when Y is a 6-membered aryl then X is not O;
wherein the non-inflamed solid tumor is a melanoma, pancreatic cancer, hepatocellular cancer, breast cancer, lung cancer, prostate cancer, colorectal cancer, glioblastoma, or any combination thereof.

16. A method for promoting infiltration of a non-inflamed solid tumor by antitumor lymphocytes, the method comprising administering to a subject having the cancer a therapeutically effective amount of an eIF4A inhibitor comprising a compound of formula I:

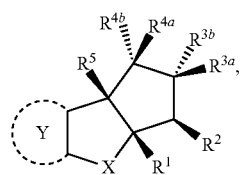

or stereoisomers, tautomers or pharmaceutically acceptable salts thereof,
wherein:
X is $CR^6R^7$, O, S, NH, $N(C_1-C_8)$alkyl, C(O), $C=CR^6R^7$, $N(CO)R^8$, S(O) or $S(O)_2$;
Y is a 5-membered heteroaryl or a 6-membered aryl or heteroaryl;
$R^1$ and $R^2$ independently are aryl, heterocyclyl, heteroaryl or cycloalkyl;
$R^{3a}$, $R^{3b}$, $R^{4a}$ and $R^{4b}$ independently are H, halogen, CN, $C_1-C_8$(alkyl), $(C_1-C_8)$haloalkyl, $C_2-C_8$(alkenyl), $(C_2-C_8)$alkynyl, $OR^9$, $NHR^9$, $NR^9R^9$, $[(C_1-C_8)$alkylene]$OR^9$, $[(C_1-C_8)$alkylene]$NHR^9$, $[(C_1-C_8)$alkylene]$NR^9R^9$, $C(O)R^8$, C(O)$NHR^9$, C(O)$NR^9R^9$, C(O)$[(C_1-C_8)$alkylene]$NHR^9$, C(O)$[(C_1-C_8)$alkylene]$NR^9R^9$, $CO_2R^9$, C(S)$NHR^9$, C(S)$NR^9R^9$, $SR^9$, $S(O)R^9$, $SO_2R^9$, $SO_2NHR^9$, $SO_2NR^9R^9$, NH(CO)$R^8$, $NR^9$(CO)$R^8$, NH(CO)$NHR^9$, NH(CO)$NR^9R^9$, $NR^9$(CO)$NHR^9$, $NR^9$(CO)$NR^9R^9$, P(O)(OH)($OR^9$), P(O)($OR^9$)($OR^9$), aryl, heteroaryl, cycloalkyl or heterocyclyl;
$R^{3a}$ and $R^{3b}$, and $R^{4a}$ and $R^{4b}$ independently combine to form oxo or alkenyl, or a cycloalkyl or heterocyclyl ring; or
$R^{3a}$ and $R^{4a}$, $R^{3b}$ and $R^{4b}$ or $R^{4a}$ and $R^5$ together with the carbon atom to which they are attached form a cycloalkyl or heterocyclyl ring; or
$R^2$ and $R^{3a}$ together with the carbon atom to which they are attached form a bicyclic ring system;
$R^5$ is H, halogen, OH, CN, $N_3$, $SR^9$, $(C_1-C_8)$alkyl, $(C_1-C_8)$haloalkyl, $O(C_1-C_8)$alkyl, $O(C_1-C_8)$haloalkyl, $(C_2-C_8)$alkynyl, NHC(O)$(C_1-C_8)$alkyl or heteroaryl;
$R^6$ and $R^7$ independently are H, CN, halogen, $OR^9$, $SR^9$, $(C_1-C_8)$alkyl, NH($R^9$) or $NR^9R^9$;
$R^8$ is H, $(C_1-C_8)$alkyl, $(C_1-C_8)$haloalkyl, $O(C_1-C_8)$alkyl, $O(C_1-C_8)$haloalkyl, cycloalkyl, O(cycloalkyl), heterocyclyl, O(heterocyclyl), aryl, O(aryl), heteroaryl or O(heteroaryl);
$R^9$ is H, $(C_1-C_8)$alkyl, $(C_1-C_8)$haloalkyl, cycloalkyl, heterocyclyl, $[(C_1-C_8)$alkylene] heterocyclyl, aryl, $[(C_1-C_8)$alkylene] aryl or heteroaryl;
wherein the two $R^9$'s together with the nitrogen atom to which they are attached of $NR^9R^9$, $[(C_1-C_8)$alkylene]$NR^9R^9$, C(O)$NR^9R^9$, C(O)$[(C_1-C_8)$alkylene]$NR^9R^9$, $C(S)NR^9R^9$, $SO_2NR^9R^9$, $NH(CO)NR^9R^9$ or $NR^9(CO)NR^9R^9$, optionally form a heterocyclyl ring;

wherein any alkyl, alkenyl, cycloalkyl, heterocyclyl, heteroaryl or aryl is optionally substituted with 1, 2, or 3 groups selected from OH, CN, SH, $SO_2NH_2$, $SO_2(C_1$-$C_4)$alkyl, $SO_2NH(C_1$-$C_4)$alkyl, halogen, $NH_2$, $NH(C_1$-$C_4)$alkyl, $N[(C_1$-$C_4)$alkyl$]_2$, $C(O)NH_2$, COOH, COOMe, acetyl, $(C_1$-$C_8)$alkyl, $O(C_1$-$C_8)$alkyl, $O(C_1$-$C_8)$haloalkyl, $(C_2$-$C_8)$alkenyl, $(C_2$-$C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—$[CH(OH)]_m$—$(CH_2)_p$—OH, $CH_2$—$[CH(OH)]_m$—$(CH_2)_p$—$NH_2$ or $CH_2$-aryl-alkoxy; or wherein any alkyl, cycloalkyl or heterocyclyl is optionally substituted with oxo;

"m" and "p" are 1, 2, 3, 4, 5 or 6; and wherein when Y is a 6-membered aryl then X is not O;

wherein the non-inflamed solid tumor is a melanoma, pancreatic cancer, hepatocellular cancer, breast cancer, lung cancer, prostate cancer, colorectal cancer, glioblastoma, or any combination thereof.

\* \* \* \* \*